(12) United States Patent
Weng et al.

(10) Patent No.: US 6,514,696 B1
(45) Date of Patent: Feb. 4, 2003

(54) TRANSCRIPTIONALLY REGULATED G PROTEIN-COUPLED RECEPTOR G2A

(75) Inventors: Zhigang Weng, Brookline, MA (US); Owen N. Witte, Sherman Oaks, CA (US)

(73) Assignee: The Regents of The University of California, Oakland, CA (US)

( * ) Notice: Subject to any disclaimer, the term of this patent is extended or adjusted under 35 U.S.C. 154(b) by 0 days.

(21) Appl. No.: 09/553,875

(22) Filed: Apr. 20, 2000

Related U.S. Application Data

(63) Continuation-in-part of application No. 09/120,025, filed on Jul. 17, 1998, now Pat. No. 6,214,562, which is a continuation-in-part of application No. 08/969,815, filed on Nov. 13, 1997, now Pat. No. 6,207,412.

(51) Int. Cl.$^7$ .......................... C12Q 1/68; G01N 33/50; C12N 15/12; C12N 15/63

(52) U.S. Cl. ........................ 435/6; 435/69.1; 435/91.2; 435/172.3; 435/252.3; 435/320.1; 536/23.1; 536/24.3; 530/300; 530/350

(58) Field of Search .......................... 435/6, 69.1, 91.2, 435/172.3, 252.3, 320.1; 536/23.1, 24.3; 530/300, 350

(56) References Cited

FOREIGN PATENT DOCUMENTS

WO    WO 99/25830    5/1999

OTHER PUBLICATIONS

J.H.S. Kabarowski et al., "Direct genetic demonstration of . . . rearrangement," PNAS, 97(22):12109–12114 (2000).
I.E. Zohn et al., "G2A is an oncogenic G protein–coupled receptor," Oncogene (2000) 19:3866–3877 (2000).
W.H. Moolenaar, "Bioactive Lysophospholipids and Their G Protein–Coupled Receptors," Experimental Cell Research (1999) 253:230–238
Y. Xu et al., "Sphingosylphosphorylcholine is a ligand . . . receptor 1," Nature Cell Biology, (2000) 2:261–267.
Afar et al., "Differential Complementation of Bcr–Abl Point Mutantas with c–Myc," Science (1999) 164:424–426.
Afar et al., "Signaling by ABL oncogenes through cyclin D1," Proc. Natl. Acad. Sci. USA (1995) 92:9540–9544.
Alkhatib et al., "CC CKR5: A Rantes . . . HIV–1," Science, 272:1955–1958 (1996).
Arvanitakis et al., "Human herpesvirus KSHV encodes a constitutively . . . proliferation," Nature 385:347–350 (1997).
Braun et al., "Identification of Target Genes . . . Analysis," Molecular and Cellular Biology 15(8):4623–4630 (1995).
Choe et al., "The β–Chemokine . . . Isolates," Cell, 85:1135–1148 (1996).
R.J. Davis, "Transcriptional Regulation by MAP Kinases," Molecular Reproduction and Development, 42:459–467 (1995).
Deng et al., "Identification of a major co–receptor for primary isolates of HIV–1," Nature, 381:661–666 (1996).
Choi et al., "Identification of a Putative G Protein . . . Cells," Cellular Immunology, 168:78–84 (1996).
Doranz et al., "A Dual–Tropic Primary . . . Cofactors," Cell, 85:1148–1158.
Dragic et al., "HIV–1 entry into CD4$^+$ cells . . . CC–CKR–5," Nature, 381:667–673 (1996).
Feng et al., "HIV–1 Entry Cofactor: Functional cDNA . . . Receptor," Science, 272:872–877 (1996).
Forster et al., "A Putative Chemokine Receptor . . . Spleen," Cell, 87:1037–1047.
M.L.X. Fu, "Characterization of anti–heart M2 muscarinic . . . study," Molecular and Cellular Biochemistry, 163/164:343–347 (1996).
Goga et al., "Alternative Signals to RAS for Hematopoietic . . . Oncogene," Cell, 82:981–988 (1995).
Hubank et al., "Identifying differences in mRNA expression . . . cDNA," Nucleic Acids Research, 22(25):5640–5648 (1994).
Koshiba et al., "Transient up–regulation of P2Y$_2$ nucleotide . . . thymocytes," Proc. Natl. Acad. Sci. USA, 94:831–836 (1997).
Kurzrock et al., "The Molecular Genetics of . . . Leukemias," The New England Journal of Medicine, 319(15):990–998 (1998).
Lugo et al., "The BCROABL Oncogene . . . v–myc," Molecular and Cellular Biology 9(3):1263–1270 (1989).
McLaughlin et al., "Alternative Forms of the . . . Cells," Molecular and Cellular Biology, 9(5):1866–1874 (1989).
Muller et al., "BCR First Exon Sequences . . . Leukemias," Molecular and Cellular Biology, 11(4):1785–1792 (1991).
P.M. Murphy, "The Molecular Biology . . . Receptors," Annu. Rev. Immunol., 12:593–633 (1994).
Pear et al., "Production of high–titer helper–free . . . transfection," Proc. Natl. Acad. Sci. USA 90:8392–8396 (1993).
Pendergast et al., "BCR–ABL–Induced Oncogenesis . . . Protein," Cell, 75:175–185 (1993).
Schneider et al., "Genes Specifically Expressed . . . Cells," Cell, 54:787–793 (1988).
Strader et al., "The family of G–protein–coupled receptors," The FASEB Journal, 9:745–754 (1995).
Strader et al., "Structure and Function of G Protein–Coupled Receptors," Annu. Rev. Biochem., 63:101–132 (1994).
Tsukada et al., "Deficient Expression of a . . . Agammaglobulinemia," Cell 72:279–290 (1993).
Lisitsyn et al., "Cloning the Differences Between . . . Genomes," Science 259:946–951 (1993).
Libert et al., "Selective Amplitication and Cloning . . . Family," Science, 244:569–572 (1989).
Bouvier et al., "Dynamic Palmitoylation of G–Protein . . . Cells," Methods in Enzymology, Academic Press, pp. 300–314 (1985).

*Primary Examiner*—Yvonne Eyler
*Assistant Examiner*—Nirmal S Basi
(74) *Attorney, Agent, or Firm*—Gates & Cooper LLP

(57) ABSTRACT

A G protien-coupled receptor (GPCR), called G2A, whose expression is regulated and functions at the G2/M checkpoint to ensure properly controlled duplication of hematopietic cells. The receptor is found predominantly in hematopietic cells and tissues and functions as a tumor suppressor gene, induces cell cycle arrest and integrates diverse signals by modulation of cytoskeletal architecture.

3 Claims, 27 Drawing Sheets

Alignment of Mouse and Human GPCRs

```
  1 MRSEPTNAAGNTTLGVTSVLQSTSVPSSETCHVSYEESRVVLVVVYSAVC        50 MOUSE
    | :.:.|.:.|           :||:::||:|:||||:|||||||||
  4 MLLKNGYNGNATPVTTAPWASLGLSAKTCNNVSFEESRIVLVVVYSAVC        53 HUMAN

51 LLGLPANCLTAWLTLLQVLQRNVLAVYLFCLSLCELLYISTVPLWIIYIQ       100 MOUSE
    |:|:||||||||||||.|||:||||||||||.|||:|||:|:|||||||.
 54 TLGVPANCLTAWLALLQVLQGNVLAVYLLCLALCELLYTGTLPLWVIYIR       103 HUMAN

101 NQHKWNLGPQACKVTAYIFFCNIYISILLCCISCDRYMAVVYALESRGH        150 MOUSE
    |||:|.|.|   |||||||||||:||||||||||||:||||||||||::
104 NQHRWTLGLLACKVTAYIFFCNIYVSILFLCCISCDRFVAVVYALESRGR       153 HUMAN

151 RHQRTAVTISACVILLVGLVNYPVFDMKVEKSFCFEPLRMNSKIAGYHYL       200 MOUSE
    | ::|| |||:||:::||:||:|:||   . :|. :|.:||||.:|||||
154 RRRRTAILISACIFILVGIVHYPVFQTE.DKETCFDMLQMDSRIAGYYYA       202 HUMAN

201 RFTFGFAIPLGILAFTNHQIFRSIKLSDSLSAAQKNKVKRSAIAVVTIFL       250 MOUSE
    |||.|||||| ||||||::||||||.|:.|:||.||:|||||||:|||||
203 RFTVGFAIPLSIIAFTNHRIFRSIKQSMGLSAAQKAKVKHSAIAVVIFL       252 HUMAN

251 VCFAPYHVLLVKAASFSFYQGDMDAVCAFESRLYTVSMVFLCLSTVNSV        300 MOUSE
    |||||||:||||||:|||||:|:|:||||:||||||:||||||||||:|
253 VCFAPYHLLLVKAAAFSYYRGDRNAMCGLEERLYTASVVFLCLSTVNGV       302 HUMAN

301 ADPIIYVLGTDHSRQEVSRIHTGWKKWSTKTYV...TCSKDSEETHLPTE      347 MOUSE
    |||||||:|:|||||||||||||:||:|.|.:.|.|.
303 ADPIIYVLATDHSRQEVSRIHKGWKEWSMKTDVTRLTHSRDTEELQSPVA      352 HUMAN

348 LSNTYTFPNPAHPPGSQPAKLGLLCSPERLPEELC  382 MOUSE
    |.||:||.:|.:|||||
353 LADHYTFSRPVHPPGSP......CPAKRLIEESC   380 HUMAN
```

FIG. 5

COUNTER-SELECTION OF G2A
IN TRANSFORMED PRE-B CELLS
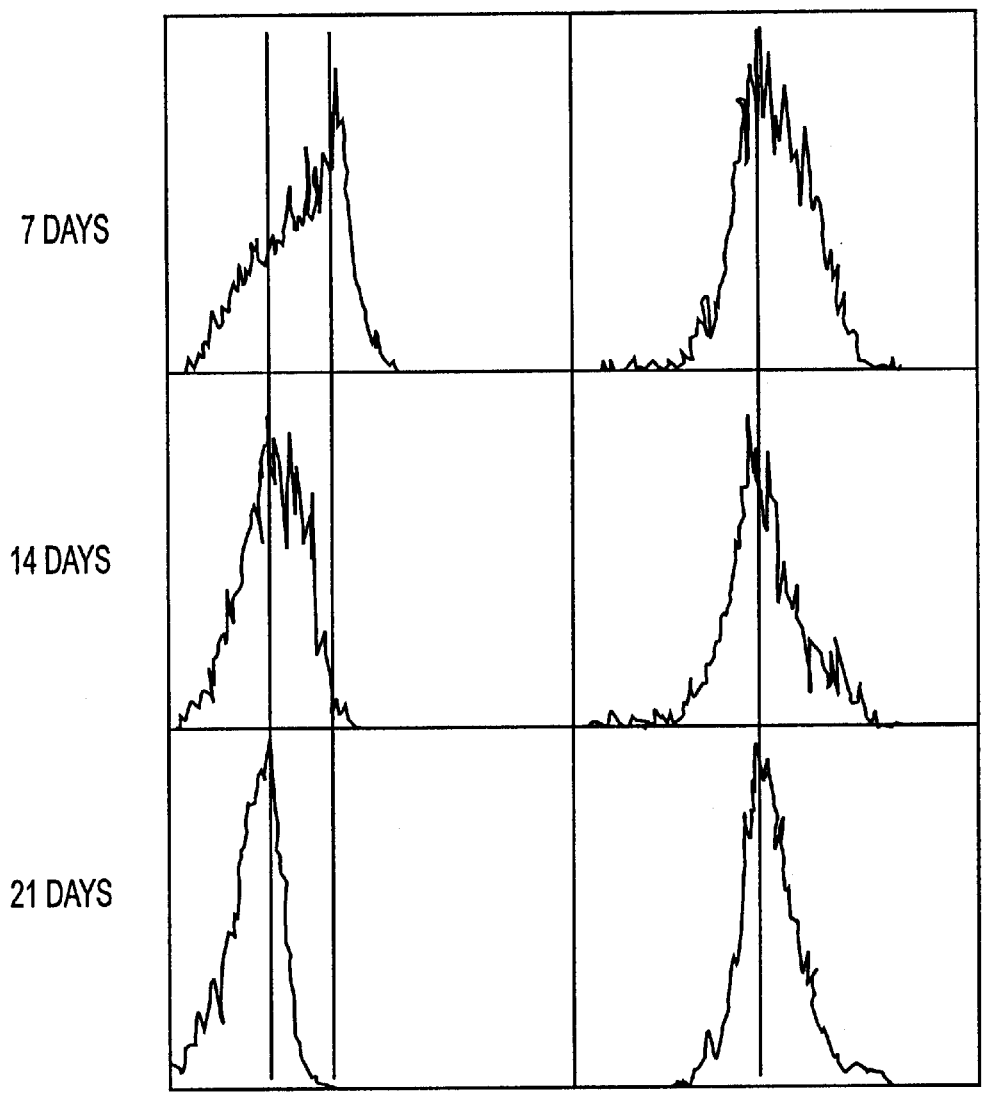
7 DAYS
14 DAYS
21 DAYS
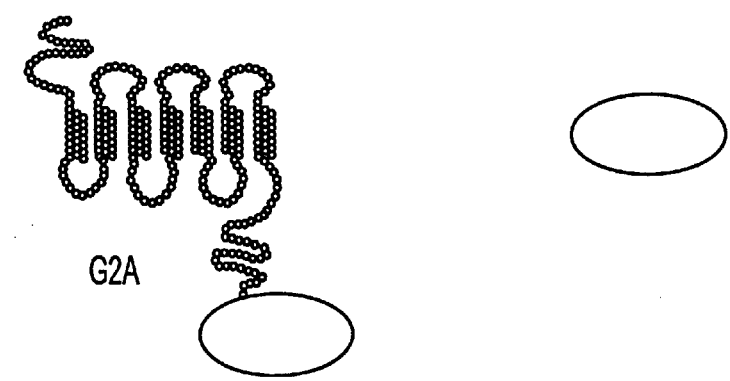
G2A
FIG. 8

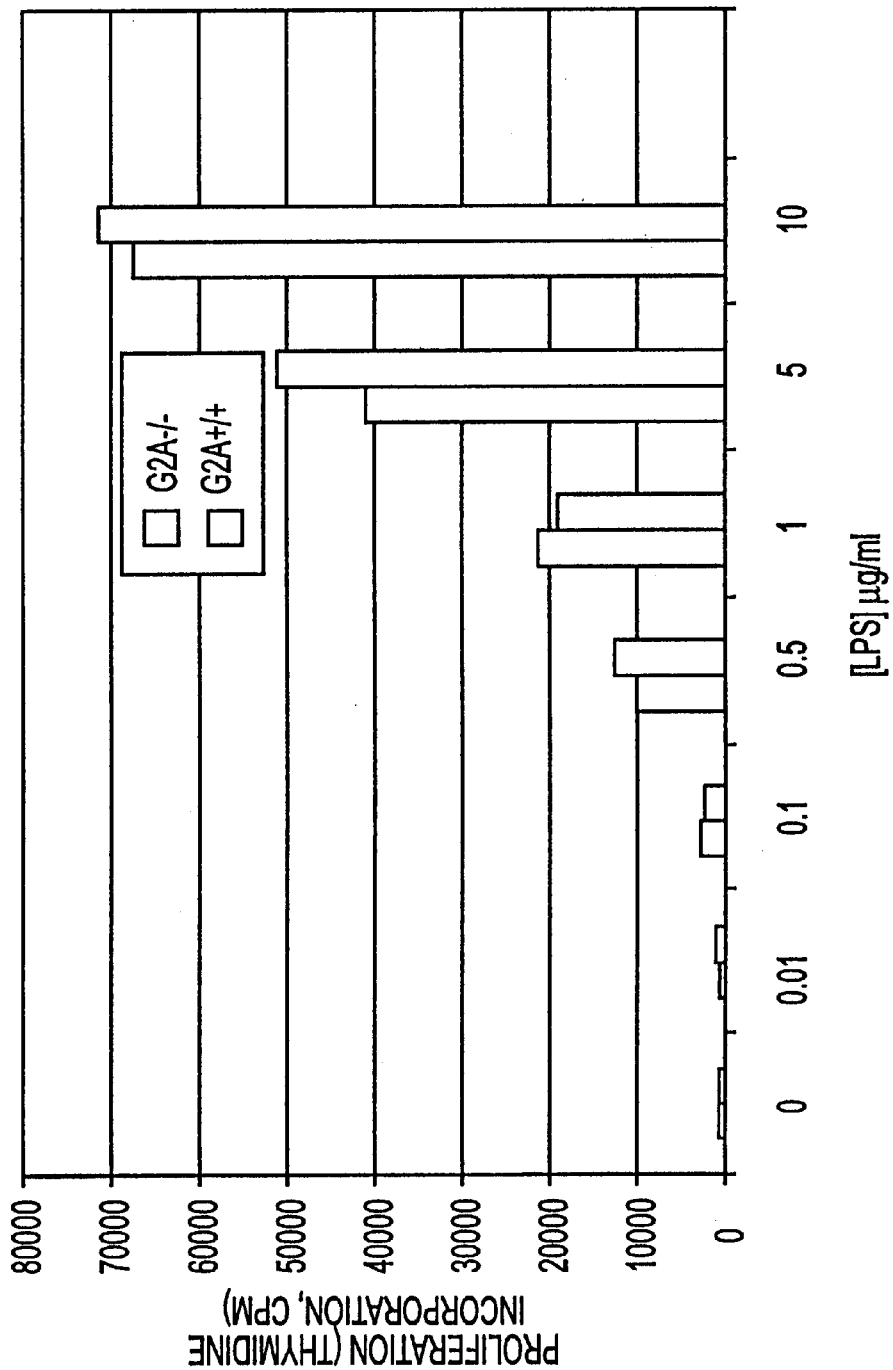

SEQUENCE LISTING (1) GENERAL INFORMATION:

(iii) NUMBER OF SEQUENCES: 40

(2) INFORMATION FOR SEQ ID NO: 1:

(i) SEQUENCE CHARACTERISTICS:
      (A) LENGTH: 1507 base pairs
      (B) TYPE: nucleic acid
      (C) STRANDEDNESS: single
      (D) TOPOLOGY: linear (ii) MOLECULE TYPE: cDNA (ix) FEATURE:
      (A) NAME/KEY: Coding Sequence
      (B) LOCATION: 147...1292
      (D) OTHER INFORMATION:

(xi) SEQUENCE DESCRIPTION: SEQ ID NO: 1:

```
AAACCTCCCA GCTGGGCCTG CAGAGGGGTG CTCAGCCCTG CCTCAGGACG GGCCTGCCCT      60

GTGCTGCCTC AGGACTGGCT TGGGTCATTT TAAGCTGCCA GAGCCACCTT CACAAGGGGG     120

TCCACAGAAC TCACATAGGA GCCACC ATG AGA TCA GAA CCT ACC AAT GCA GCA     173
                             Met Arg Ser Glu Pro Thr Asn Ala Ala
                              1               5

GGA AAC ACC ACA CTG GGG GTT ACC TCC GTT CTT CAG AGC ACC TCA GTA      221
Gly Asn Thr Thr Leu Gly Val Thr Ser Val Leu Gln Ser Thr Ser Val
 10              15                  20                  25
```

```
CCT TCT TCT GAG ACC TGC CAC GTC TCC TAC GAG GAG AGC AGA GTG GTC      269
Pro Ser Ser Glu Thr Cys His Val Ser Tyr Glu Glu Ser Arg Val Val
            30                  35                  40

CTG GTG GTG GTG TAC AGT GCC GTG TGC CTG CTG GGC CTA CCA GCC AAC      317
Leu Val Val Val Tyr Ser Ala Val Cys Leu Leu Gly Leu Pro Ala Asn
                45                  50                  55

TGC CTG ACT GCC TGG CTG ACG CTG CTG CAA GTC CTG CAG AGG AAC GTG      365
Cys Leu Thr Ala Trp Leu Thr Leu Leu Gln Val Leu Gln Arg Asn Val
        60                  65                  70

CTA GCC GTC TAC CTG TTC TGC CTG TCC CTC TGT GAG CTG CTC TAC ATC      413
Leu Ala Val Tyr Leu Phe Cys Leu Ser Leu Cys Glu Leu Leu Tyr Ile
    75                  80                  85

AGC ACG GTG CCA TTG TGG ATC ATC TAC ATC CAG AAT CAG CAC AAA TGG      461
Ser Thr Val Pro Leu Trp Ile Ile Tyr Ile Gln Asn Gln His Lys Trp
90                  95                 100                 105

AAC CTG GGT CCG CAG GCC TGC AAG GTG ACT GCT TAC ATC TTC TTC TGC      509
Asn Leu Gly Pro Gln Ala Cys Lys Val Thr Ala Tyr Ile Phe Phe Cys
                   110                 115                 120

AAC ATC TAC ATC AGC ATC CTC TTG CTC TGC TGC ATT TCC TGC GAC CGC      557
Asn Ile Tyr Ile Ser Ile Leu Leu Leu Cys Cys Ile Ser Cys Asp Arg
               125                 130                 135

TAC ATG GCC GTG GTC TAT GCA CTG GAG AGC CGA GGC CAC CGC CAC CAG      605
Tyr Met Ala Val Val Tyr Ala Leu Glu Ser Arg Gly His Arg His Gln
           140                 145                 150

AGG ACT GCT GTC ACC ATT TCT GCG TGT GTG ATT CTT CTT GTT GGA CTT      653
Arg Thr Ala Val Thr Ile Ser Ala Cys Val Ile Leu Leu Val Gly Leu
       155                 160                 165

GTT AAC TAT CCA GTG TTT GAC ATG AAG GTG GAG AAG AGT TTC TGC TTT      701
Val Asn Tyr Pro Val Phe Asp Met Lys Val Glu Lys Ser Phe Cys Phe
170                 175                 180                 185

GAG CCC CTG AGG ATG AAC AGC AAG ATA GCC GGC TAC CAC TAC CTG CGT      749
Glu Pro Leu Arg Met Asn Ser Lys Ile Ala Gly Tyr His Tyr Leu Arg
                   190                 195                 200

TTC ACC TTT GGC TTT GCC ATC CCT CTC GGC ATC CTG GCG TTC ACC AAT      797
Phe Thr Phe Gly Phe Ala Ile Pro Leu Gly Ile Leu Ala Phe Thr Asn
               205                 210                 215

CAC CAG ATC TTC CGG AGC ATC AAA CTC AGT GAC AGC CTG AGC GCT GCG      845
His Gln Ile Phe Arg Ser Ile Lys Leu Ser Asp Ser Leu Ser Ala Ala
           220                 225                 230

CAG AAG AAC AAG GTG AAG CGC TCC GCC ATC GCG GTC GTC ACC ATC TTC      893
Gln Lys Asn Lys Val Lys Arg Ser Ala Ile Ala Val Val Thr Ile Phe
       235                 240                 245

CTG GTC TGC TTT GCT CCC TAC CAC GTG GTA CTC CTC GTC AAA GCT GCC      941
Leu Val Cys Phe Ala Pro Tyr His Val Val Leu Leu Val Lys Ala Ala
250                 255                 260                 265

AGC TTT TCC TTC TAC CAA GGA GAC ATG GAT GCC GTG TGT GCC TTT GAA      989
Ser Phe Ser Phe Tyr Gln Gly Asp Met Asp Ala Val Cys Ala Phe Glu
                   270                 275                 280

AGC AGA CTG TAC ACA GTC TCT ATG GTG TTT CTG TGC CTG TCT ACA GTC     1037
Ser Arg Leu Tyr Thr Val Ser Met Val Phe Leu Cys Leu Ser Thr Val
               285                 290                 295

AAC AGT GTG GCT GAC CCC ATC ATC TAC GTG CTG GGT ACA GAC CAC TCT     1085
Asn Ser Val Ala Asp Pro Ile Ile Tyr Val Leu Gly Thr Asp His Ser
           300                 305                 310

CGG CAA GAA GTG TCC AGA ATC CAC ACA GGG TGG AAA AAG TGG TCC ACA     1133
Arg Gln Glu Val Ser Arg Ile His Thr Gly Trp Lys Lys Trp Ser Thr
       315                 320                 325

AAG ACA TAT GTT ACA TGC TCA AAG GAC TCT GAG GAG ACA CAC TTG CCC     1181
Lys Thr Tyr Val Thr Cys Ser Lys Asp Ser Glu Glu Thr His Leu Pro
330                 335                 340                 345
```

-continued

```
ACA GAG CTT TCA AAC ACA TAC ACC TTC CCC AAT CCC GCG CAC CCT CCA      1229
Thr Glu Leu Ser Asn Thr Tyr Thr Phe Pro Asn Pro Ala His Pro Pro
                350                 355                 360

GGA TCA CAG CCA GCG AAG CTA GGT TTA CTG TGC TCG CCA GAG AGA CTG      1277
Gly Ser Gln Pro Ala Lys Leu Gly Leu Leu Cys Ser Pro Glu Arg Leu
                365                 370                 375

CCT GAG GAG CTC TGC TAAGAGACGA TTGTCCACTC TTCCTCAAAA CTAGCACCAG T    1333
Pro Glu Glu Leu Cys
                380

CACACATACC TGGTCCTCTG AGTCACCGTC TGGGGTGTCC ACAGCACTAT AGATGCCTTT    1393

GTTCGGGCAC ACGCTGCTGA TCTTTCCTTC CTAAGGCCAC CAACTCTGAA AGTATCTGTT    1453

CCTTAAACTG TCCTCAGGCT CCCCTCTATG GAAAGCGGGG CTTGCTAAGG GACC          1507
```

(2) INFORMATION FOR SEQ ID NO: 2:

(i) SEQUENCE CHARACTERISTICS:
        (A) LENGTH: 382 amino acids
        (B) TYPE: amino acid
        (C) STRANDEDNESS: single
        (D) TOPOLOGY: linear (ii) MOLECULE TYPE: protein (v) FRAGMENT TYPE: internal (xi) SEQUENCE DESCRIPTION: SEQ ID NO: 2:

```
Met Arg Ser Glu Pro Thr Asn Ala Ala Gly Asn Thr Thr Leu Gly Val
 1               5                  10                  15

Thr Ser Val Leu Gln Ser Thr Ser Val Pro Ser Ser Glu Thr Cys His
                20                  25                  30

Val Ser Tyr Glu Glu Ser Arg Val Val Leu Val Val Val Tyr Ser Ala
            35                  40                  45

Val Cys Leu Leu Gly Leu Pro Ala Asn Cys Leu Thr Ala Trp Leu Thr
50                  55                  60

Leu Leu Gln Val Leu Gln Arg Asn Val Leu Ala Val Tyr Leu Phe Cys
65                  70                  75                  80

Leu Ser Leu Cys Glu Leu Leu Tyr Ile Ser Thr Val Pro Leu Trp Ile
                85                  90                  95

Ile Tyr Ile Gln Asn Gln His Lys Trp Asn Leu Gly Pro Gln Ala Cys
            100                 105                 110

Lys Val Thr Ala Tyr Ile Phe Phe Cys Asn Ile Tyr Ile Ser Ile Leu
            115                 120                 125

Leu Leu Cys Cys Ile Ser Cys Asp Arg Tyr Met Ala Val Val Tyr Ala
130                 135                 140

Leu Glu Ser Arg Gly His Arg His Gln Arg Thr Ala Val Thr Ile Ser
145                 150                 155                 160

Ala Cys Val Ile Leu Leu Val Gly Leu Val Asn Tyr Pro Val Phe Asp
                165                 170                 175

Met Lys Val Glu Lys Ser Phe Cys Phe Glu Pro Leu Arg Met Asn Ser
            180                 185                 190

Lys Ile Ala Gly Tyr His Tyr Leu Arg Phe Thr Phe Gly Phe Ala Ile
            195                 200                 205

Pro Leu Gly Ile Leu Ala Phe Thr Asn His Gln Ile Phe Arg Ser Ile
        210                 215                 220

Lys Leu Ser Asp Ser Leu Ser Ala Ala Gln Lys Asn Lys Val Lys Arg
225                 230                 235                 240
```

```
Ser Ala Ile Ala Val Val Thr Ile Phe Leu Val Cys Phe Ala Pro Tyr
                245                 250                 255

His Val Val Leu Leu Val Lys Ala Ala Ser Phe Ser Phe Tyr Gln Gly
                260                 265                 270

Asp Met Asp Ala Val Cys Ala Phe Glu Ser Arg Leu Tyr Thr Val Ser
                275                 280                 285

Met Val Phe Leu Cys Leu Ser Thr Val Asn Ser Val Ala Asp Pro Ile
                290                 295                 300

Ile Tyr Val Leu Gly Thr Asp His Ser Arg Gln Glu Val Ser Arg Ile
305                 310                 315                 320

His Thr Gly Trp Lys Lys Trp Ser Thr Lys Thr Tyr Val Thr Cys Ser
                325                 330                 335

Lys Asp Ser Glu Glu Thr His Leu Pro Thr Glu Leu Ser Asn Thr Tyr
                340                 345                 350

Thr Phe Pro Asn Pro Ala His Pro Pro Gly Ser Gln Pro Ala Lys Leu
                355                 360                 365

Gly Leu Leu Cys Ser Pro Glu Arg Leu Pro Glu Glu Leu Cys
                370                 375                 380

(2) INFORMATION FOR SEQ ID NO: 3:

(i) SEQUENCE CHARACTERISTICS:
        (A) LENGTH: 2938 base pairs
        (B) TYPE: nucleic acid
        (C) STRANDEDNESS: single
        (D) TOPOLOGY: linear (ii) MOLECULE TYPE: Other (ix) FEATURE:
        (A) NAME/KEY: Coding Sequence
        (B) LOCATION: 901...2040
        (D) OTHER INFORMATION:

(xi) SEQUENCE DESCRIPTION: SEQ ID NO: 3:

GGGAGGGGTG CNANGCTAGC CACGCAGGCG GGGCCCTGGG TCATTTTAAN CTCTCAGAGT      60

GAACGTCTTG ATAGGACCGA CAANACNCAT NACNTGTACT TAGATAGCTT ATCTTANANC     120

CACNCTGANA TTGGAACCCG CAAAATATGC CNGGGAGGAA GGTGAGCAAG GACACGACA      180

CTCACCCGGA TAAACCCAAC AAGCGCAGCG AGGCTGTGGG GAAACCGGAN CCCTGCACAC     240

CGCCGGGGGA AGGTGGGCCN CCGCCACCAC CGTGGAAGAA CAGCGCGGAN GCACCCCACG     300

AGATGAGACG GAACTGCCGT GAGATCCAGC AATNCCNACT GTGGGTCTGA CCCAGGATAN     360

CGGAAAGCAG GGACGTGAAC AGCCCTCCTC ATGTTCTTGA CACCGTCATT CTCAGCAGCT     420

CAGCTAAGGC ACAGAGGCAG CCGAGCGTCT GTCAGCAGAG TCGTGGCTGA GCAGAACACG     480

CCACACGCCA CACGCCACAC GCCACACGTG CAGGATTGCT CAAGATGGAA GGCACAGTG      540

GAATATATAT ATATATTTAT ATTTTTGGCG AGACCCTGGA GGACACACTG AATACAATGG     600

AATACCATCC CGCCTTTGAA AGGAAGGGAA ATCCTGGCAC ACGCTGCAAC AGGAGGGACG     660

TTGAGGACAC TGTGGTGAGT GGAGCACGTG AGACACGGAA GGACACACGC TGAAGACAGG     720

CAGAGATGCC CACCCACGTG GGGAGGTGAC AGGGGAGCCC AGCGCACAGA GACAAAGTGG     780

AATGGAGGCC TGGGGCTGGG GAGCAAATGC GGAGCGAGTG CTTCCTGGGG CAGAGTCTCC     840

GTTTGGGAAG ATGAGAAGGT TCTGCCGACG GATGCTGGCG ATGGTTGCAG AAGAATGTGC     900

ATG TGC CCA ATG CTA CTG AAA AAC GGT TAC AAT GGA AAC GCC ACC CCA       948
Met Cys Pro Met Leu Leu Lys Asn Gly Tyr Asn Gly Asn Ala Thr Pro
 1               5                  10                  15
```

```
GTG ACC ACC ACT GCC CCG TGG GCC TCC CTG GGC CTC TCC GCC AAG ACC        996
Val Thr Thr Thr Ala Pro Trp Ala Ser Leu Gly Leu Ser Ala Lys Thr
             20                  25                  30

TGC AAC AAC GTG TCC TTC GAA GAG AGC AGG ATA GTC CTG GTC GTG GTG       1044
Cys Asn Asn Val Ser Phe Glu Glu Ser Arg Ile Val Leu Val Val Val
         35                  40                  45

TAC AGC GCG GTG TGC ACG CTG GGG GTG CCG GCC AAC TGC CTG ACT GCG       1092
Tyr Ser Ala Val Cys Thr Leu Gly Val Pro Ala Asn Cys Leu Thr Ala
     50                  55                  60

TGG CTG GCG CTG CTG CAG GTA CTG CAG GGC AAC GTG CTG GCC GTC TAC       1140
Trp Leu Ala Leu Leu Gln Val Leu Gln Gly Asn Val Leu Ala Val Tyr
 65                  70                  75                  80

CTG CTC TGC CTG GCA CTC TGC GAG CTG CTG TAC ACA GGC ACG CTG CCA       1188
Leu Leu Cys Leu Ala Leu Cys Glu Leu Leu Tyr Thr Gly Thr Leu Pro
                 85                  90                  95

CTC TGG GTC ATC TAT ATC CGC AAC CAG CAC CGC TGG ACC CTA GGC CTG       1236
Leu Trp Val Ile Tyr Ile Arg Asn Gln His Arg Trp Thr Leu Gly Leu
            100                 105                 110

CTG GCC TGC AAG GTG ACC GCC TAC ATC TTC TTC TGC AAC ATC TAC GTC       1284
Leu Ala Cys Lys Val Thr Ala Tyr Ile Phe Phe Cys Asn Ile Tyr Val
        115                 120                 125

AGC ATC CTC TTC CTG TGC TGC ATC TCC TGC GAC CGC TTC GTG GCC GTC       1332
Ser Ile Leu Phe Leu Cys Cys Ile Ser Cys Asp Arg Phe Val Ala Val
    130                 135                 140

GTG TAC GCG CTG GAG AGT CGG GGC CGC CGC CGC CGG AGG ACC GCC ATC       1380
Val Tyr Ala Leu Glu Ser Arg Gly Arg Arg Arg Arg Arg Thr Ala Ile
145                 150                 155                 160

CTC ATC TCC GCC TGC ATC TTC ATC CTC GTC GGG ATC GTT CAC TAC CCG       1428
Leu Ile Ser Ala Cys Ile Phe Ile Leu Val Gly Ile Val His Tyr Pro
                165                 170                 175

GTG TTC CAG ACG GAA GAC AAG GAG ACC TGC TTT GAC ATG CTG CAG ATG       1476
Val Phe Gln Thr Glu Asp Lys Glu Thr Cys Phe Asp Met Leu Gln Met
            180                 185                 190

GAC AGC AGG ATT GCC GGG TAC TAC TAC GCC AGG TTC ACC GTT GGC TTT       1524
Asp Ser Arg Ile Ala Gly Tyr Tyr Tyr Ala Arg Phe Thr Val Gly Phe
        195                 200                 205

GCC ATC CCT CTC TCC ATC ATC GCC TTC ACC AAC CAC CGG ATT TTC AGG       1572
Ala Ile Pro Leu Ser Ile Ile Ala Phe Thr Asn His Arg Ile Phe Arg
    210                 215                 220

AGC ATC AAG CAG AGC ATG GGC TTA AGC GCT GCC CAG AAG GCC AAG GTG       1620
Ser Ile Lys Gln Ser Met Gly Leu Ser Ala Ala Gln Lys Ala Lys Val
225                 230                 235                 240

AAG CAC TCG GCC ATC GCG GTG GTT GTC ATC TTC CTA GTC TGC TTC GCC       1668
Lys His Ser Ala Ile Ala Val Val Val Ile Phe Leu Val Cys Phe Ala
                245                 250                 255

CCG TAC CAC CTG GTT CTC CTC GTC AAA GCC GCT GCC TTT TCC TAC TAC       1716
Pro Tyr His Leu Val Leu Leu Val Lys Ala Ala Ala Phe Ser Tyr Tyr
            260                 265                 270

AGA GGA GAC AGG AAC GCC ATG TGC GGC TTG GAG GAA AGG CTG TAC ACA       1764
Arg Gly Asp Arg Asn Ala Met Cys Gly Leu Glu Glu Arg Leu Tyr Thr
        275                 280                 285

GCC TCT GTG GTG TTT CTG TGC CTG TCC ACG GTG AAC GGC GTG GCT GAC       1812
Ala Ser Val Val Phe Leu Cys Leu Ser Thr Val Asn Gly Val Ala Asp
    290                 295                 300

CCC ATT ATC TAC GTG CTG GCC ACG GAC CAT TCC CGC CAA GAA GTG TCC       1860
Pro Ile Ile Tyr Val Leu Ala Thr Asp His Ser Arg Gln Glu Val Ser
305                 310                 315                 320

AGA ATC CAT AAG GGG TGG AAA GAG TGG TCC ATG AAG ACA GAC GTC ACC       1908
Arg Ile His Lys Gly Trp Lys Glu Trp Ser Met Lys Thr Asp Val Thr
                325                 330                 335
```

```
AGG CTC ACC CAC AGC AGG GAC ACC GAG GAG CTG CAG TCG CCC GTG GCC      1956
Arg Leu Thr His Ser Arg Asp Thr Glu Glu Leu Gln Ser Pro Val Ala
            340                 345                 350

CTT GCA GAC CAC TAC ACC TTC TCC AGG CCC GTG CAC CCA CCA GGG TCA      2004
Leu Ala Asp His Tyr Thr Phe Ser Arg Pro Val His Pro Pro Gly Ser
            355                 360                 365

CCA TGC CCT GCA AAG AGG CTG ATT GAG GAG TCC TGC TGAGCCCACT GTGTGG    2056
Pro Cys Pro Ala Lys Arg Leu Ile Glu Glu Ser Cys
        370                 375                 380

CAGGGGGATG GCAGGTTGGG GGTCCTGGGG CCAGCAATGT GGTTCCTGTG CACTGAGCCC    2116

ACCAGCCACA GTGCCCATGT CCCCTCTGGA AGACAAACTA CCAATTTCTC GTTCCTGAAG    2176

CCACTCCCTC CGTGACCACT GGCCCCANGC TTTCCCACAT GGAAGGTGGC TGCATGCCAA    2236

GGGGAAGAAC GACACCTCCA GGCTTCCGGG AGCCCANANA NCATGTGGCA NGCAGTGGGG    2296

CCTCTTCATC ATCANCCTGC CTGGCTGGCT CCCTTGGCTG TGGGCANGTA CACCCCTGCT    2356

GGCANAAGTA CCTGGTGGCT GCCCTGTTCG CATCANTGGC GATNACTTTA TTTGCGGAGC    2416

ATTTCTGCAA NCGTTGCCTG GATNCGGTGG TGCATTGTGG GCCCTCTGGG CTCCTGCCTC    2476

AAAATGTCAG TGANCACCAT GCTGGAAGTC ACCATCACTG TGGCANCGCC CANGAAGCTG    2536

TANGGCACCT ACCACCTCCA ANGGGGCANG CGCCCTCATC TGGGGTTGGG TCTNTTGCTG    2596

AACTGGGAAG GCCTCTANGG GAACCCTGGG GCANGGTGGC CAACTGCTNG CTCCCANAAA    2656

CCAACCCAAG GCGTCTCAAC GGGGGAACCC CAAATGTTCN CGCCCCANAA AAAACAATTT    2716

TNGGAAGGAN AAGTTNTTAA ACACCCCNCC NCCANAAGCC AAGGGGTTCC CAGGAAATTC    2776

CCCACCGGCA TCCTCCGGGG AAAANACTCG GTNAANGGGT CCCTTACAAG GGTTGGGGGT    2836

TCCCCNCCCC TAACCCCCNT TAATTGAAGG GGGGGAAATT CAACCCTTTT GGCCTCCTTT    2896

TTTTTTGCGG NAAAAAAAAC AACNTCCCCT GCANCCCCCG GN                      2938

(2) INFORMATION FOR SEQ ID NO: 4:

(i) SEQUENCE CHARACTERISTICS:
        (A) LENGTH: 380 amino acids
        (B) TYPE: amino acid
        (C) STRANDEDNESS: single
        (D) TOPOLOGY: linear (ii) MOLECULE TYPE: protein (v) FRAGMENT TYPE: internal (xi) SEQUENCE DESCRIPTION: SEQ ID NO: 4:

Met Cys Pro Met Leu Leu Lys Asn Gly Tyr Asn Gly Asn Ala Thr Pro
1               5                   10                  15

Val Thr Thr Thr Ala Pro Trp Ala Ser Leu Gly Leu Ser Ala Lys Thr
            20                  25                  30

Cys Asn Asn Val Ser Phe Glu Glu Ser Arg Ile Val Leu Val Val Val
        35                  40                  45

Tyr Ser Ala Val Cys Thr Leu Gly Val Pro Ala Asn Cys Leu Thr Ala
    50                  55                  60

Trp Leu Ala Leu Leu Gln Val Leu Gln Gly Asn Val Leu Ala Val Tyr
65                  70                  75                  80

Leu Leu Cys Leu Ala Leu Cys Glu Leu Leu Tyr Thr Gly Thr Leu Pro
                85                  90                  95

Leu Trp Val Ile Tyr Ile Arg Asn Gln His Arg Trp Thr Leu Gly Leu
                100                 105                 110
```

```
Leu Ala Cys Lys Val Thr Ala Tyr Ile Phe Phe Cys Asn Ile Tyr Val
        115                 120                 125

Ser Ile Leu Phe Leu Cys Cys Ile Ser Cys Asp Arg Phe Val Ala Val
130                 135                 140

Val Tyr Ala Leu Glu Ser Arg Gly Arg Arg Arg Arg Thr Ala Ile
145                 150                 155                 160

Leu Ile Ser Ala Cys Ile Phe Ile Leu Val Gly Ile Val His Tyr Pro
                165                 170                 175

Val Phe Gln Thr Glu Asp Lys Glu Thr Cys Phe Asp Met Leu Gln Met
                180                 185                 190

Asp Ser Arg Ile Ala Gly Tyr Tyr Tyr Ala Arg Phe Thr Val Gly Phe
                195                 200                 205

Ala Ile Pro Leu Ser Ile Ile Ala Phe Thr Asn His Arg Ile Phe Arg
        210                 215                 220

Ser Ile Lys Gln Ser Met Gly Leu Ser Ala Ala Gln Lys Ala Lys Val
225                 230                 235                 240

Lys His Ser Ala Ile Ala Val Val Ile Phe Leu Val Cys Phe Ala
                245                 250                 255

Pro Tyr His Leu Val Leu Leu Val Lys Ala Ala Ala Phe Ser Tyr Tyr
                260                 265                 270

Arg Gly Asp Arg Asn Ala Met Cys Gly Leu Glu Glu Arg Leu Tyr Thr
                275                 280                 285

Ala Ser Val Val Phe Leu Cys Leu Ser Thr Val Asn Gly Val Ala Asp
290                 295                 300

Pro Ile Ile Tyr Val Leu Ala Thr Asp His Ser Arg Gln Glu Val Ser
305                 310                 315                 320

Arg Ile His Lys Gly Trp Lys Glu Trp Ser Met Lys Thr Asp Val Thr
                325                 330                 335

Arg Leu Thr His Ser Arg Asp Thr Glu Glu Leu Gln Ser Pro Val Ala
                340                 345                 350

Leu Ala Asp His Tyr Thr Phe Ser Arg Pro Val His Pro Pro Gly Ser
                355                 360                 365

Pro Cys Pro Ala Lys Arg Leu Ile Glu Glu Ser Cys
370                 375                 380

(2) INFORMATION FOR SEQ ID NO: 5:

(i) SEQUENCE CHARACTERISTICS:
        (A) LENGTH: 13 amino acids
        (B) TYPE: amino acid
        (C) STRANDEDNESS: single
        (D) TOPOLOGY: linear (ii) MOLECULE TYPE: protein (xi) SEQUENCE DESCRIPTION: SEQ ID NO: 5:

Lys Asp Ser Glu Glu Thr His Leu Pro Thr Glu Leu Ser
1               5                   10

(2) INFORMATION FOR SEQ ID NO: 6:

(i) SEQUENCE CHARACTERISTICS:
        (A) LENGTH: 24 base pairs
        (B) TYPE: nucleic acid
        (C) STRANDEDNESS: single
        (D) TOPOLOGY: linear (xi) SEQUENCE DESCRIPTION: SEQ ID NO: 6:

AGCACTCTCC AGCCTCTCAC CGCA                                              24
```

(2) INFORMATION FOR SEQ ID NO: 7:

(i) SEQUENCE CHARACTERISTICS:
        (A) LENGTH: 24 base pairs
        (B) TYPE: nucleic acid
        (C) STRANDEDNESS: single
        (D) TOPOLOGY: linear (xi) SEQUENCE DESCRIPTION: SEQ ID NO: 7:

ACCGACGTCG ACTATCCATG AACA                                    24

(2) INFORMATION FOR SEQ ID NO: 8:

(i) SEQUENCE CHARACTERISTICS:
        (A) LENGTH: 24 base pairs
        (B) TYPE: nucleic acid
        (C) STRANDEDNESS: single
        (D) TOPOLOGY: linear (xi) SEQUENCE DESCRIPTION: SEQ ID NO: 8:

AGGCAACTGT GCTATCCGAG GGAA                                    24

(2) INFORMATION FOR SEQ ID NO: 9:

(i) SEQUENCE CHARACTERISTICS:
        (A) LENGTH: 12 base pairs
        (B) TYPE: nucleic acid
        (C) STRANDEDNESS: single
        (D) TOPOLOGY: linear (xi) SEQUENCE DESCRIPTION: SEQ ID NO: 9:

GATCTGCGGT GA                                                                12

(2) INFORMATION FOR SEQ ID NO: 10:

(i) SEQUENCE CHARACTERISTICS:
        (A) LENGTH: 12 base pairs
        (B) TYPE: nucleic acid
        (C) STRANDEDNESS: single
        (D) TOPOLOGY: linear (xi) SEQUENCE DESCRIPTION: SEQ ID NO: 10:

GATCTGTTCA TG                                                                 12

(2) INFORMATION FOR SEQ ID NO: 11:

(i) SEQUENCE CHARACTERISTICS:
        (A) LENGTH: 12 base pairs
        (B) TYPE: nucleic acid
        (C) STRANDEDNESS: single
        (D) TOPOLOGY: linear (xi) SEQUENCE DESCRIPTION: SEQ ID NO: 11:

GATCTTCCCT CG                                                                 12

(2) INFORMATION FOR SEQ ID NO: 12:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (xi) SEQUENCE DESCRIPTION: SEQ ID NO: 12:

CAGGACTGGC TTGGGTCATT                                          20

(2) INFORMATION FOR SEQ ID NO: 13:

(i) SEQUENCE CHARACTERISTICS:
        (A) LENGTH: 21 base pairs
        (B) TYPE: nucleic acid
        (C) STRANDEDNESS: single
        (D) TOPOLOGY: linear (xi) SEQUENCE DESCRIPTION: SEQ ID NO: 13:

```
GTCCACAGAA CTCACATAGG A                                              21
```

(2) INFORMATION FOR SEQ ID NO: 14:

(i) SEQUENCE CHARACTERISTICS:
        (A) LENGTH: 39 base pairs
        (B) TYPE: nucleic acid
        (C) STRANDEDNESS: single
        (D) TOPOLOGY: linear (xi) SEQUENCE DESCRIPTION: SEQ ID NO: 14:

```
CGCGGATCCG AATTCGGTAC CGGTGACTCA GAGGACCAG                            39
```

(2) INFORMATION FOR SEQ ID NO: 15:

(i) SEQUENCE CHARACTERISTICS:
        (A) LENGTH: 34 base pairs
        (B) TYPE: nucleic acid
        (C) STRANDEDNESS: single
        (D) TOPOLOGY: linear (xi) SEQUENCE DESCRIPTION: SEQ ID NO: 15:

```
CGGAATTCTC GAGTCAGGAC TGGCTTGGGT CATT                                 34
```

(2) INFORMATION FOR SEQ ID NO: 16:

(i) SEQUENCE CHARACTERISTICS:
        (A) LENGTH: 35 base pairs
        (B) TYPE: nucleic acid
        (C) STRANDEDNESS: single
        (D) TOPOLOGY: linear (xi) SEQUENCE DESCRIPTION: SEQ ID NO: 16:

```
ATAGTTTAGC GGCCGCGCAG AGCTCCTCAG GCAGT                                35
```

(2) INFORMATION FOR SEQ ID NO: 17:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (xi) SEQUENCE DESCRIPTION: SEQ ID NO: 17:

```
CAAGAAGTGT CCAGAATCCA                                                 20
```

(2) INFORMATION FOR SEQ ID NO: 18:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (xi) SEQUENCE DESCRIPTION: SEQ ID NO: 18:

```
GGTGACAGCA GTCCTCTGGT                                                 20
```

(2) INFORMATION FOR SEQ ID NO: 19:

(i) SEQUENCE CHARACTERISTICS:
        (A) LENGTH: 21 base pairs
        (B) TYPE: nucleic acid
        (C) STRANDEDNESS: single
        (D) TOPOLOGY: linear (xi) SEQUENCE DESCRIPTION: SEQ ID NO: 19:

TAGCGGTCGC AGGAAATGCA G                                                21

(2) INFORMATION FOR SEQ ID NO: 20:

(i) SEQUENCE CHARACTERISTICS:
        (A) LENGTH: 18 base pairs
        (B) TYPE: nucleic acid
        (C) STRANDEDNESS: single
        (D) TOPOLOGY: linear (xi) SEQUENCE DESCRIPTION: SEQ ID NO: 20:

TGATTGGTGA ACGCCAGG                                                  18

(2) INFORMATION FOR SEQ ID NO: 21:

(i) SEQUENCE CHARACTERISTICS:
        (A) LENGTH: 22 base pairs
        (B) TYPE: nucleic acid
        (C) STRANDEDNESS: single
        (D) TOPOLOGY: linear (xi) SEQUENCE DESCRIPTION: SEQ ID NO: 21:

GCTTTGAGCC CCTGAGGATG AA                                          22

(2) INFORMATION FOR SEQ ID NO: 22:

(i) SEQUENCE CHARACTERISTICS:
        (A) LENGTH: 22 base pairs
        (B) TYPE: nucleic acid
        (C) STRANDEDNESS: single
        (D) TOPOLOGY: linear (xi) SEQUENCE DESCRIPTION: SEQ ID NO: 22:

GTAATACGAC TCACTATAGG GC                                          22

(2) INFORMATION FOR SEQ ID NO: 23:

(i) SEQUENCE CHARACTERISTICS:
        (A) LENGTH: 30 base pairs
        (B) TYPE: nucleic acid
        (C) STRANDEDNESS: single
        (D) TOPOLOGY: linear (xi) SEQUENCE DESCRIPTION: SEQ ID NO: 23:

GTCGGATCCA TGAGATCAGA ACCTACCAAT                            30

(2) INFORMATION FOR SEQ ID NO: 24:

(i) SEQUENCE CHARACTERISTICS:
        (A) LENGTH: 30 base pairs
        (B) TYPE: nucleic acid
        (C) STRANDEDNESS: single
        (D) TOPOLOGY: linear (xi) SEQUENCE DESCRIPTION: SEQ ID NO: 24:

GTCGAATTCT CACAGGACCA CTCTGCTCTC                            30

(2) INFORMATION FOR SEQ ID NO: 25:

```
    (i) SEQUENCE CHARACTERISTICS:
        (A) LENGTH: 17 base pairs
        (B) TYPE: nucleic acid
        (C) STRANDEDNESS: single
        (D) TOPOLOGY: linear (xi) SEQUENCE DESCRIPTION: SEQ ID NO: 25:

CAGGAAACAG CTATGAC                                                      17

(2) INFORMATION FOR SEQ ID NO: 26:

(i) SEQUENCE CHARACTERISTICS:
        (A) LENGTH: 42 base pairs
        (B) TYPE: nucleic acid
        (C) STRANDEDNESS: single
        (D) TOPOLOGY: linear (xi) SEQUENCE DESCRIPTION: SEQ ID NO: 26:

CUACUACUAC UAGGCCACGC GTCGACTAGT ACGGGGGGGG GG                           42

(2) INFORMATION FOR SEQ ID NO: 27:

(i) SEQUENCE CHARACTERISTICS:
        (A) LENGTH: 21 base pairs
        (B) TYPE: nucleic acid
        (C) STRANDEDNESS: single
        (D) TOPOLOGY: linear (xi) SEQUENCE DESCRIPTION: SEQ ID NO: 27:

GCCGAATTCT CAAACTCCGG C                                                 21

(2) INFORMATION FOR SEQ ID NO: 28:

(i) SEQUENCE CHARACTERISTICS:
        (A) LENGTH: 64 base pairs
        (B) TYPE: nucleic acid
        (C) STRANDEDNESS: single
        (D) TOPOLOGY: linear (xi) SEQUENCE DESCRIPTION: SEQ ID NO: 28:

CCGGAATTCG GCCACCATGG ACTACAAGGA CGACGATGAC AAGAGATCAG AACCTACCA        60

TGCA                                                                    64

(2) INFORMATION FOR SEQ ID NO: 29:

(i) SEQUENCE CHARACTERISTICS:
        (A) LENGTH: 42 base pairs
        (B) TYPE: nucleic acid
        (C) STRANDEDNESS: single
        (D) TOPOLOGY: linear (xi) SEQUENCE DESCRIPTION: SEQ ID NO: 29:

CCGGAATTCC TAGAGGCCAC CATGAGATCA GAACCTACCA AT                          42

(2) INFORMATION FOR SEQ ID NO: 30:

(i) SEQUENCE CHARACTERISTICS:
        (A) LENGTH: 29 base pairs
        (B) TYPE: nucleic acid
        (C) STRANDEDNESS: single
        (D) TOPOLOGY: linear (xi) SEQUENCE DESCRIPTION: SEQ ID NO: 30:

CGCTCGAGTG GGAGCAAATG CGGAGCGAG                                         29
```

(2) INFORMATION FOR SEQ ID NO: 31:

(i) SEQUENCE CHARACTERISTICS:
        (A) LENGTH: 32 base pairs
        (B) TYPE: nucleic acid
        (C) STRANDEDNESS: single
        (D) TOPOLOGY: linear (xi) SEQUENCE DESCRIPTION: SEQ ID NO: 31:

TTAGCGGCCG CTCAGCAGGA CTCCTCAATC AG                                        32

(2) INFORMATION FOR SEQ ID NO: 32:

(i) SEQUENCE CHARACTERISTICS:
        (A) LENGTH: 33 base pairs
        (B) TYPE: nucleic acid
        (C) STRANDEDNESS: single
        (D) TOPOLOGY: linear (xi) SEQUENCE DESCRIPTION: SEQ ID NO: 32:

TTAGCGGCCG CGCAGGACTC CTCAATCAGC CTC                                      33

(2) INFORMATION FOR SEQ ID NO: 33:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (xi) SEQUENCE DESCRIPTION: SEQ ID NO: 33:

CAAGAAGTGT CCAGAATCCA                                                        20

(2) INFORMATION FOR SEQ ID NO: 34:

(i) SEQUENCE CHARACTERISTICS:
        (A) LENGTH: 19 base pairs
        (B) TYPE: nucleic acid
        (C) STRANDEDNESS: single
        (D) TOPOLOGY: linear (xi) SEQUENCE DESCRIPTION: SEQ ID NO: 34:

ACCAGCCACA GTGCCCATG                                                         19

(2) INFORMATION FOR SEQ ID NO: 35:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (xi) SEQUENCE DESCRIPTION: SEQ ID NO: 35:

TGCCACTCTG GGTCATCTAT                                                      20

(2) INFORMATION FOR SEQ ID NO: 36:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (xi) SEQUENCE DESCRIPTION: SEQ ID NO: 36:

CGGTGGTTGT CATCTTCCTA                                                      20

(2) INFORMATION FOR SEQ ID NO: 37:

(i) SEQUENCE CHARACTERISTICS:
    (A) LENGTH: 22 base pairs
    (B) TYPE: nucleic acid
    (C) STRANDEDNESS: single
    (D) TOPOLOGY: linear (xi) SEQUENCE DESCRIPTION: SEQ ID NO: 37:

GTAATACGAC TCACTATAGG GC                            22

(2) INFORMATION FOR SEQ ID NO: 38:

(i) SEQUENCE CHARACTERISTICS:
        (A) LENGTH: 17 base pairs
        (B) TYPE: nucleic acid
        (C) STRANDEDNESS: single
        (D) TOPOLOGY: linear (xi) SEQUENCE DESCRIPTION: SEQ ID NO: 38:

CAGGAAACAG CTATGAC                                  17

(2) INFORMATION FOR SEQ ID NO: 39:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (xi) SEQUENCE DESCRIPTION: SEQ ID NO: 39:

ACCACAGTCC ATGCCATCAC                               20

(2) INFORMATION FOR SEQ ID NO: 40:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (xi) SEQUENCE DESCRIPTION: SEQ ID NO: 40:

TCCACCACCC TGTTGCTGTA                               20

TRANSCRIPTIONALLY REGULATED G PROTEIN-COUPLED RECEPTOR G2A

RELATED APPLICATIONS

This present application is a continuation-in-part of U.S. patent application Ser. No. 09/120,025, filed Jul. 17, 1998, now U.S. Pat. No. 6,214,562, which is a continuation-in-part of U.S. patent application Ser. No. 08/969,815, filed on Nov. 13, 1997, now U.S. Pat. No. 6,207,412.

FIELD OF THE INVENTION

The present invention relates to a G protein-coupled receptor which is expressed predominantly in lymphoid cells, is transcriptionally induced in response to proliferative stimuli and genotoxic treatment and integrates diverse cellular signals by modulation of cytoskeletal architecture.

BACKGROUND OF THE INVENTION

The family of G protein-coupled receptors (GPCRs) has at least 250 members (Strader et al. *FASEB J.*, 9:745–754, 1995; Strader et al. *Annu. Rev. Biochem.*, 63:101–32, 1994). It has been estimated that one percent of human genes may encode GPCRs. GPCRs bind to a wide-variety of ligands ranging from photons, small biogenic amines (i.e., epinephrine and histamine), peptides (i.e., IL-8), to large glycoprotein hormones (i.e., parathyroid hormone). GPCRs play important roles in diverse cellular processes including cell proliferation and differentiation, leukocyte migration in response to inflammation, and cellular response to light, odorants, neurotransmitters and hormones (Strader et al., supra.).

Ligand binding to GPCRs elicits activation of signaling pathways via associated heterotrimeric G proteins comprising $\alpha$, $\beta$ and $\gamma$ subunits. Heterotrimeric G proteins are classified according to the $\alpha$ subunit, which can be any of more than 20 grouped into 4 classes termed $G_s$, $G_i$, $G_q$ and $G_{12}$. Similarly, there are 6 known $\beta$ and 12 $\gamma$ subunits, further increasing the complexity, although not all possible combinations are functional (Schmidt et al., *J. Biol. Chem.* 267:13807–13810, 1992). Initiation of signal transduction follows exchange of GTP for GDP bound to the $\alpha$-subunit and its dissociation from the $\beta\gamma$ dimer. Both released GTP-bound $\alpha$ and free $\beta\gamma$ components are capable of mediating signaling events through their interaction with effector molecules, leading to an appropriate physiological response. Importantly, activation of G protein signaling is integrated with receptor downregulation via serine/threonine phosphorylation of critical residues within the carboxy terminal cytoplasmic tail of the GPCR by GPCR kinases (GRKs) as well as Protein Kinase A (PKA) and Protein Kinase C (PKC) leading to desensitization and internalization of the receptor (Ferguson et al., *Biochem. Soc. Trans.* 24:953–959, 1996).

A growing number of GPCRs with ligand independent activity exist whose biological function is most likely regulated at the transcriptional level (Leurs et al., *Trends Biochem. Sci.* 23:418–422, 1998). While members of this class of GPCR are also subject to phosphorylation dependent downmodulation, transcriptional control of receptor number confers a high degree of temporal control over receptor turnover and activity.

Multiple GPCRs in a given cell-type can couple to the same G protein and a variety of accessory molecules exist which can modify both the responsiveness of GPCRs to effector signals (McLatchie et al., *Nature* 393:333–339, 1998) as well as integrating GTP exchange on $G\alpha$ subunits with parallel signal transduction pathways to modify the biological outcome (Kehrl, *Immunity* 8:1–10, 1998; Strittmatter et al., *Nature* 344:836–841, 1990). Nevertheless, biological/biochemical responses to activation of a GPCR are determined primarily by the nature of the $G\alpha$ subunits to which it is coupled, and this cannot be predicted by primary sequence analysis of newly discovered GPCRs (Hedin et al., *Cell Signal* 5:505–518, 1993). A primary objective, therefore, in the study of an orphan GPCR is to define its $G\alpha$ coupling profile. While direct experimental approaches such as photolabelling of $G\alpha$ subunits with radiolabeled GTP analogues have been useful in studies of GPCRs with known ligands or agonists (Offermanns et al., *Meth. Enzymol.* 195:286–301, 1991), they are limited in their application to the study of GPCRs in the absence of a defined ligand/agonist. However, signaling events downstream of many $G\alpha$ subunits have been well defined and their analysis can serve as surrogate assays of $G\alpha$ coupling profiles. Indeed, the biochemical/signaling properties of GPCRs are most often recapitulated in heterologous cell-types (Beadling et al., *J. Immunol.* 162:2677–2682, 1999) and cell lines in which the spectrum of expressed $G\alpha$ subunits are defined can serve as systems in which to study the primary signal transduction and biological characteristics of orphan GPCRs. Such approaches have therefore been used for preliminary analyses of orphan GPCRs as well as for ligand/drug screening protocols (Fraser, *J. Nucl. Med.* 36:17S–21S, 1995).

Interest in this family of receptors has increased with the realization of their potential clinical applications as drug targets. From the perspective of their clinical significance there is considerable focus on GPCRs expressed in the hematopoietic and lymphoid systems as many have been shown to play pivotal roles in the regulation of hematopoiesis and immune function. Receptor/ligand relationships within the GPCR family exhibit significant promiscuity, with many receptors recognizing more than one ligand and vice versa. This is especially true among chemokine receptors and a major goal, therefore, is to define the spectrum of receptor/ligand interactions within this family of GPCRs, which includes a number of lymphoid expressed orphan receptors of unknown function.

Interestingly, GPCRs have functional homologues in human cytomegalovirus and herpesvirus, suggesting that GPCRs may have been acquired during evolution for viral pathogenesis (Strader et al., *FASEB J.*, 9:745–754, 1995; Arvanitakis et al. *Nature*, 385:347–350, 1997; Murphy, *Annu. Rev. Immunol.* 12:593–633, 1994).

The importance of G protein-coupled receptors is further highlighted by the recent discoveries that its family members, chemokine receptors CXCR4/Fusin and CCR5, are co-receptors for T cell-tropic and macrophage-tropic HIV virus strains respectively (Alkhatib et al., *Science*, 272:1955, 1996; Choe et al., *Cell*, 85:1135, 1996; Deng et al., *Nature*, 381:661, 1996; Doranz et al., *Cell*, 85:1149, 1996; Dragic et al., *Nature*, 381:667 (1996); Feng et al., *Science* 272:872, 1996). It is conceivable that blocking these receptors may prevent infection by the human immunodeficiency (HIV) virus.

Cell cycle checkpoints, intervals in the cell cycle in which the cell detects impairment or loss of integrity to its genome and arrests growth in order to make repairs, ensure that DNA is replicated with high fidelity (Paulovich et al., *Cell* 88:315–321, 1997; Hartwell, *Cell* 71:543–546, 1992). There are three separately defined times in the eukaryotic cell cycle identified as checkpoints: G1/S transition, S-phase delay and G2/M transition (Nurse, *Cell* 91:865–867, 1997). The G1/S checkpoint is activated to avoid copying mutated DNA by increasing the time available for repair. Cells also utilize a DNA damage checkpoint within S phase by slowing the rate of DNA replication. The G2/M checkpoint is activated upon detection of double-stranded DNA breaks. In addition, mitotic entry is monitored by a spindle checkpoint that inhibits anaphase progression when chromosomes are not attached to the mitotic spindle (Nicklas, *Science* 275:632–637, 1997). The cell cycle checkpoint is summarized in FIG. 1.

Recent discoveries have shed light on the molecular participants in the G2/M transition. Cdc2 and Cyclin B1 promote entry into mitosis and are part of the maturation promoting factor (MPF). Dephosphorylation of Cdc2 on Thr14 and Tyr15 by Cdc25 and phosphorylation on Thr161 concomitant with nuclear association with Cyclin B1 results in rapid entry into mitosis. Cyclin B1 degradation or export to the cytoplasm and phosphorylation of Cdc2 on the negative regulatory sites Thr14 and Tyr15 by Wee1 block entry into mitosis. Caffeine can relieve DNA damage-activated G2/M arrest by stimulating the dephosphorylation of Cdc2. These data strongly implicate MPF as the central regulator of the transition from G2 into mitosis.

Recent work has broadened our understanding of the signaling pathways involved in G2/M arrest upstream of MPF. Response to DNA damage is detected by the Ataxia Telangiectasia mutated (ATM) which is a human homologue of the yeast rad family of genes (Meyn, 1995). The ATM protein has been implicated in the activation of Chk1, which phosphorylates Cdc25, leading to binding and sequestering of Cdc25 by 14-3-3 (Sanchez et al., *Science* 277:1497–1501, 1997; Peng et al., *Science* 277:1501–1505, 1997; Fumari, *Science* 277:1495–1497, 1997). This results in accumulation of the phosphorylated (inactive) form of Cdc2 and G2/M arrest. Cds1 has been demonstrated to function redundantly to Chk-1 by phosphorylating both Wee1 and Cdc25, inactivating both gene products (Boddy et al., *Science* 280:909–912, 1998; Fumari et al, supra.; Sanchez et al., supra.). ATM serves to activate proteins that act directly on MPF and lead to cell cycle arrest.

ATM also associates with and activates proteins that stimulate transcription of secondary molecules involved in checkpoint controls. One of these downstream activators of ATM is the tunor suppressor p53. Activation of p53 leads to the induction of multiple genes, including p21Cip and 14-3-3 (Levine, *Cell* 88:323–331, 1997). The 14-3-3 gene product mediates G2/M arrest by binding to Cdc25 to sequester it in the cytoplasm. The tyrosine kinase Abl physically interacts with the ATM gene product (Shafinan, *Nature* 5 387:520–523, 1997; Baskaran, *Nature* 387:516–519, 1997). Activation of the Abl kinase by DNA damage is dependent on the ATM, suggesting a functional link of Abl and ATM in the DNA damage checkpoint regulation. The overall regulation of the G2M checkpoint is an intricate mechanism involving both post-transcriptional modifications and transcriptional activation to guarantee proper cell growth. Thus, the known G2/M checkpoint proteins ultimately function through regulation of Cdc2 phosphorylation and nuclear import of Cyclin B1.

While the general eukaryotic cell cycle control machinery is highly conserved among a broad range of cell types, little is known about tissue-specific cell cycle regulators. TGF-β and GATA-5 represent anti-proliferative signaling molecules that are restricted in expression. Both of these regulators restrict the cell cycle at G1. Lymphocytes provide an interesting model system to study tissue-specific cell cycle regulators since their development is marked by the unique property of entering, exiting and re-joining the cell cycle depending on their internal developmental stages as well as the surrounding environment. For example, upon interaction with antigen, the resting mature naive B cells accumulate in the lymphoid germinal centers in which they undergo vigorous proliferation and excess B cells die by being included from germinal centers.

Loss of cellular growth controls by oncogenic transformation is dependent on signals emanating from the oncogene to downstream signaling partners and frequently leads to transcriptional induction of secondary genes which contribute to malignant growth. BCR-ABL is a chimeric tyrosine kinase oncogene generated by a reciprocal chromosomal translocation t(9;22)(q34;q11) associated with the pathogenesis of chronic myelogenous leukemia (CML) and acute lymphocytic leukemia (ALL) (Kurzrock, *N. Engl. J. Med.* 319: 990–998, 1988). This chimeric oncogenesis found in Ph[1]-positive stem cells. Structural and functional analysis have defined critical domains within BCR-ABL responsible for its oncogenic activity. In particular, the R552L substitution within a highly conserved motif of the Src Homology 2 (SH2) domain uncouples the SH2 domain with phosphotyrosine-containing proteins without affecting the kinase activity of BCR-ABL. Interestingly, this mutation greatly reduces the ability of BCR-ABL to stimulate anchorage-independent growth of rat fibroblasts in soft agar (Goga, *Cell* 82:981–988, 1995). Although the SH2 mutant still retains the ability to transform primary bone marrow cells in vitro, it exhibits diminished malignant and leukemogenic potential in mice (Goga, supra.). Inactivation of the SH2 domain may uncouple BCR-ABL with downstream signaling molecules, which in turn may alter the expression of critical genes involved in leukemogenesis.

SUMMARY OF THE INVENTION

A method for identifying a compound which inhibits T cell hyperproliferation, comprising the steps of: contacting a G2A receptor with a test compound; determining whether the compound binds to said G2A; and if the compound binds to G2A, detemininig whether the compound activates said G2A receptor, whereby activation of the receptor indicates that the compound is a potential inhibitor of T cell proliferation. In one aspect of this preferred embodiment, the T cell hyperproliferation is associated with an autoimmune disorder, inflauummatory disorder or malignancy. Preferably, the T cell hyperproliferation is associated with a disorder selected from the group consisting of rheumatoid arthritis, psoriasis, inflammatory bowel disease, T cell an immature B cell malignancies and diabetes. In one aspect of this preferred embodiment, the G2A is expressed on the cell surface. Advantageously, the determining step comprises a high density bone marrow transformation assay.

The present invention also provides a method for inducing cell cycle arrest in a cell, comprising contacting said cell with a compound which activates the G2A receptor. Preferably, the cell cycle arrest occurs at the G2/M transition of the cell cycle. In one aspect of this preferred embodiment, the cell is a leukemia cell or lymphoma cell.

Another embodiment of the present invention is a method for determining the presence of cancer cells, comprising determining whether the cells express the G2A transcript, wherein the presence of an increased level of the transcript compared to a control cell indicates that said cell is a cancer cell. Preferably, the determining step comprises Northern hybridization or polymerase chain reaction.

The present invention also provides a method for detecting the presence of cancer cells, comprising determining whether the cells express G2A protein, wherein the presence of an increased level of the protein compared to a control cell indicates that the cell is a cancer cell. Preferably, the determining step comprises contacting the cells with an antibody specific for the G2A protein and detecting the presence of the antibody. In one aspect of this preferred embodiment, the detecting step comprises fluorescence activated cell sorting (FACS).

BRIEF DESCRIPTION OF THE FIGURES

FIG. 5 shows the sequence aligment of the murine (SEQ ID NO: 2) and human (SEQ ID NO: 4) G2As. The human (SEQ ID NO: 4) and murine (SEQ ID NO: 2) G2As share approximately 70% identity at the amino acid level.

FIG. 8 is a flow cytometry profile showing counter-selection of G2A in pre-B cells transformed with the G2A-GFP or GFP retroviral vectors.

FIG. 27 is a graph showing G2A−/− and G2A+/+ B-cell proliferation stimulated by lipopolysaccbaride (LPS).

DETAILED DESCRIPTION OF THE PREFERRD EMBODIMENTS

The present invention describes the identification and sequencing of a novel G protein-coupled receptor (GPCR), called G2A for G2 arrest, which is transcriptionally regulated by a variety of intracellular and extracellular stimuli including tyrosine kinases, DNA damaging agents and chemotherapeutic drugs. G2A appears to serve as a tissue specific sensor of DNA damage and cellular proliferation, and functions at the G2/M checkpoint to delay mitosis following DNA damage, or to prevent deregulated growth incurred by excessive growth stimuli. Therefore, G2A may couple proliferative signaling and cell cycle checkpoint pathways to ensure faithful and properly controlled duplication of hematopoietic cells.

In addition, transcriptional induction and expression of G2A integrates diverse signals by modulation of cytoskeletal architecture. Employing microinjection of constructs encoding G2A into Swiss 3T3 fibroblasts and embryonic fibroblasts derived from various Gα knockout mice, a signaling pathway was delineated downstream of G2A leading to actin reorganization into stress fibers via Gα13 and RhoA. Microinjection of constitutively active mutants of RhoA into Swiss 3T3 fibroblasts induces the formation of actin stress fibers and focal adhesions (Ridley et al., Cell 70:389–399, 1992). In addition, RhoA functions as a downstream component of signaling pathways initiated by ligand stimulation of the G protein-coupled LPA receptor leading to stress fiber assembly (Barry et al., J. Cell Sci. 107:2033–2045, 1994). Direct activation of RhoA by G2A was observed in Swiss 3T3 fibroblasts. In addition, RhoA dependent transcriptional activation of Serum Response Factor (SRF) induced by transient expression of G2A required both Gα13 and Gα12. Thus, G2A expression and transcriptional induction may play a role in the integration of proliferative and/or differentiative signals with cytoskeletal reorganization.

Figure 1:
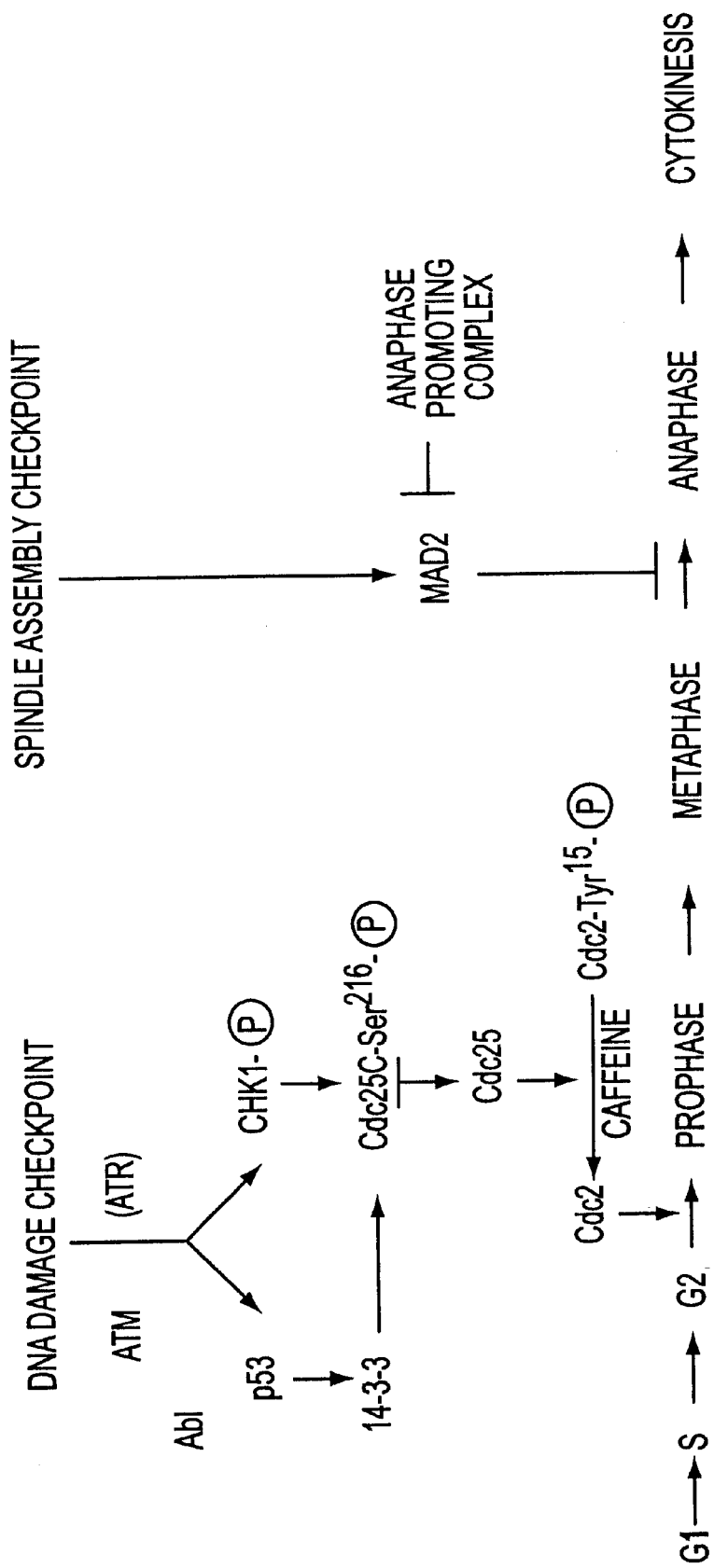
FIG. 1 is a schematic diagram showing the mammalian cell cycle checkpoint.
Figure 2:
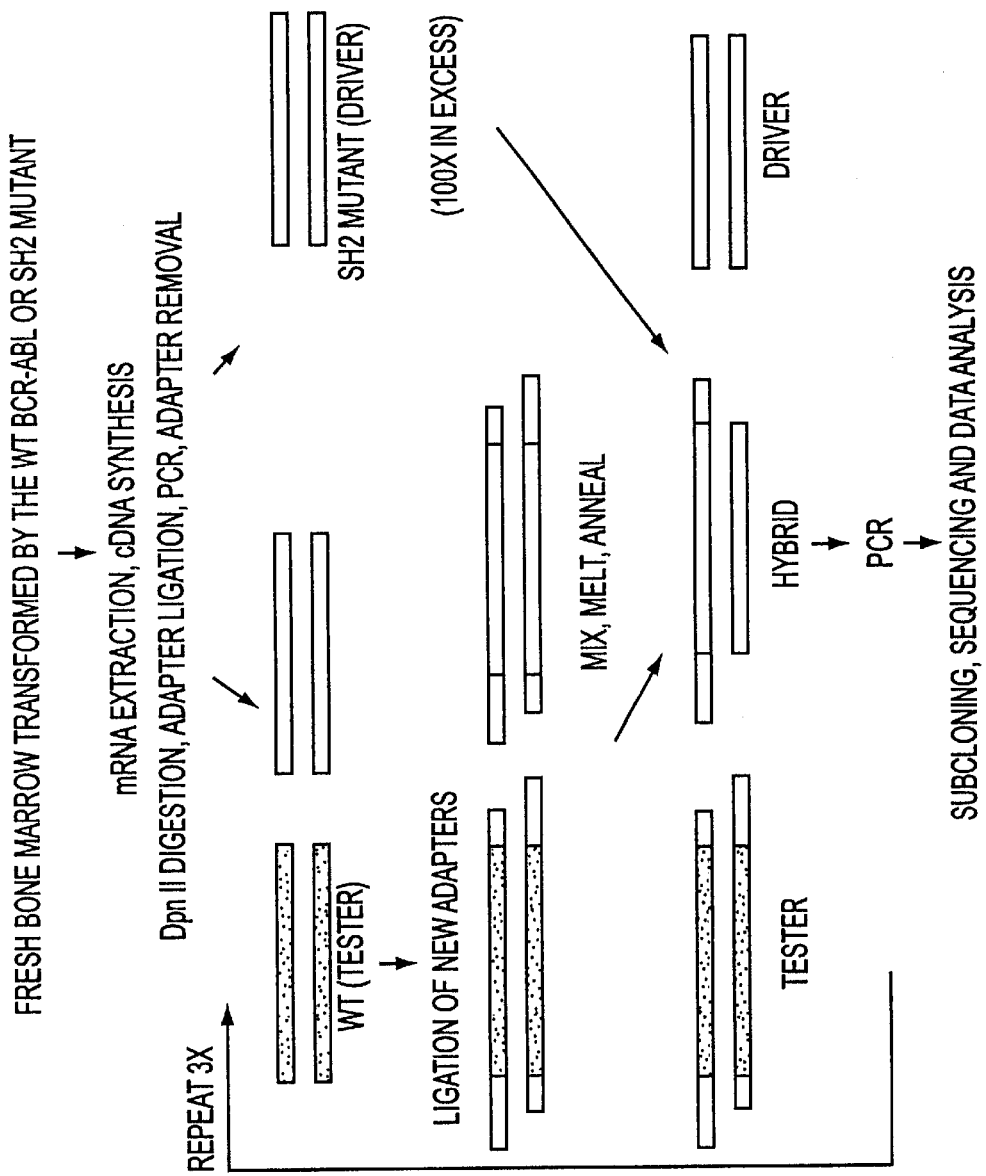
FIG. 2 is a schematic diagram depicting the isolation of differentially-expressed genes by representational difference analysis (RDA). After mRNA isolation and cDNA synthesis, tester and driver cDNAs are digested with a restriction enzyme (RE) and ligated with adapters. After PCR amplification, the adaptors are removed by RE digestion and new adaptors are ligated to the tester DNA fragments only. The tester DNA is hybridized to an excess of driver DNA. DNA fragments from differentially-expressed genes will form homodimers with the new adapters at both ends and can be exponentially amplified by PCR. Fragments present in both driver efficiently amplified. The process is repeated 3–4 times and differentially amplified DNA fragments are subcloned for further analysis.

G2A also functions as a tumor suppressor gene, induces cell cycle arrest during mitosis and is found on human chromosome 14q32.3, a region frequently found altered in human cancers. G2A was identified while studying cellular genes that can be regulated by BCR-ABL. Using representational difference analysis (RDA), a PCR-based differential screening technique (Lisitsyn et al., *Science* 259:946–951, 1993; Hubank et al., *Nucl. Acids Res.* 22:5640–5648, 1994; FIG. 2), genes expressed in murine bone marrow (pre-B) cells transformed by the wild type (WT) BCR-ABL were compared to those expressed when a transformation-defective mutant variant carrying a mutation in the SH2 domain of BCR-ABL was used to infect these cells. More than a dozen genes were found to be upregulated by BCR-ABL. One of these differentially expressed murine genes (G2A) was predominantly expressed primarily in hematopoietic and lymphoid tissues such as spleen, thymus and lymph nodes as determined by semi-quantitative PCR, and was induced by WT BCR-ABL, but not the SH2 mutant.

The cDNA and deduced amino acid sequences of the murine G2A are shown in SEQ ID NO: 1 and SEQ ID NO: 2, respectively. The human homologue of the mouse protein was then isolated using the murine cDNA as a probe. The corresponding human cDNA and deduced amino acid sequences are shown in SEQ ID NO: 3 and SEQ ID NO: 4, respectively. The G2A protein sequence of the invention has the sequence shown in SEQ ID NOS; 2 and 4, or sequence variations thereof which do not substantially compromise the ability of these genes to be regulated by protein tyrosine kinases or sequence variations thereof which do not substantially compromise the functional activities of these proteins. It will be appreciated that G2A proteins containing one or more amino acid replacements in various positions of the sequences shown in SEQ ID NOS: 2 and 4 are also within the scope of the invention.

Many amino acid substitutions can be made to the native sequence without compromising its functional activity. Variations of these protein sequences contemplated for use in the present invention include minor insertions, deletions and substitutions. For example, conservative amino acid replacements are contemplated. Such replacements are, for example, those that take place within a family of amino acids that are related in the chemical nature of their side chains. The families of amino acids include the basic amino acids (lysine, arginine, histidine); the acidic amino acids (aspartic acid, glutamic acid); the non-polar amino acids (alanine, valine, leucine, isoleucine, proline, phenylalanine, methionine, tryptophan); and the uncharged polar amino acids (glycine, asparagine, glutamine, cysteine, serine, threonine, tyrosine) and the aromatic amino acids (phenylalanine, tryptophan, tyrosine). In particular, it is generally accepted that conservative amino acid replacements consisting of an isolated replacement of a leucine with an isoleucine or valine, or an aspartic acid with a glutamic acid, or a threonine with a serine, or a similar conservative replacement of an amino acid with a structurally related amino acid, in an area outside of the polypeptide's active site, will not have a major effect on the properties of the polypeptide.

Figure 3:
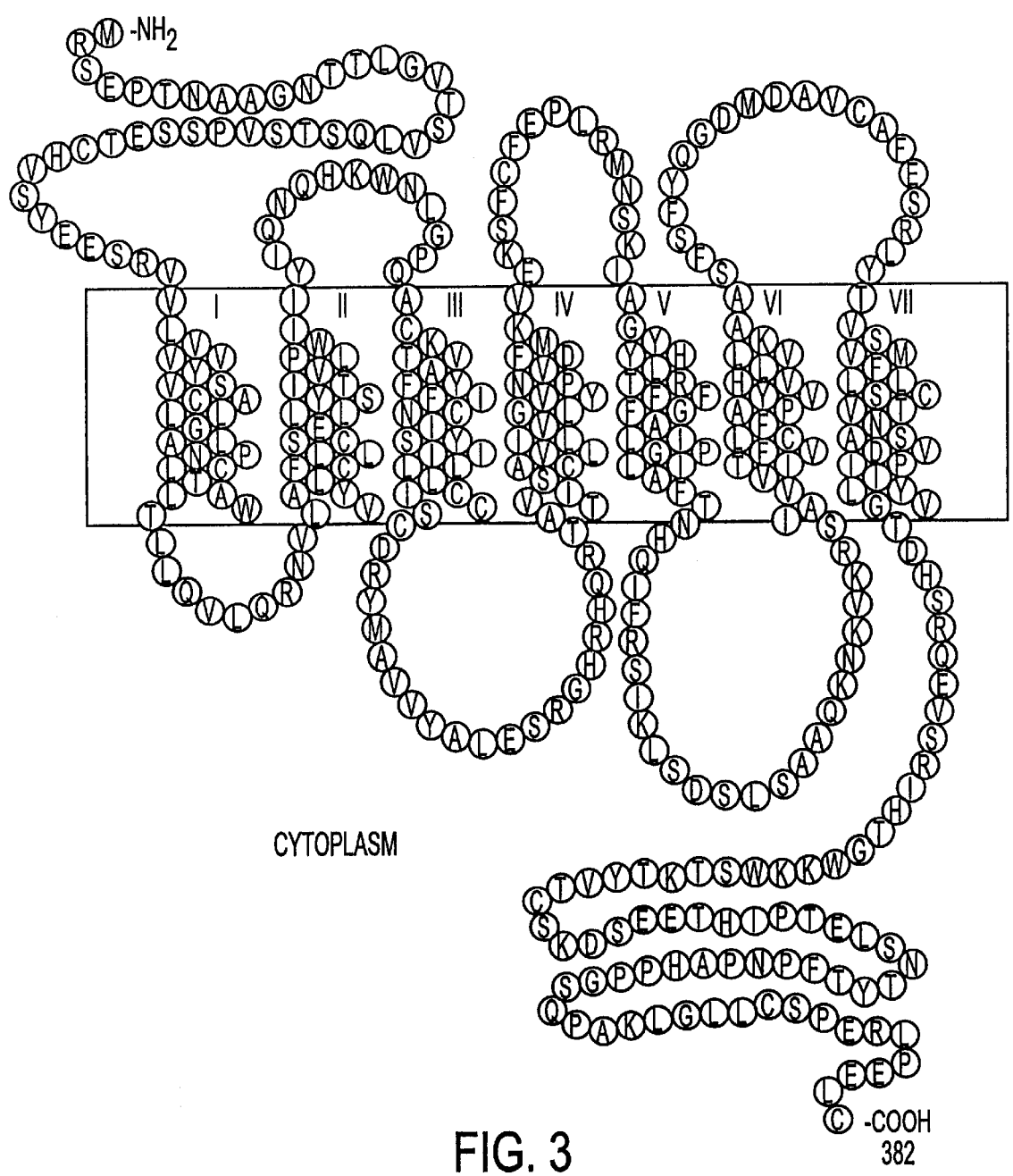
FIG. 3 is a schematic diagram of murine G2A (SEQ ID NO: 2) showing the seven predicted tansmembrane domains.
Figure 4:
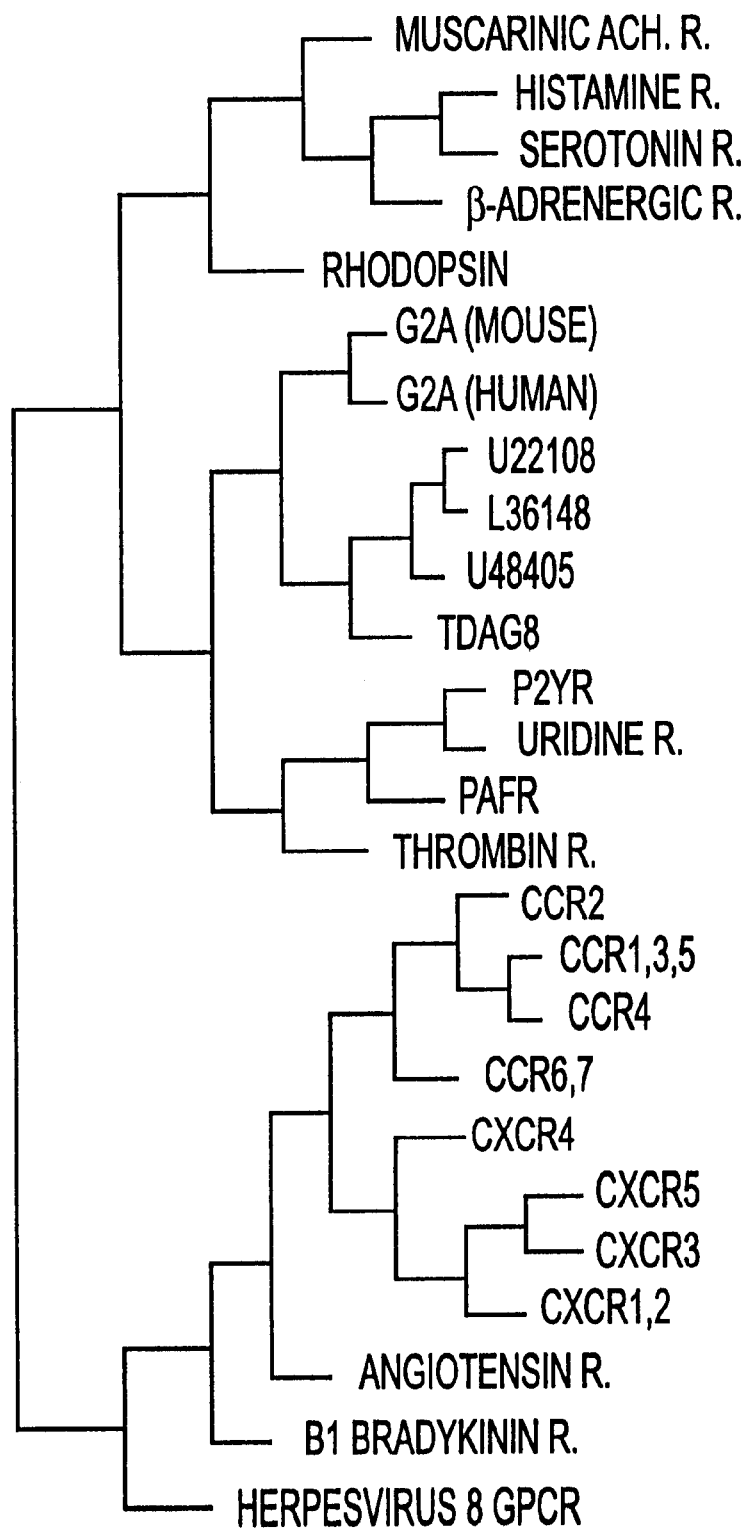
FIG. 4 is a phylogenetic tree of GPCRs showing the relationship of G2A with other GPCR family members.

The murine protein was determined to be a member of the GPCR superfamily by its homology to other GPCRs, including the mouse TDAG8 protein and the P2Y purinoceptor, using sequence alignment programs. A schematic diagram of murine G2A showing the seven predicted transmembrane domains is shown in FIG. 3. A GPCR phylogenetic tree is shown in FIG. 4. The human G2A homologue was isolated by screening a human spleen cDNA libraiy under high stringency conditions (2×SSC, 0.1% SDS, 65° C.). The murine and human G2As share approximately 70% identity at the amino acid level (FIG. 5) and have a calculated molecular weight of about 42 kDa. These proteins share the highest degree of identity (76%) in the seven transmembrane domains as well as the extracellular and intracellular loops, whereas they are more divergent in the N-terminal extracellular domain (25% identity) and C-terminal cytoplasmic tail (55% identity). Both murine and human G2A contain putative N-linked glycosylation sites in the N-terminal extracellular domain characteristic of GPCRs. Any DNA molecule capable of hybridizing the DNA sequence shown in SEQ ID NO: 1 under these conditions or lower stringency conditions, as well as the protein encoded by such a DNA molecule, is within the scope of the invention.

Northern analysis of various murine tissue samples using a multiple tissue Northern blot detected two G2A transcripts of about 3 kb and 5 kb in hematopoietic tissues such as spleen, thymus, lung and heart, but not in normal bone marrow, brain, liver, skeletal muscle or kidney. Thymocytes were isolated and shown by a semi-quantitative RT-PCR to express G2A regardless of their developmental state. Northern analysis of human tissues showed that the human G2A is exclusively expressed in spleen and peripheral leukocytes, but not in heart, brain, placenta, lung, liver, skeletal muscle, kidney, pancreas, thymus, prostate, testis, ovary, small intestine and the mucosal lining of the colon. This furter suggests a role of this gene in hematopoiesis. The human G2A is transcriptionally activated in B cells upon activation by either phorbol 12-myristate 13-acetate (PMA) plus ionomycin or anti-IgM antibodies. The activation of G2A transcription was also observed in B cells upon irradiation with x-rays or activation by the CD40 ligand. The human G2A transcript is also present in the ALL-1 and K-562 leukemia cell lines.

The G2A was transcriptionally activated by BCR-ABL and v-Abl, a protein tyrosine kinase oncogene found in Abelson Murine Leukemia Virus. To our knowledge, this is the first demonstration that a GPCR can be transcriptionally regulated by a protein tyrosine kinase. Interestingly, a mutant form of BCR-ABL (carrying a mutation in the SH2 domain) that lacks oncogenic potential failed to transcriptionally activate the G2A. In addition, Cyclin D1, an important cell cycle regulator (Afar et al., *Proc. Natl. Acad. Sci. U.S.A.* 92:9540–9544, 1995) that can complement the BCR-ABL mutant for transformation, restored the expression of the G2A. These data suggest that this GPCR may also be a marker for transformation by BCR-ABL and other tyrosine kinase signaling pathways.

Figure 6:
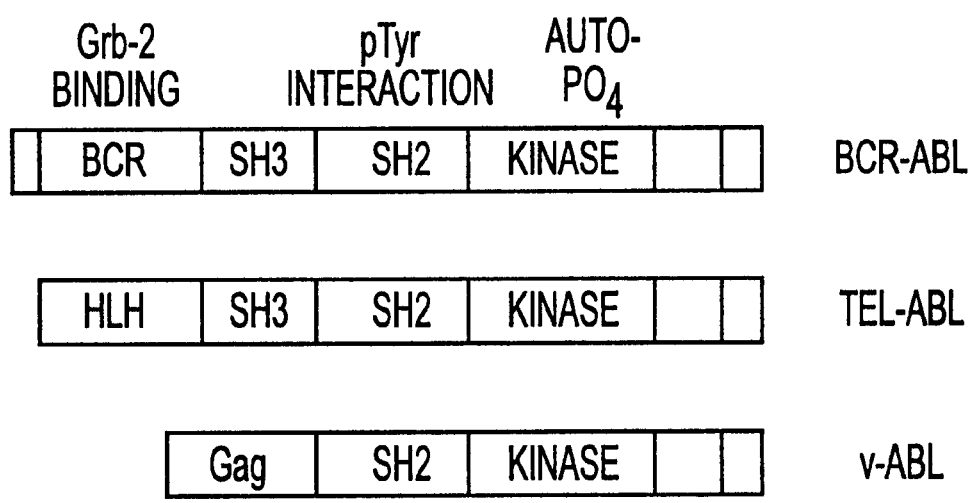
FIG. 6 is a schematic diagram showing the various domains of BCR-ABL, TEL-ABL and v-ABL. SH3=src homology region 3; SH2=src homology region 2; pTyr= phosphotyrosine; Auto-$PO_4$=autophosphorylation site; Grb-2=adaptor protein which couples BCR-ABL to Ras; HLH= helix-loop helix domain involved in oligomerization of the protein and activation of Abl kinase activity.

FIG. 6 shows the domains of BCR-ABL, TEL-ABL (an oncogenic fusion protein associated with leukemia) and v-ABL. TEL-ABL, Grb-2 (an adaptor protein which couples BCR-ABL to Ras) mutant and autophosphorylation mutant did not activate the G2A. The G2A receptor was also transcriptionally activated by v-Mos, a serine kinase oncogene that activates MAP kinase (Davis, *Mol. Reprod. Dev.* 42:459–67, 1995). Since v-Mos, BCR-ABL and v-ABL all activate MAP kinases (Davis, supra.), the G2A may be directly regulated by MAP kinase signaling pathways. Therefore, it is contemplated that the G2A may also be activated by a wide-variety of protein kinases as well as their regulators and effectors during cell growth and differentiation such as Ras, Myc, Fos, Jun and BTK.

The G2A is expressed in spleen and thymus, but not in normal bone marrow cells, suggesting that it may play an important role in mid- and late stages of T and B cell development. During development, self-reactive immature thymocytes are clonally deleted in the thymus, a phenomenon which establishes T cell tolerance (negative selection). It has been shown that the deletion of self-reactive immature T cells in the thymus is mediated by apoptosis upon T cell receptor engagement. TDAG8, a GPCR family member, is induced in T cells during apoptosis upon T cell receptor activation (Choi et al., *Cell. Immunol.*, 168:78–84, 1996). This suggests that TDAG8 may play a role in negative selection of T cells. Since the G2As that we isolated share about 30% homology with TDAG8, it is conceivable that the G2As may also play a role in negative selection of T cells. Sequence analysis of the G2A with its family members reveal that they also share significant homology with the P2Y receptor, a GPCR for ATP. It has been shown recently that P2Y receptor is transcriptionally upregulated during T cell activation (Koshiba et al., *Proc. Natl. Acad. Sci. U.S.A.*, 94:831–836, 1997).

The G2As may play a role in directing migration of lymphocytes into specific anatomical compartments of spleen and thymus for maturation. Previous studies on a hematopoietic-specific GPCR, BLR1, suggest that BLR1 plays an important role for directing migration of lymphocytes into splenic follicles as well as migration of activated B cells into B cell-follicles of the spleen, a prerequisite for the development of an antigen-specific immune response (Forster et al., *Cell*, 87:1037–1047, 1996). Expression of G2As in hematopoietic-specific tissues suggest that it may also play similar roles in directing migration of lymphocytes into lymphoid organs for their maturation.

Both the mouse and human G2A cDNA clones can be used for in situ analysis to examine whether the expression of the receptor is restricted to certain anatomical regions of the spleen and thymus. The mouse and human genomic clones encoding the full length G2As were also isolated. The mouse genomic clone has been used for constructing a targeting vector to knock-out the G2A in mice by homologous recombination. The G2A−/− mice will allow further evaluation of the physiological functions of this receptor. The G2A−/− mice will also allow determination of whether in vivo leukemogenesis is dependent on the G2A. The mouse and human genomic clones may contain the distal and proximal promoters of the G2As that will allow the analysis of the transcriptional regulation of hematopoietic-specific genes. Both the mouse and human genomic clones can also be used for cytogenetic mapping to examine whether the G2As are linked to any known genetic diseases.

Rabbit antisera was prepared which was reactive with either the N-terminal portion or the C-terminal portion of the receptor as confirmed by ELISA. Two rabbits were injected with a 13 amino-acid peptide corresponding to the cytoplasmic tail of the receptor. Another two rabbits were injected with GST-G2A-N, a glutathione-S-transferase fusion protein containing the N-terminal extracellular domain of the G2A. The sera from the second, third, and fourth production bleed of both rabbits exhibited strong immune response to the peptide as seen in the ELISA assay. The antibodies were affinity purified using a peptide affinity column and are valuable for analyzing the expression of this G2A in T and B cell development. These antibodies were used to assist in determining the structure and localization of the G2A protein. The anti-N-terminal antibodies detected the G2A protein under the non-permeabilized and permeabilized conditions, whereas the anti-C-terminal antibodies only detected G2A under perneabilized conditions. These results suggest that the N-termlinal portion is the extracellular domain and the C-terminal portion is the intracellular domain which is consistent with known GPCRs.

Monoclonal antibodies to the receptor can also be generated using conventional hybridoma technology known to one or ordinary skill in the art. Briefly, three mice are immunized with 25 μg recombinant receptor prepared as described in Example 9. Mice are inoculated at 3 week intervals with 20 μg G2A per mouse (½ subcutaneously and ½ intraperitoneally). Serum collected from each animal after the first inoculation reacts with G2A as determined by immunoprecipitation. Three days after the final inoculation, mice are sacrificed and the spleens harvested and prepared for cell fusion. Splenocytes are fused with Sp2/0 AG14 myeloma cells (ATCC CRL 1581) with polyethylene glycol (PEG).

Following PEG fusion, cell preparations are distributed in 96-well plates at a density of $10^5$ cells per well and selected in hypoxanthine/aminopterin/thymidine (HAT) medium containing 10% fetal calf serum and 100 U/ml interleukin-6. The medium is replaced with fresh HAT medium 10 days after plating. To identify hybridomas producing MAbs which recognize G2A, hybridoma supernatants are tested for the ability to immunoprecipitate purified recombinant G2A or to detect G2A by immunoblotting.

A glutathione-S-transferase (GST) fusion protein of the N-terminal extracellular domain of the G2A was constructed. The mouse and human G2As were cloned into various eukaryotic expression vectors which will allow the overexpression of recombinant mouse and human G2As in transfected cells in vitro and in vivo by methods well known to one of ordinary skill in the art. Preferably, the constructs containing the G2A is transfected into eukaryotic cells; more preferably into mammalian cells. Alternatively, the construct may be used to transform bacterial cells.

Growth arrest induced by G2A indicates its potential for therapeutic intervention in cases of deregulated proliferation of lymphoid cells. G2A resists cellular proliferation, thus its agonists are useful in delaying the progression of diseases including leukemias, lymphomas and autoimmune diseases. Since G2A is upregulated by BCR-ABL and can suppress the outgrowth of lymphocytes and fibroblasts (Tables 4A–B), antibodies, drugs or natural ligands can be screened in vitro which can activate G2A. Drugs, antibodies or natural ligands which inhibit the growth of lymphocytes are useful for treatment of the diseases mentioned above.

Conversely, monoclonal antibodies can be generated against particular regions of G2As which block the G2As and stimulate the growth of normal lymphocytes in vivo. In addition, in vitro screening assays can be used to find drugs or natural ligands which bind to and either activate or inactivate the G2A. These antibodies, drugs or natural ligands can stimulate the growth of lymphocytes, which may in turn cure or alleviate the symptoms of patients who have either inherited immunodeficiency diseases or Acquired immune deficiency syndrome (AIDS). For example, patients with severe combined immune deficiency (SCID), DiGeorge syndrome, or Bare lymphocyte syndrome lack T cells, and patients with X-linked agammaglobulinemia lack B cells. The antibodies, drugs, natural ligands can be delivered into these patients to inhibit the G2A to stimulate the growth of the T and B cells in their immune system.

In a preferred embodiment, the cDNA encoding the G2A is placed in a eukaryotic expression vector for transfection into or infection of a mammalian cell line. Many such cell lines are known in the art, including NIH 3T3, Rat-1, 293T, COS-1, COS-7 and Chinese hamster ovary (CHO) cells, most of which are available from the American type Culture Collection (ATCC), Rockville, Md. Many such expression vectors are known and are commercially available. Preferred expression vectors include retroviral vectors, adenoviral vectors and SV40-based vectors. The vector may contain a selectable marker, such as antibiotic resistance, to select for cells which are expressing the receptor. Alternatively, the expression of the G2A can be under the control of a regulatory promoter. Stable transfectants are used to screen large libraries of synthetic or natural compounds to identify compounds which bind to the G2A. Compounds which bind to the G2A are then tested in the assays described in Examples 7, 10, 11 and 12 to determine whether they are agonists or antagonists of BCR-ABL-mediated G2A activation.

In one embodiment of the invention, a compound to be tested is radioactively, calorimetrically or fluorimetrically labeled using methods well known in the art and incubated with the receptor. After incubation, it is determined whether the test compound is bound to the receptor. If so, the compound is a potential agonist or antagonist. Functional assays are performed to determine whether the receptor activity is activated or inhibited. These assays include fibroblast and bone marrow transformation assays, cell cycle analysis and in vivo tumor formation assay. Responses can also be measured in cells expressing the receptor using signal transduction systems including, but not limited to, protein phosphorylation, adenylate cyclase activity, phosphoinositide hydrolysis, guanylate cyclase activity, ion fluxes (i.e. calcium) and pH changes. These types of responses can either be present in the host cell or introduced into the host cell along with the receptor.

G2A receptor agonists isolated as described above can be used to promote cell cycle arrest at the G2/M transition in malignant cells, particularly hematopoietic cells such as leukemia cells and lymphoma cells, both in vitro and in vivo. Because G2A is induced by protein tyrosine kinase oncogenes, it can be used as a diagnostic marker for many types of cancer, including leukemia. The DNA sequence can also be used as a probe to search for additional closely-related family members which may play similar roles in oncogenesis.

As determined using mouse knock-out experiments, loss of function of G2A makes lymphoid cells more susceptible to leukemogenesis and results in hyper-proliferative T lymphocytes. Thus, agonists to the G2A receptor would be usefull in limiting T cell responses and could be used to treat a broad range of autoimmune and inflammatory disorders resulting from excessive responses of T lymphocytes (T cell hyperproliferation). These disorders include, but are not limited to, rheumatoid arthritis, psoriasis, inflammatory bowel diseases (e.g., Crohn's disease, colitis), T cell and immature B cell malignancies and diabetes. Thus, the assays for identifying agonists of G2A described herein can also be used to identify compounds which can be used to treat T cell-mediated autoimmune and inflammatory disorders. These assays comprise the steps of determining whether a compound binds to G2A, and testing compounds which bind to G2A to determine whether they activate the G2A receptor using any of the methods described herein.

G2A is not expressed in normal bone marrow cells, but is expressed in spleen. Thus, It is possible that G2A regulates blood cell development. Regulation of the activity of the G2A (by antibodies, inhibitory or stimulatory drugs, or natural ligands) may be clinically useful in restoring the normal number and function of the blood cell population with suppressed hematopoiesis, such as that which occurs after treatment to obtain immunune depression for organ transplants or after cytotoxic cancer therapy.

The expression of G2A in heart suggests that this gene may play a physiological role in heart. It has been shown that there are a variety of autoantibodies, including antireceptor autoantibodies, in patients with cardiomyopathy (Fu, *Mol. Cell. Biochem.* 163:343–7 (1996). Patients with cardiomyopathy may have autoantibodies against the G2A which contribute to the pathogenesis of cardiomyopathy. Therefore, regulation of G2A function by neutralizing antibodies, drugs, or natural ligands may alleviate the symptoms of patients with cardiomyopathy. The G2As may also be involved in cardiovascular, hypertension-related, cardiac function defects. Regulation of G2A function by neutralizing antibodies, drugs, or natural ligands may alleviate the symptoms in patients with such defects.

Since we have isolated both murine and human G2As, the cDNAs can be used to isolate the homologue of the G2As in other species. Identification of the homologues in other species may lead to a cure for the diseases mentioned above in animals, and will therefore have broad applications in veterinary medicine. The amino acid sequence information of the highly conserved regions of the murine and human G2As can be used to develop antibodies or drugs that can be used to treat diseases in both human and animals.

The following examples describe the cloning of the murine and human WT BCR-ABL-induced G2A.

EXAMPLE 1

Plasmid Constructs, Cell Lines, Preparation of Viral Stocks Generation of Antibodies The WT p185 BCR-ABL and the SH2 mutant were cloned into the pSRαMSV vector (Muller et al., *Mol. Cell. Biol.* 11:1785–1792. 1991) under the control of the LTR promoter as previously described (Afar et al., *Science* 264:424–426, 1994; Pendergast et al., *Cell* 75:175–185, 1993). The pSRαMSV vector was used to produce helper-free retroviral stocks by transient transfection of 293T cells along with the ψ⁻packaging vector (Pear et al., *Proc. Natl. Acad. Sci. U.S.A.*, 90:8392–8396, 1993; Afar et al., *Science* 264:424–426, 1994). A 13-amino acid peptide (KDSEETHLPTELS; SEQ ID NO: 5) corresponding to the C-ternninal intracellular portion of the murine G2A was synthesized and injected into rabbit for antibody production (Babco, Berkeley, Calif.). Five production bleeds were obtained. To generate the antibodies against the murine N-terminal extracellular portion of the G2A, a GST-Mu-G2A-N fusion construct was made by PCR. using GST-Mu-N2A-N5' and GST-Mu-N2A-N3' primers (See Table 2).

Briefly, PCR was performed in a total of 100 μl reaction mixture containing 20 ng template, 30 μl 3.3×XL buffer (Perkin Elmer, Norwalk, Conn.), 6 μl 25 mM magnesium acetate, 2 μl dNTPs (10 mM each nucleotide), 20 pmol of GST-Mu-N2A-N5' and GST-Mu-N2A-N3' primers, and 1 μl rTth polymerase (Perkin Elmer). The cycling conditions were 95° C. for 5 min, 30 cycles of denaturation at 94° C. for 0.5 min, annealing at 56° C. for 1 min and elongation at 72 ° C. for 1 min. After incubation at 72° C. for 10 min, the amplified PCR fragment was digested with BamHI and EcoRI (Boehringer Manrinheim, Indianapolis, Ind.) in Buffer B (10 mM Tris, 5 mM $MgCl_2$, 100 mM NaCl, 1 mM β-mercaptoethanol, pH 8.0, Boehringer Mannheim), and fractionated on an agarose gel. The DNA fragment was excised, purified using Geneclean™ (Bio 101, La Jolla, Calif.) and cloned into the pGEX-2T vector (Pharmacia Biotech) at the BamHI/EcoRI sites. Approximately 50 ng pGEX-2T BamHI/EcoRI fragment was ligated to the PCR product at a 1:3 molar ratio in 1X T4 DNA ligase buffer (50 mM Tris-HCl (pH 7.8), 10 mM MgCl$_2$, 10 mM DTT, 1 mM ATP, 50 µg/ml BSA) and 1 µl T4 DNA ligase (New England Biolabs, Beverly, Mass.) in a 10 µl, reaction volume at 16° C. overnight. Transformation was performed by mixing 10% of the ligation reaction with 100 µl of DH5 α competent *E. coli* cells on ice for 20 min. After heat shock at 42° C. for 2 min and incubation on ice for 2 min, 1 ml TYE was added and the transformed cells were further incubated at 37° C. for 1 hr. The transfornation mix was plated out on TYE plates containing ampicillin (50 µg/ml). One positive clone containing the insert was identified. The plasmid was sequenced to ensure the proper fusion of the murine N-terminal extracellular portion of G2A to GST.

EXAMPLE 2

Isolation of cDNA from Bone Marrow Cells

Total RNA was isolated from primary murine bone marrow cells transformed by a retrievers encoding either the WT p185 BCR-ABL or the SH2 mutant variant (Goga et al., *Cell* 82:981–988, 1995) using the Ultraspec RNA isolation system (Biotecx Laboratories, Inc., Houston, Tex.). Polyadenylated RNA was purified from total RNA using oligo (dT) cellulose columns (Collaborative Research) according to the manufacturer's instructions. cDNA was synthesized using SuperScript choice system (GibcoBRL Life Technologies, Gaithersburg, Md.), according to the manufacturer's protocols.

EXAMPLE 3

Representational Difference Analysis (RDA) and DNA Sequencing

To isolate genes that were differentially regulated by the WT p185 BCR-ABL, but not by the SH2 mutant variant, a modified version of a PCR-based subtractive-hybridization technique called Representational Difference Analysis (RDA) was used. RDA was originally developed to detect differences between two complex genomes (Lisitsyn et al., *Science*, 259:946–951, 1993). It was later adapted for use with cDNA and has been used successfully to isolate differentially expressed genes in various systems (Hubank et al., *Nucl. Acids Res.* 22:5640–5648, 1994; Braun et al., *Mol. Cell. Biol.* 15:4623–4630 (1995). The cDNA sample containing the genes of interest is termed the tester, and the sample used for subtraction is the driver. Both the tester and driver cDNAs are digested with a restriction enzyme, DpnII, then ligated to RBgl adapters (the RBgl12 and RBgl24 primers, see Table 2) for PCR amplification. The RBgl adapters were then removed. To isolate differentially-expressed genes, the amplified tester DNA is ligated to new adapters, JBgl adapters (the JBgl 12 and JBgl 24 primers, see Table 1) and mixed with the driver DNA in a subtractive hybridization. The differentially-expressed genes form tester-tester homo-duplexes and can be preferentially amplified by PCR using the JBgl24 primer. This process is repeated three times, with increasing ratios of driver to tester from 1:100, 1:800, to 1:8000 during subtractive hybridization (Lisitsyn et al., supra.; Hubank et al., supra.). In this study, cDNA from HDBM cells transformed by the WT p185 was used as the tester and that by the SH2 mutant as the driver to isolate genes that are upregulated by the WT p185 BCR-ABL. RDA was also performed in parallel using the SH2 mutant as the tester and the WT as the driver to isolate genes that are downregulated by the WT p185. The differentially amplified gene fragments were then digested with DpnII and cloned into the BamHI site of the pBluescript cloning vector (Stratagene, La Jolla, Calif.). DNA sequencing was then performed using ABI PRISM Dye Terminator Cycle Sequencing Ready Reaction Kit (Perkin Elmer) or Sequenase version 2.0 DNA sequencing kit (United States Biochemical, Cleveland, Ohio). After sequencing the clones from both directions, the sequence information was used to search databases using the BLAST program. Both the protein database (non-redundant updated protein database PDB+SwissProt+PIR) and nucleotide database (PDB+GenBank+EMBL) were searched. Sequence analysis of a 377 base-pair DNA fragment of a partial murine G2A clone (N2A) revealed that it was a novel G2A homologous to multiple GPCR family members in the database.

TABLE 1

| Oligonucleotides used for RDA | | |
|---|---|---|
| RBgl24 | AGCACTCTCCAGCCTCTCACCGCA | (SEQ ID NO: 6) |
| JBgl24 | ACCGACGTCGACTATCCATGAACA | (SEQ ID NO: 7) |
| NBgl24 | AGGCAACTGTGCTATCCGAGGGAA | (SEQ ID NO: 8) |
| RBgl12 | GATCTGCGGTGA | (SEQ ID NO: 9) |
| JBgl12 | GATCTGTTCATG | (SEQ ID NO: 10) |
| NBgl12 | GATCTTCCCTCG | (SEQ ID NO: 11) |

EXAMPLE 4

Isolation of Mouse G2A cDNA and Genomic Clones

The 377 bp N2A fragment was used as a probe to screen a mouse spleen cDNA library (Clontech, Palo Alto, Calif.) according to the manufacturer's instructions. Briefly, *E. coli* strain 1090r– was grown in TYE broth in the presence of 10 mM MgSO$_4$ and 0.2% maltose overnight. The library was incubated with overnight *E. coli* culture and then plated out on TYE plates using 0.7% agarose in TYE+20 mM MgSO$_4$. After incubation at 37° C. until plaques were about 1 mm in diameter, the plates were chilled at 4° C. for 1 hr before the filters were placed on the plates. The filters were then lifted and autoclaved at 100°C. for 1 min to denature the DNA. The filters were prehybridized for 4 h in hybridization buffer containing 1% SDS, 2×SSC (20×SSC=3 M NaCl, 0.3 M NaCitrate-2 H$_2$O, pH to 7.0), 10% dextran sulfate, 50% formamide, 1×Denhardt's solution (50×Denhardt's solution=1% ficoll, 1% polyvinylpyrrolidone and 1% BSA, pentax fraction V) and 0.25 mg/ml salmon sperm DNA. The N2A fragment was labeled using Primer-It II Random Primer Labeling Kit (Stratagene). The filters were hybridized overnight at 42° C. with the N2A probe in the hybridization buffer. The filters were washed twice with 2×SSC and 0.1% SDS for a total of 1.5 hrs. One positive clone was identified after screening 1×10$^6$ plaques. Sequence analysis revealed that the clone contained the C-terminal portion of the G2A. 5'-RACE was then used to obtain the N-temiinal portion of the gene using 5' RACE system (GibcoBRL) according to the manufacturer's instruction. Briefly, the N2AGSP1 primer (see Table 2) was used to prime first-strand cDNA synthesis. After purification of first-strand cDNA and homopolymer addition of dCTP by terminal deoxynucleotidyl transferase (TdT) to the cDNA at the 3' end, a nested primer, N2AGSP2 (see Table 2) that anneals to sequences located 3' of N2AGSP1 and the 5' RACE anchor primer (see Table 2) were used for PCR amplification of the N-temiinal fragment of the murine G2A. The PCR was performed in a 50 µl reaction mixture containing 20 mM Tris-HCl (pH 8.4), 50 mM KCl, 1.5 mM MgCl2, 200 uM each dNTP, 100 nM N2AGSP2 primer and 100 nM anchor primer. The dC-tailed cDNA was first denatured at 94° C. for 5 min. After addition of 2 units Taq DNA polymerase, PCR was performed by 35 cycles of denaturation at 94° C. for 0.5 min, annealing at 62° C. for 1 min and elongation at 72° C. for 3 min.

After obtaining the sequence information of the N-terminal portion of the gene, a full length clone was obtained by RT-PCR (3' RACE system, GibcoBRL) using total RNA isolated from bone marrow cells transformed by the WT BCR-ABL. The primers for generation of full length murine G2A were N2A 3' RACE-1 (5' primer) and MuN2A3'-2 (3' primer) (see Table 2). Briefly, PCR was performed in a 50 µl reaction mixture using the rTth DNA polymerase system (Perkin Elmer) containing 1×XL buffer, 1.5 mM magnesium acetate, 10 pmol of each primer, 2 µl of first strand cDNA synthesis product, 0.2 mM dNTPs and 0.5 µl of rTth polymerase (Perkin Elmer). The cycling conditions were 94° C. for 3 min, 35 cycles of denaturation at 94° C. for 0.5 min, annealing at 62° C. for 1 min and elongation at 72° C. for 3 min. The amplified PCR fragments were fractionated on an agarose gel. The approximately 1.3 kb fragment containing the full length murine G2A cDNA (SEQ ID NO: 1) was excised, purified using Geneclean™ and subcloned into the pCRII vector (Invitrogen, San Diego, Calif.). Multiple clones were sequenced using N2AGSP2, N2Arandom, N2A5, T7, and M13 Reverse primers (see Table 2). To create a hemagglutinin (HA)-tag version of murine G2A, PCR was performed using the MuN2A-HA-N and MuN2A-HA-C primers (see Table 2). The amplified PCR fragment was subcloned into the pCRII vector (Invitrogen). The insert was then excised with XhoI and NotI and subcloned into the pGD retroviral expression vector at the XhoI and NotI site. Multiple PCR clones were sequenced from both directions to ensure the in-frame fusion of the G2A with the HA-tag engineered at the NotI site of the pGD expression vector.

To obtain the mouse G2A genomic clone, the mouse G2A cDNA was used as a probe to screen a mouse genomic library. The library was made with genomic DNA from mouse strain 129. The genomic DNA was partially digested with MboI, size-fractionated (17–21 kb), and ligated into the BamHI site of DashII arms (Stratagene). At least one positive clone was isolated and the authenticity of the clone was verified by direct sequencing of the genomic DNA and by PCR analysis using primers specific for the gene.

TABLE 2

Oligonucleotides used in the analysis of Murine G2A

| Primer | Sequence, 5'—3' |
| --- | --- |
| MuN2A3'RACE-1 | CAGGACTGGCTTGGGTCATT (SEQ ID NO: 12) |
| MuN2A3'RACE-2 | GTCCACAGAACTCACATAGGA (SEQ ID NO: 13) |
| MuN2A3'-1 | CGCGGATCCGAATTCGGTACCGGTGACTCAGAGGACCAG (SEQ ID NO: 14) |
| MuN2A-HA-N | CGGAATTCTCGAGTCAGGACTGGCTTGGGTCATT (SEQ ID NO: 15) |
| MuN2A-HA-C | ATAGTTTAGCGGCCGCGCAGAGCTCCTCAGGCAGT (SEQ ID NO: 16) |
| Mu+HuN2A+8 | CAAGAAGTGTCCAGAATCCA (SEQ ID NO: 17) |
| N2AGSP1 | GGTGACAGCAGTCCTCTGGT (SEQ ID NO: 18) |
| N2AGSP2 | TAGCGGTCGCAGGAAATGCAG (SEQ ID NO: 19) |
| N2Arandom | TGATTGGTGAACGCCAGG (SEQ ID NO: 20) |
| N2A5 | GCTTTGAGCCCCTGAGGATGAA (SEQ ID NO: 21) |
| T7 | GTAATACGACTCACTATAGGGC (SEQ ID NO: 22) |
| GST-Mu-N2A-N5' | GTCGGATCCATGAGATCAGAACCTACCAAT (SEQ ID NO: 23) |
| GST-Mu-N2A-N3' | GTCGAATTCTCACAGGACCACTCTGCTCTC (SEQ ID NO: 24) |
| M13 Reverse | CAGGAAACAGCTATGAC (SEQ ID NO: 25) |
| Anchor Primer | CUACUACUACUAGGCCACGCGTCGA-CTAGTACGGGIIGGGIIGGGIIG (SEQ ID NO: 26) |
| MuN2A3'HA | GCCGAATTCTCAAACTCCGGC (SEQ ID NO: 27) |

TABLE 2-continued

Oligonucleotides used in the analysis of Murine G2A

| Primer | Sequence, 5'–3' |
| --- | --- |
| MuN2Aflag5 | CCGGAATTCGGCCACCATGGACTACAAGGACGACGATG-ACAAGAGATCAGAACCTACCAATGCA (SEQ ID NO: 28) |
| MuN2A5'Eco | CCGGAATTCCTAGAGGCCACCATGAGATCAGAACCTAC-CAAT (SEQ ID NO: 29) |

EXAMPLE 5

Isolation of Human G2A cDNA and Genomic Clones

The murine G2A was used as a probe to screen a human spleen cDNA library (ClonTech, Palo Alto, Calif.) to isolate the human homologue. The probe was labeled as described above. The hybridization was performed in Rapid-hyb buffer (Amersham Life Science, Arlington Heights, Ill.) for 2 hrs at 65° C. The filters were washed twice with 2×SSC and 0.1% SDS at 65° C. for a total of 40 mins. At least four positive clones were isolated after screening $1.5 \times 10^6$ plaques. Sequence analysis revealed that these were overlapping clones containing an open reading frame encoding a protein of 380 amino acids with a calculated molecular weight of 42 kD. Multiple clones were sequenced from both directions to ensure the accuracy of the sequence. PCR was then used to amplify the full length human G2A from the human spleen cDNA library using the gene-specific primers HuN2A+N1HA (5' primer) and HuN2A-C (3' primer) (see Table 3). To generate a HA-tag version of human G2A, the 5' primer HuN2A+N1HA and 3' primer HuN2A-HA-C were used (see Table 3). The amplified PCR fragment containing the full length human G2A cDNA (SEQ ID N: 3) was purified using Geneclean™ and cloned into the pCRII vector. Multiple clones were sequenced using T7, SP6, N2AGSP2, Mu+HuN2A+8, HuN2AE+2A, HuN2AC-8, and HuN2A+6 primers (Table 2) to ensure the accuracy of the sequence. Alignment of the mouse and human G2As show that they are about 70% identical to each other at the amino acid level.

TABLE 3

Oligonucleotides used in the analysis of human G2A

| Primer | Sequence, 5'–3' |
| --- | --- |
| HuN2A+N1HA | CGCTCGAGTGGGAGCAAATGCGGAGCGAG (SEQ ID NO: 30) |
| HuN2A-C | TTAGCGGCCGCTCAGCAGGACTCCTCAATCAG (SEQ ID NO: 31) |
| Hun2A-HA-C | TTAGCGGCCGCGCAGGACTCCTCAATCAGCCTC (SEQ ID NO: 32) |
| Mu+HuN2A+8 | CAAGAAGTGTCCAGAATCCA (SEQ ID NO: 33) |
| HuN2A+9 | ACCAGCCACAGTGCCCATG (SEQ ID NO: 34) |
| HuN2AE+2A | TGCCACTCTGGGTCATCTAT (SEQ ID NO: 35) |
| HuN2A+6 | CGGTGGTTGTCATCTTCCTA (SEQ ID NO: 36) |
| T7 | GTAATACGACTCACTATAGGGC (SEQ ID NO: 37) |
| M13 Reverse | CAGGAAACAGCTATGAC (SEQ ID NO: 38) |

EXAMPLE 6

Northern Analysis

RNA was purified using the Ultraspec RNA isolation system (Biotecx laboratories, Inc., Houston, Tex.). To examine the expression level of a gene of interest, a DNA fragment of the gene was labeled using the Prime-it II random primer labeling kit (Stratagene). Northern blotting was performed as previously described (Schneider at al., Cell 54:787–793, 1993). Briefly, the RNA samples were fractionated in an agarose gel (1% agarose, 20 mM phosphate, pH 7.0, 7% formaldehyde), transferred to Nitro-Pure nitrocellulose transfer membrane (Micron Separations, Inc. Westborough, Mass.) using 20×SSC. The blot was baked at 80° C. for 2 h and prehybridized in the prehybridization buffer (50% formamide, 5×SSC, 1×Denhardt's, 50 mM phosphate stock buffer and 0.25 mg/ml salmon sperm DNA) for 4 h. The blot was then hybridized overnight at 42° C. with the probe in 8 ml prehybridization buffer and 2 ml 50% dextran sulfate. The blot was washed once with 2×SSC, 0.1% SDS at room temperature for 30 min, and once with 2×SSC, 0.1% SDS at 60° C. for 30 min. The blot was exposed to x-ray film at −70° C. To assess whether G2A affects hematopoietic cell transformation by BCR-ABL, a bone marrow transformation assay was applied to quantitatively measure the kinetics of the BCR-ABL-mediated transformation in the presence or absence of G2A. Retroviral-mediated expression of BCR-ABL in primary murine bone marrow cells results in the outgrowth of stromal cell-dependent pre-B cultures (McLaughlin et al., 1987). The growth rate of pre-B cells from infected marrow is directly dependent on the strength of the tyrosine kinase activity. To monitor the protein level of ectopically-expressed G2A, a chimeric G2A-GFP fusion protein was generated whose level could be quantitatively measured by FACS. The assay was performed as described in the following example.

EXAMPLE 7

Murine Bone Marrow Transformation Assay and Reconstitution of Irradiated Mice Fresh bone marrow cells from the tibias and femurs of 3- to 4-week-old BALB/c mice were isolated and infected with retrovirus encoding either the WT BCR-ABL p185 along with the G2A-GFP fusion protein (pMSCV G2A-GFP IRES p185 WT) or GFP as a control. IRES is an internal ribosome entry binding site element which improves the yield of the expressing clones. The anti-sense version of G2A-GFP and GFP were also used as controls. The cells were plated at a density of $5 \times 10^6$ cells per 6-cm dish in RPMI containing 10% fetal bovine serum and β-mercaptoethanol ($5 \times 10^5$ M) as previously described (McLaughlin et al., Mol. Cell. Biol. 9:1866–1874, 1989). The viral stocks were prepared as described (Goga et al., Cell 82:981–988, 1995). Liquid cultures were plated in triplicates and monitored for pre-B cell growth. Transformed pre-B-lymphoid cells were counted at various days following infection. The Expression of G2A-GFP and GFP were confinned by FACS analysis.

Figure 7:
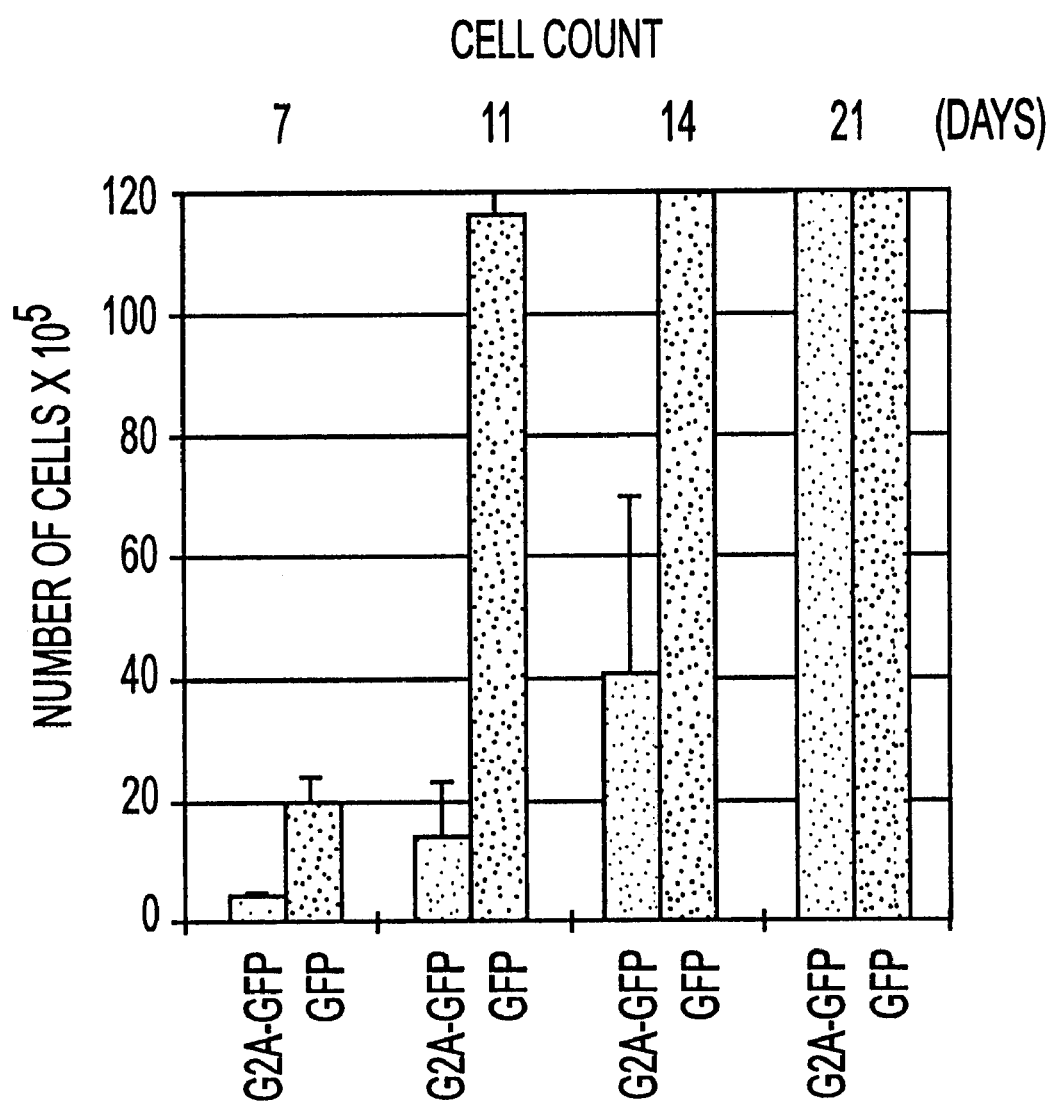
FIG. 7 shows the effect of G2A on the growth of bone marrow cells transfected with a retroviral vector encoding BCR-ABL and G2A-GFP or BCR-ABL and GFP (control).

During the first two weeks of the assay, G2A expression with BCR-ABL delayed the induction of pre-B cell outgrowth compared to BCR-ABL plus GFP or the G2A-GFP anti-sense control. Bone marrow cultures transformed by BCR-ABL in the absence of G2A reached confluency (>1× $10^7$ cells per 3 ml culture) within 1 ½ weeks, whereas it took nearly three weeks to reach saturation in the presence of G2A (FIG. 7). Similar results were obtained in three independent experiments. This indicates that G2A slows the transformation process of BCR-ABL in lymphoid cells. Because G2A is linked to GFP, protein levels could be measured in these cultures during the three-week period by FACS. GFP alone did not significantly change its expression levels; however, G2A-GFP protein levels decreased gradually and after three weeks were nearly undetectable (FIG. 8). This counter-selection against B cells expressing high levels of G2A strongly suggests an anti-oncogenic effect of G2A as seen in fibroblasts.

Since G2A is not natively expressed but induced by BCR-ABL in pre-B cells, it was determined whether the expression of G2A was regulated during different states of B cell development. B lymphocytes are generated from hematopoietic stem cells by successive steps of differentiation during which a diverse repertoire of antigen receptors are generated by immunoglobulin gene rearrangement. The initiation of D-J rearrangement occurs in the early pro-B cells and at the pre-B cell stage, intact heavy chains are produced. The light chain genes then undergo rearrangement resulting in the expression of a complete IgM protein on the surface of immature B cells which then differentiate into IgM and IgD-expressing mature B cells capable of responding to antigen.

EXAMPLE 7A

Transcriptional Regulation of G2A in B Cells

To examine the expression of G2A, mouse bone marrow B cells were fractionated into pro-B, pre-B, immature B and mature B cells to examine the expression of G2A in different developmental compartments in lymphoid cells. A semi-quantitative RT-PCR method was used to measure the RNA levels of G2A. The G2A transcript is almost exclusively present in pro-B cells which coincidentally have the highest proliferation potential and are undergoing recombination. Extended PCR cycles revealed a low level of G2/A transcript in pre-B, immature B and mature B cells.

Figure 9:
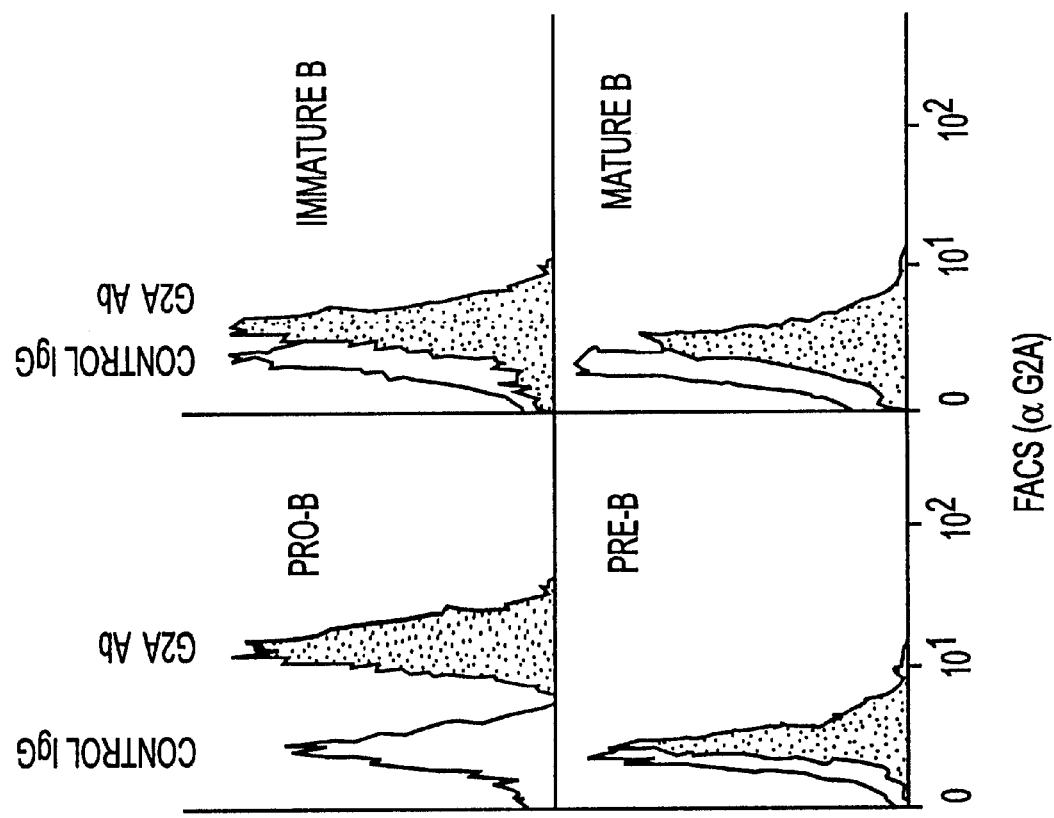
FIG. 9 is a flow cytometry profile showing the expression of G2A in pro-B, pre-B, immature B and mature B cells.

Rabbit polyclonal anti-G2A antibodies were used to examine the protein level of G2A in the same pro-B, pre-B, immature B and mature B cell fractions. High levels of G2A protein were detected in pro-B cells whereas very weak staining was present in the other three fractions of B cells using FACS (FIG. 9). These results show that the mRNA level of G2A corresponds to G2A protein level and that the effect of G2A may be predominantly restricted in pro-B cells.

To determine whether natural stimuli could activate G2A in more mature B cells, we used a human B cell line (Ramos) as a model system in which G2A expression is at a basal level. Ramos cells (and Jurkat cells, a human T cell line) were activated by anti-IgM antibodies to examine whether activation of B cell receptors (BCR) induced G2A transcription.

EXAMPLE 8

Regulation of G2A Transcription During B and T Cell Activation

Human B cells (Ramos) and T cells (Jurkat) were grown in RPMI 1640 containing 10% fetal calf serum to a density of 2×$10^6$ cells/ml. The cells were resuspended at a density of 2×$10^8$ cells/ml in serum-free RPMI immediately prior to stimulation. For activation of Ramos cells with anti-IgM, goat anti-IgM was added to cell suspension (0.5 ml) at a final concentration of 10 µg/ml. After 0 min, 5 mim, 7 hours and 24 hours at 37° C. RNA was isolated.

For activation of Ramos and Jurkat cells with ionomycin and PMA, iomomycin and PMA were added to the cells to a final concentration of 2 µg/ml and 20 ng/ml, respectively, and RNA was isolated at 0, 3, 6, 24 and 48 hours. For activation of Jurkat cells by anti-CD3 and CD28 antibodies, respectively, each 10 cm plate was coated with anti-CD3 (6.25 µg) and anti-CD28 (12.5 µg) antibodies (Sigma, St. Louis, Mo.). The harvested at 0, 3, 6, 24 and 48 hours after activation and RNA was isolated.

For RT-PCR, 5 µg total RNA from each sample was used to synthesize the first strand cDNA using the Superscript™ preamplification system (GIBCO BRL). Ten percent of the first strand cDNA synthesis product was then used for PCR. The HuN2A–C1 (SEQ ID NO: 28) and HuN2A+6 (SEQ ID NO: 33) primers were used for amplification of the human G2A fragment. A control set of primers, G3PDH control amplimers set for human and mouse (5'-ACCACAGTCCATGCCATCAC-3'; SEQ ID NO: 39 and 5'-TCCACCACCCTGTTGCTGTA; SEQ ID NO: 40), were used to ensure that equal amounts of template were used. PCR was performed in a 50 µl reaction mixture containing 1×PCR buffer (20 mM Tris-HCl, pH 8.4, 50 mM KCl; GIBCO), 1.5 M $MgCl_2$, 0.4 mM of each DNTP, 10 pmol of each primer, 0.5 µl Taq DNA polymerase (GIBCO) and 2 µl of first strand cDNA synthesis product. The cDNA was denatured at 94° C. for three minutes. PCR was performed by 35 cycles of denaturation at 94° C. for 0.5 min, annealing at 58° C. for 1 min, and elongation at 72° C. for 2 min.

The G2A transcript was barely detectable in unstimulated Ramos cells. The human G2A was found to be transcriptionally upregulated in B cells within 4 hours of activation by anti-IgM antibody, suggesting that strong B cell receptor crosslinking regulates the expression of G2A. Upregulation of the G2A transcript was also observed in simultaneous addition of ionomycin and PMA to B cells to increase the intracellular calcium levels and to activate Protein Kinase C, respectively, resulted in increased levels of G2A mRNA. Time course analysis of the G2A transcript demonstrated that induction of G2A mRNA. Time course analysis of the G2A transcript demonstrated that induction required between 2 and 4 hours with these activators. Activation of Ramos cells with CD40 ligand also upregulated the G2A transcript. In addition, exposure of Ramos induced the transcription of G2A. However, no dramatic alteration in G2A transcript induced the transcription of G2A. However, no dramatic alteration in G2A transcript levels was observed in Jurkat cells upon activation by PMA plus ionomycin or anti-CD3 plus CD28 antibodies. These data suggest that the human G2A may play a role during B cell activation. As a control, glyceraldehyde 3-phosphate dehydrogenase (G3PDH) control amplimer set was used to ensure that equal amounts of templates were used for RT-PCR. Taken together, these results suggest that the G2A may play a role upon B cell activation. The transcriptional activation of G2A may either be involved in apoptosis of B cells or proliferation and/or differential of B cells.

It has been shown that transcription of the tumor suppressor gene p53 can be induced by ionizing radiation. Since G2A functions like a tumor suppressor gene and its DNA damaging agents which activate many of the tumor suppressor genes could also induce the expression of G2A.

EXAMPLE 8A

Induction of G2A Expression by DNA-damaging Agents

Varying doses of X-rays were used to irradiate Ramos cells and total RNA samples were extracted after overnight incubation. The G2A transcript was induced in a dosage dependent manner and reached a maximum at about 9 Gy. Since ionizing radiation causes single and double strand DNA breaks, it was also determined whether outer DNA-damaging damaging agents could also activate G2A transcription. A broad range of agents were chosen which may cause different types of DNA lesions: UV irradiation which induces the formation of thymidine dimers; chemical agents which inhibit de novo DNA precursor synthesis (hydroxyurea, 5-fluorouracil); chemical agents which directly block DNA synthesis (cytosine arabinoside, taxol, etoposide); or agents which intercalate into the DNA double helix (doxorubicin). The G2A transcript was found to be upregulated in response to all of the DNA damaging agents tested. suggesting that the induction of G2A may be due to activation of a general sensor of DNA damage.

EXAMPLE 9

Insertion of Mouse and Human G2As into Expression Vectors

G2A cDNA was inserted into several eukaryotic expression vectors. Any of these constructs can be used to transfect eukaryotic cells, preferably mammalian cells, for production of recombinant G2A using methods well known in the art. Such methods are described in, for example, Sambrook et al. (*Molecular Biology: a Laboratory Manual*, Cold Spring Harbor Laboratory, 1988; Ausubel, *Current Protocols in Molecular Biology*, 1989). Such eukaryotic cells include Rat-1, NIH 3T3, 293T, CHO, COS-7 and BHK cells. The G2A can also be inserted into a baculovirus expression vector which is used to infect Sf9 insect cells using methods well known in the art.

N-terminal flag-tagged mouse G2A in the pCRII vector (Invitrogen) was used for in vitro transcription and translation of mouse G2A and for making probes for Northern, S1 or in situ analysis. Reverse transcription of RNA into first strand cDNA was performed using RNA isolated from bone marrow cells transformed with WT BCR-ABL. PCR was performed using 10 pmol of MuN2Aflag5 and MuN2A3'-1 primers (Table 2) in 50 µl reaction mixture containing 1 xpfu buffer (20 mM Tris-HCl, pH 8.75, 10 mM KCl, 10 mM $(NH4)_2SO_4$, 2 mM $MgSO_4$, 0.1% Triton X-100, 100 µg/ml BSA) (Sigma). The cDNA was first denatured at 94° C. for 3 min. PCR was performed by 35 cycles of denaturation at 94° C. for 0.5 min., annealing at 62° C. for 1 min. and elongation at 75° C. for 3 min. The amplified PCR product was cloned into the pCRII vector (Invitrogen) according to the manufacturer's instruction.

The pSRα-Flag-G2A tk Neo expression vector is a retroviral expression vector for expression of mouse and human G2As in mammalian cells. In this construct, the Neo gene is under control of the herpes simplex virus thymidine kinase (tk) promoter for selection of infected cells with G418. The EcoRI insert from pCRII-Flag-Mu-G2A was excised and cloned into pSRα-Flag-G2A tk Neo at the EcoRI cloning site upstream of the TK promoter.

pCRII-Mu-G2A, the untagged version of pCR-Flag-Mu-G2A, was used for in vitro transcription and translation, and for making probes of Northern, S1 or in situ analysis. For construction of this vector, RT-PCR was performed using primers MuN2A5'Eco and MuN2A3'-1 (Table 2) using the protocol described for pCRII-Mu-G2A. The amplified PCR product was cloned into the pCRII vector. In vitro transcription and translation were performed using the TNT-coupled reticulocyte lysate system (Promega, Madison, Wis.) according to the manufacturer's instructions. The in vitro transcription and translation of Mu-G2A revealed a protein product having a molecular weight of about 42 kDa which is similar to the calculated molecular weight of mouse G2A.

pCRII-Mu-G2A-HA, the C-terminal HA-tagged version of mouse G2A was used for in vitro transcription/translation and for labeling proves for Northern, S1 or in situ analysis. For construction of this vector, RT-PCR was performed using primers MuN2A5'Eco and MuN2A3'HA using the plasmid vector pGD-Mu-G2A-HA containing the HA-tagged version of murine G2A. The PCR product was cloned into the pCRII vector (Invitrogen).

For construction of pMu-G2A-GFP, the mouse G2A was fused to the N-terminal green fluorescence protein (GFP) in the pEGFP-N1 vector (Clontech). The murine G2A was amplified using primers specific for murine G2A and fused in frame with GFP in the pEGFP-N1 vector. The expression of the Mu-G2A-GFP fusion protein was confirmed by FACS analysis. The fusion protein will allow following the expression of murine G2A in mammalian cells and functional analysis of the G2A. Similarly, for pEGF-Hu-G2A-GFP, human G2A was fused to the N-terminal green fluorescence protein (GFP) in the pEGFP vector. The human G2A is amplified using primers specific for human G2A and fused in frame with GFP in the pEGFP vector. The fusion protein allows following the expression of human G2A in mammalian cells and functional analysis of the G2A.

EXAMPLE 10

Acceleration of Leukemogenesis in vivo by BCR-ABL

One day prior to reconstitution, severe combined immunodeficient (SCID) mice were sublethally irradiated with 275 rads. Whole bone marrow was isolated and infected with retrovirus as described above. Three hours post-infection, the bone marrow was injected intravenously into the tail veins of recipient SCID mice. Animals are monitored for signs of sickness over a twelve-week period. Sick mice are sacrificed and tissues are analyzed for BCR-ABL expression by Western Blotting. Blood and spleen samples are analyzed by flourescence activated cell sorting (FACS). Blood smears are analyzed by Wright/Giemsa staining. Mice which were injected with WT BCR-ABL exhibit significantly more leukemogenesis than mice injected with the SH2 mutant.

To evaluate the effect of BCR-ABL-regulated genes on the oncogenic potential of BCR-Abl, a soft agar fibroblast colony formation assay was used. BCR-ABL confers anchorage-independent growth of rodent fibroblasts (Rat-1) in soft agar and the numbers of colonies quantitatively reflects its transformation potency (Lugo et al., *Mol. Cell. Biol.* 9:1263–1270, 1989). This assay is described below.

EXAMPLE 11

G2A Functions as a Tumor Suppressor Gene

The G2A, G2A-GFP, or G2A indicator cell lines were generated by infection of Rat-1 fibroblasts with helper-free retroviruses followed by selection in G418 (0.4 mg/ml) for approximately 1–2 weeks. The expression of G2A-GFP and GFP were confirmed by FACS analysis using a FACScan (Becton Dickinson). Transformation by various oncogenes was measured using a soft agar assay as described (Lugo et al., supra.). Briefly, the indicator cell lines were plated at a density of $6 \times 10^4$ cells/6 cm dish overnight. Infection was performed for 3 hours at 37° C. using 1 ml of virus stock with 8 μg/ml polybrene. Two days post-infection, cells were harvested and plated in agar at a density of $1 \times 10^4$ cells/6 cm dish in duplicate. Dishes were re-fed at one week and colonies were counted after three weeks. Colonies greater than 0.5 mm in diameter were scored positive.

G2A or Neo-expressing Rat-1 cell lines were also generated by retroviral infection and G418 selection, followed by superinfection with a retroviral stock expressing BCR-ABL. Similar percentages of cells were infected by BCR-ABL-expressing retroviruses as shown by FACS analysis and Western blotting.

Most of the genes isolated by the RDA screen had no discernible effects on the oncogenic potential of BCR-ABL. However, G2A strongly antagonized the ability of BCR-ABL to form colonies in soft agar. As listed in Tables 4A–B, overexpression of G2A suppressed the number of agar colonies induced by BCR-ABL p185 approximately five fold. G2A epitope-tagged with GFP still retained some ability to block BCR-ABL-mediated transformation in Rat-1 cells. G2A also blocked agar colonies induced by Gag-BTK*, an activated version of Bruton tyrosine kinase, and the transcription factor, Myc. Interestingly, G2A failed to block transformation mediated by v-ABL or the serine kinase oncogene v-Mos. v-ABL and v-Mos may transform cells by mechanisms distinct from BCR-ABL, Myc and Gag-BTK*. Since BTK has been shown to play a critical role in B cell development (Tsukada et al., *Cell* 72:279–290, 1993; Rawlings et al., *Immunological. Rev.* 138, 1994), the ability of G2A to block Gag-BTK* transformation also suggests that the G2A may also be a regulator of BTK dwing B cell development. Similarly, overexpression of the G2A gene suppressed the transformation of bone marrow cells. In addition, in vivo tumor formation and leukemogenesis assays can be used to analyze the effect of G2A on malignant phenotypes induced by various organisms. Transfection or infection of cells in vitro, ex vivo or in vivo with expression constructs, preferably retroviral or adenoviral vector constructs, encoding G2A results in inhibition of cell proliferation. In a preferred embodiment of the invention, bone marrow is isolated from an individual with leukemia by standard methods, and the bone marrow cells are infected with the retroviral construct encoding G2A as described herein. The bone marrow is then returned to the patient. Overexpression of G2A in the bone marrow cells inhibits further leukemogenesis and results in a significant clinical improvement.

TABLE 4A

| Oncogene | Rat-1 | Rat-1/G2A |
|---|---|---|
| Ø | 0 | 0 |
| BCR-ABL p185 | >1300 | 226 ± 40 |
| v-ABL | 552 ± 28 | 444 ± 24 |
| Myc | >1300 | 388 ± 20 |

TABLE 4B

| Oncogene | Rat-1/GFP | Rat-1/G2A-GFP |
|---|---|---|
| Ø | 9 ± 1 | 2 ± 1 |
| BCR-ABL p185WT | >1300 | 608 ± 40 |
| v-ABL | 432 ± 64 | 496 ± 16 |
| Gag-BTK* | 88 ± 12 | 3 ± 1 |
| v-Mos | 224 ± 16 | 172 ± 20 |

Rat-1/Neo cells exhibited a prominent elongation phenotype typical of transformation by BCR-ABL. G2A blocked this gross morphological change by BCR-ABL. When these same cell populations were plated in agar, wild type BCR-ABL alone gave rise to more than 1,000 colonies after three weeks. In contrast, BCR-ABL, co-expressed with G2A, yielded more than 5-fold fewer colonies indicating that G2A antagonizes BCR-ABL-mediated transformation. Evaluation of agar colonies recovered and expanded in liquid culture by FACS analysis showed that the cells that grew in agar lose expression of G2A but not BCR-ABL. Thus, G2A has an anti-proliferative effect on transformation.

To determine whether the G2A was involved in the regulation of cell cycle progression, Rat-1 fibroblasts were infected with retrovirus expressing G2A gene as described in the following example.

EXAMPLE 12

G2A Induces Cell Cycle Arrest in Rat-1 Cells During Mitosis

Rat-1 cells were selected with G418 (0.4 mg/ml) for one week and grown to either subconfluence or confluence. The cells were harvested by trypsinization and pelleted by centrifugation. The cells were then resuspended in Vindelov's stain (5 mM Tris, pH 7.4, 5 mM NaCl, 0.05% NP-40, 0.04 mg/ml propidium iodide, 5 μg/ml RNase) and incubated on ice for 15 min in the dark. Flow cytometric analysis was performed using FACScan (Lysis II program). As shown in Table 5, expression of G2A increases the percentage of cells in the G2/M phase of the cell cycle. Examination of Rat-1 cells expressing the G2A under the microscope revealed a higher percentage of cells with bi- or poly-nuclei (approximately 5–10% versus less than 1% observed in parental Rat-1 cells), suggesting that G2A-expressing cells were likely to be arrested at the anaphase of mitosis. Taken together, these data suggest that the G2A may function as a tumor suppressor gene and is involved in cell cycle arrest during mitosis. The biological properties of the G2A share similarities with p53, a tumor suppressor gene. Both G2A and p53 negatively regulate cell growth and induce cell cycle arrest. Interestingly, their expressions are both upregulated by DNA damage-inducing agents such as X-rays. The ability of certain oncogenes to induce the expression of G2A and the ability of G2A to block the oncogenic potential of these genes suggest that the G2A may comprise a self-defense mechanism for cells to counter ill-fated transformation phenotypes.

TABLE 5

|  | G1 | S | G2/M | dead cells |
|---|---|---|---|---|
| Rat-1 (subconfluent) | 60% | 14% | 25% | 1% |
| Rat-1/G2A (subconfluent) | 47% | 14% | 37% | 2% |
| Rat-1 (confluent) | 64% | 11% | 24% | 1% |
| Rat-1/G2A (confluent) 49% | 12% | 36% | 3% | |

EXAMPLE 13

Figure 10:
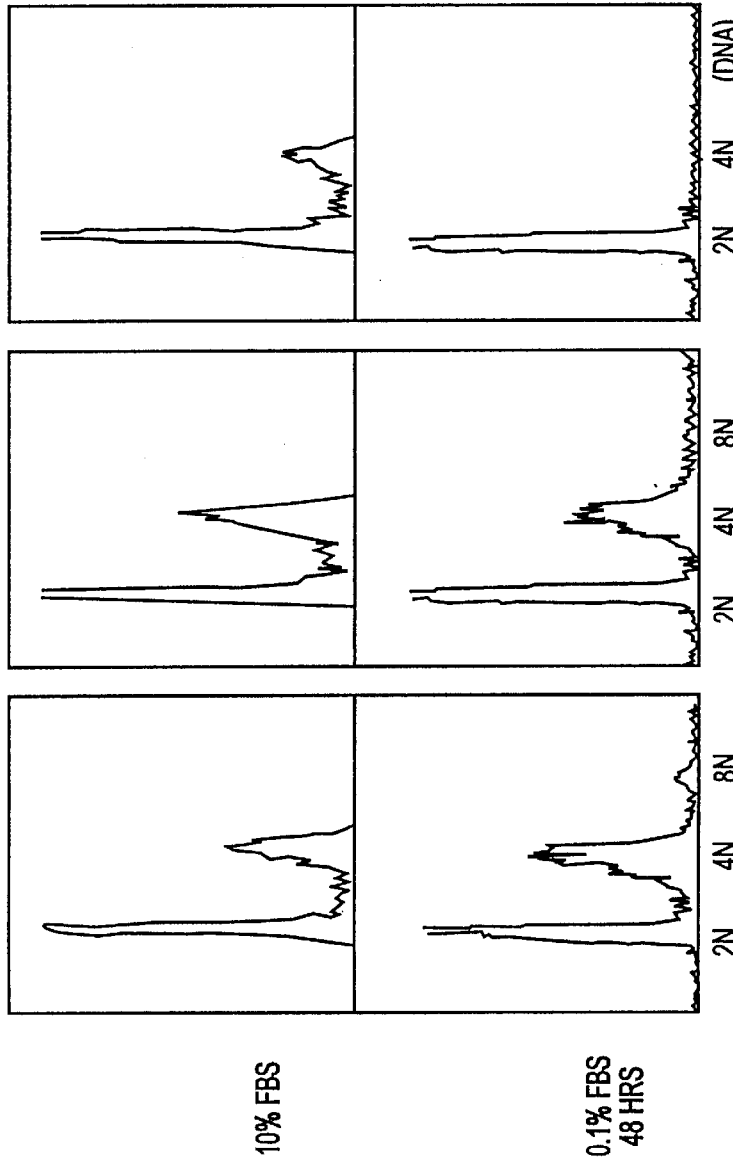
FIG. 10 shows that G2A arrests cells at the G2/M transition upon serum withdrawal.

G2A Blocks the Progression of Mitosis in NIH3T3 Cells 15 The anti-oncogenic effect of G2A in fibroblasts and lymphoid cells, as well as the The anti-oncogenic effect of G2A in fibroblasts and lymphoid cells, as well as the induction of G2A by cell cycle arrest-associated DNA damaging agents suggested that G2A may be involved in cell cycle regulation. To investigate this possibility, retroviruses expressing G2A, G2A-GFP fusion protein or a GFP control were used to infect NIH3T3 cells which are easily infectable (>90% of infection). Transient infection with a G2A retrovirus reproducibly increased the fractions of cells at G2/M by approximately 10% under normal growing conditions (10% FBS), strongly indicating that G2A arrests cells at G2/M. This percentage increase is comparable to that caused by overexpression of p53. To further examine whether G2A confers a G2/M block under serum starvation conditions, NIH3T3 cells expressing G2A, G2A-GFP fusion or GFP control were cultured in the presence of 0.1% FBS for 48 hours. Cells were harvested and the DNA content analyzed by FACS. Two days after serum starvation, 95% of the control cells expressing GFP alone contained 2N DNA content, suggesting that these cells were arrested at G1 upon growth factor deprivation. However, cells expressing G2A or G2A-GFP fusion protein still exhibited a large percentage of cells with 4N DNA content (39% and 34%, respectively), suggesting that G2A blocks the exit of cells from G2/M during growth factor deprivation (FIG. 10). An increase in the 8N DNA content which is accentuated during growth factor deprivation, and an increase of approximately 5–10% of multiple nuclei in cells expressing G2A or G2A-GFP, were also observed (FIG. 10). This suggests that although there is still endoduplication of DNA in cells expressing G2A, these cells failed to undergo cytokinesis suggesting a potential additional role of G2A in perturbing the mitotic spindle checkpoint.

Examination of the G2A primary sequence reveals the presence of a "destruction box" found primarily in cyclin gene products which may serve as a recognition motif for the conjugation of ubiquitin. Cytosolic ubiquitinated cyclins are degraded by the multisubunit 26S proteosome (Hochstrasser, 1996). There is some evidence that certain GPCRs such as yeast Ste2 are ubiquitinated which is required for their internalization for subseguent degradation. A more recent report demonstrated the role of ubiquitinization of a GPCR for internalization of the signal while it escaped degradation by the proteasome (Terrell et al., *Molecular Cell* 1:193–202, 1998). The presence of the "destruction box" in G2A raised the possibility that G2A may be ubiquitinated and down regulated or internalized via the ubiquitin pathway.

EXAMPLE 14

Degradation of G2A via the Ubiquitin Pathway

Figure 11:
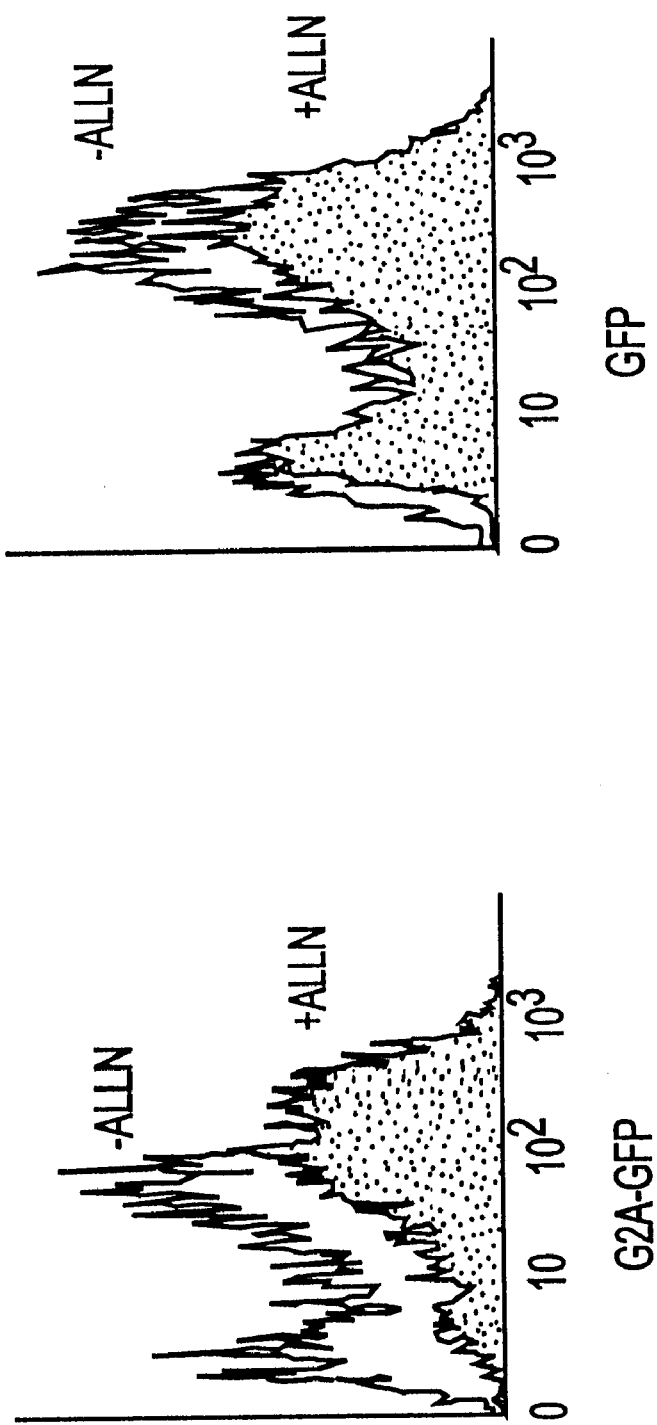
FIG. 11 is a flow cytometry profile showing that the ubiquitin-proteasome inhibitor increases the G2A protein level.
Figure 12:
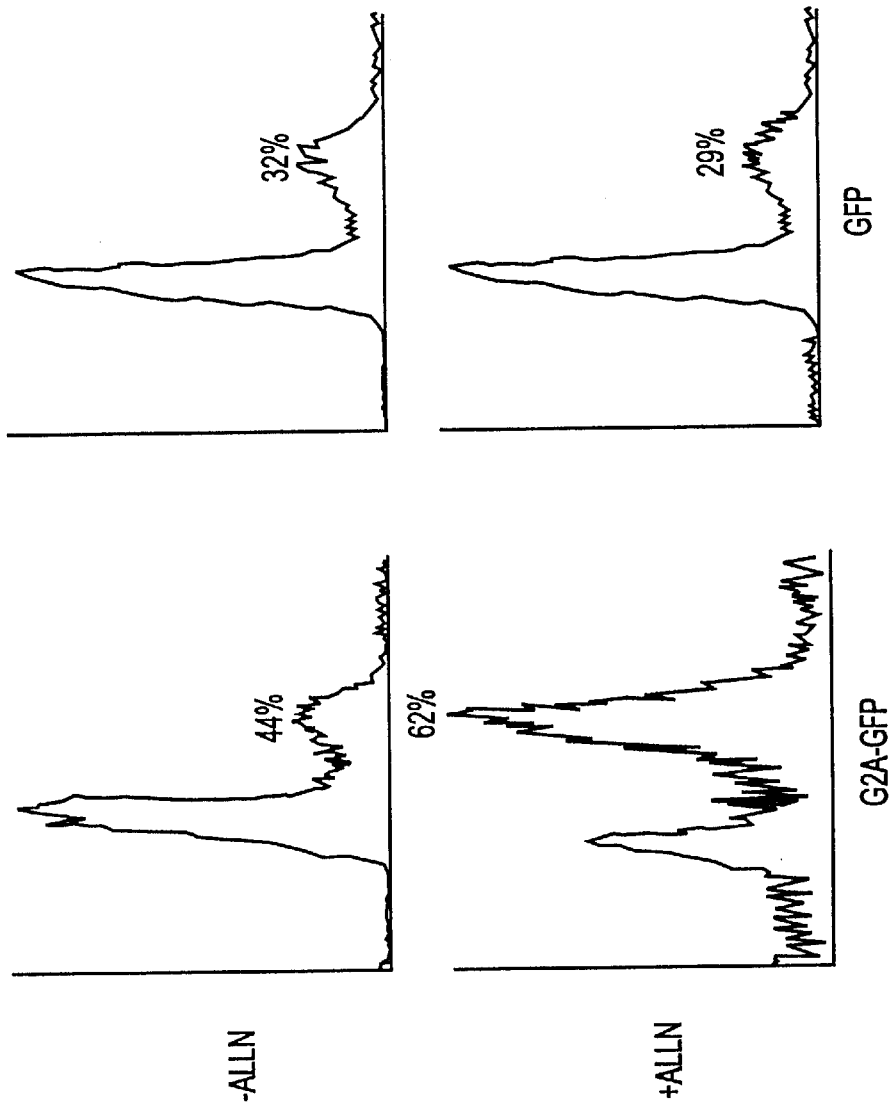
FIG. 12 shows that a ubiquitin pathway inhibitor potentiates the G2/M transition block by G2A.

N-acetyl-L-leucinyl-L-leucinyl-L-norleucinal (ALLN) is a potent inhibitor of the 20S proteasome which prevents the degradation of ubiquitinated proteins via the 20S proteasome. To determine whether the addition of ALLN can increase the protein level of G2A and potentiate the G2/M block mediated by G2A, mouse fibroblast cells were infected with retroviruses expressing G2A-GFP or GFP. After overnight incubation with a four fold lower dose of the inhibitor (50 $\mu$M) than used in previous reports, cells were harvested and analyzed by FACS for GFP. ALLN increased the protein level of G2A-GFP by 4–5 fold as measured by the log fluorescence intensity (FIG. 11). These data suggest that partial inhibition of the 20S proteasome activity stabilized or increased the overall protein level of G2A. The increased protein level of G2A by ALLN also potentiated the G2/M block (from 44% to 62%) (FIG. 12). Similar results were also obtained with another related peptide aldehyde, N-acetyl-L-leucinyl-L-leucinyl-L-methional (ALLM).

Loss of the putative "destruction box" may stabilize G2A, leading to an increase in protein level or a cellular counter-selection against an overactive G2A, leading to a decrease in overall protein level. This mutation may also result in a misfolded, non-functional receptor which is degraded even before it localizes to the plasma membrane. It is also possible that the destruction box and the ubiquitination of G2A are required for its normal function such as membrane localization, ligand activation or internalization. In addition, the ubiquitin mutant resulted in lower protein concentration.

A number of genes including p53 and Abl have been implicated in G2/M checkpoint regulation. p53 has been shown to delay the transition of G2/M by preventing the activation of Cdc25, which is required for the activation of Cdc2/Cyclin B complex. Although the precise role of Abl in the G2/M checkpoint is unknown, it has been shown that Abl physically interacts with ATM and activation of the Abl kinase activity by DNA damage is dependent on ATM. Abl is also interesting because knockout mice exhibit a lymphopenic syndrome suggesting a more significant cell cycle regulatory role in lymphoid cells than in other cell types.

EXAMPLE 15

Abl and p53 are not Required for the G2/M Block by G2A

Figure 13:
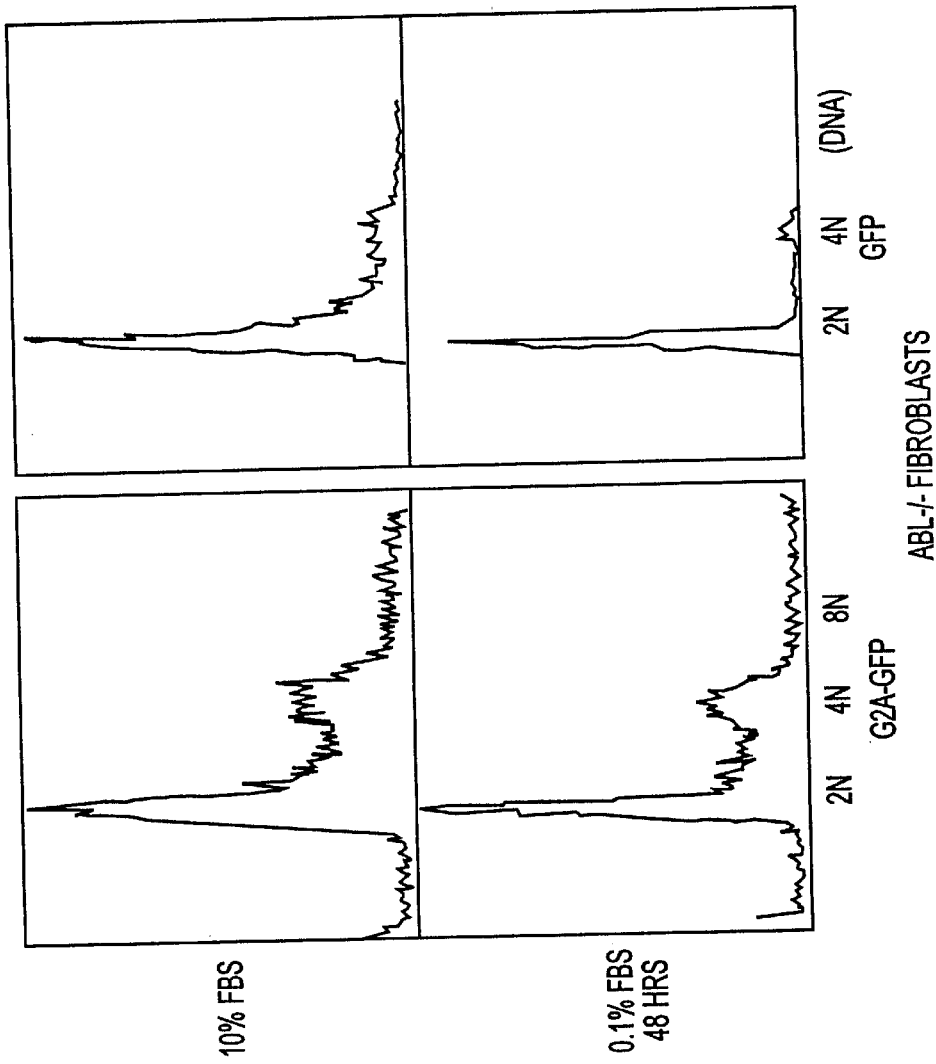
FIG. 13 shows that the G2/M block by G2A is independent of ABL.

To determine whether p53 or Abl are involved in G2A-mediated G2/M arrest, we examined whether overexpression of G2A induces G2/M arrest in fibroblasts lacking p53 or Abl. In an Abl knockout cell line, overexpression of G2A-GFP increased the percentage of cells at G2/M by approximately 15% in the presence of 10% FBS when compared to NIH3T3 cells (FIG. 13). A high percentage of cells expressing G2A were still arrested at G2/M (39%) after serum starvation (0.1% FBS) compared to GFP-expressing cells (14%) (FIG. 13), suggesting that Abl expression is not functionally required for G2/M arrest by G2A.

Figure 14:
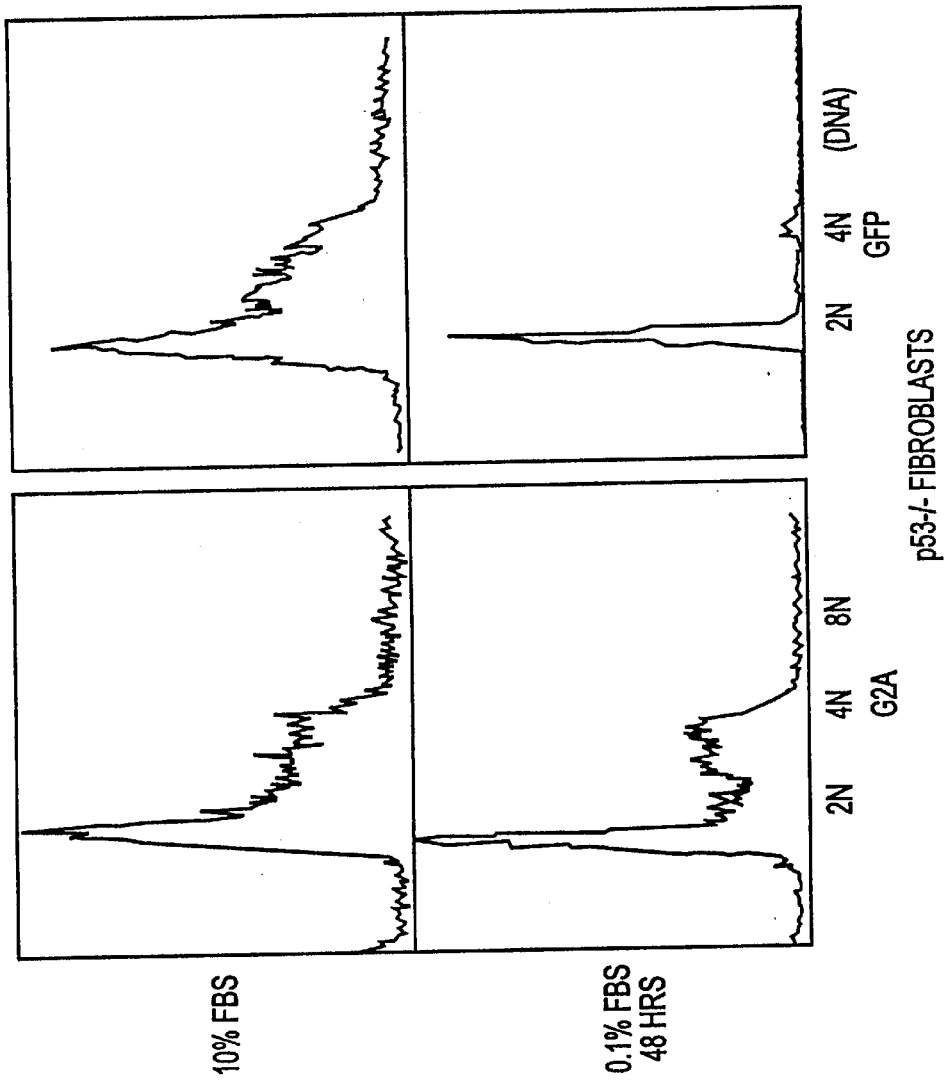
FIG. 14 shows that the G2/M block by G2A is independent of p53.

Similar experiments were preformed on a p53–/– fibroblast cell line to determine whether p53 is required for the G2/M block by G2A. FACS analysis of p53–/– fibroblasts resulted in an unusual distribution over the cell cycle consistent with the significant role of p53 as a cell cycle regulator. Overexpression of G2A in the absence of p53 did not significantly increase the percentage of cells at G2/1M under normal growing conditions (10% FBS) (FIG. 14). Serum starvation for 48 hours revealed a large percentage of G2A-expressing cells still arrested at G2/M (33%) compared to GFP-expressing cells (16%) (FIG. 14), suggesting that p53 is not required for the G2/M arrest by G2A.

Since p53 is a universal sensor of DNA damage and serves as a transcription factor to induce the expression of a number of genes (such as p21, 14-3-3) in response to DNA damage, it was determined whether p53 was required for the induction of G2A in response to ionizing radiation in lymphocytes. Bone marrow cells were isolated from WT and p53-knock out mice and incubated with IL-7 and SLF (steel factor) to stimulate the outgrowth of pre-B cells. These pre-B cells were then irradiated with varying doses of X-rays. After overnight incubation following irradiation, total RNA was isolated and a semi-quantitive RT-PCR was performed as described above. The level of the G2A transcript was low in actively growing non-irradiated pre-cells, further supporting that active proliferation signals are not sufficient to induce G2A expression. The G2A transcript was induced by X-ray in both the WT and the p53−/− mice, suggesting that the induction of G2A by gamma irradiation is not dependent on p53.

The ability of G2A to arrest the cell cycle at G2/M in the absence of p53 and abl suggested signaling via a unigue pathway. To understand the molecular mechanism responsible for the G2A-mediated G2/M block, we determined whether G2A signals through the essential Maturating Promoting Factor (MPF) component Cdc2. Compounds such as caffeine have been used to reverse the DNA damage-induced inhibition of Cdc2 and release G2/M arrest. While the precise mode of action by caffeine is unknown, it has been suggested that caffeine activates Cdc25 and results in dephosphorylation of Thr14/Tyr15 in Cdc2, leading to the activation of the Cdc2/cyclin B complex and driving the completion of mitosis.

Figure 15:
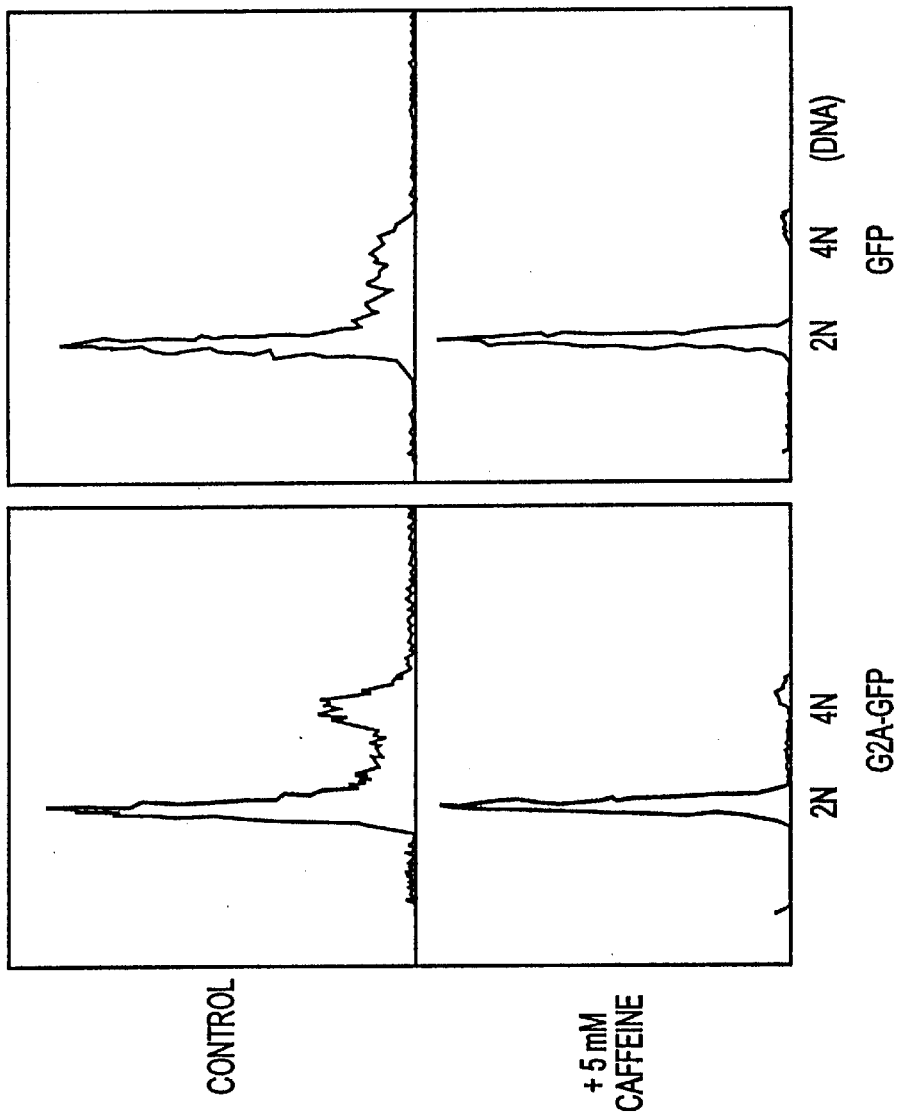
FIG. 15 shows that caffeine alleviates the G2/M block by BSA.

Mouse fibroblasts infected with retroviruses expressing a G2A-GFP fusion protein or GFP were incubated in the presence of 5 mM caffeine. The cells were harvested after overnight incubation for FACS analysis. G2A-expressing cells exhibited a high percentage at G2/M compared to GFP-expressing cells in the absence of caffeine. Overnight incubation with 5 mM caffeine relieved the G2/M arrest suggesting that the G2A-mediated G2/M block is upstream of Cdc2 (FIG. 15).

EXAMPLE 17

Chromosomal Localization of Human G2A

Fluorescene in situ hybridization (FISH) was performed using human metaphase cells prepared from phytohemagglutinin (PHA)-stimulated peripheral blood lymphocytes to determine the gene locus. The G2A probe was a human genomic fragment cloned into the Lambda DASH vector (Stratagene) at the SAII site. FISH was performed as described by Rowley et al. (*Proc. Natl. Acad. Sci. U.S.A.* 87:9368–9372, 1990). A biotin-labeled probe was prepared by nick-translation using Bio-16-dUTP (Enzo diagnostics). Hybridization was detected with fluorescein-conjugated avidin (Vector Laboratories, Burlingame, Calif.), and chromosomes were identified by staining with 4,6-diamidino-2-phenylindole-dihydrocbloride (DAPI). The human G2A was found to be localized to chromosome 14, band q32.3. It has been shown that chromosomal abnormalities at 14q32.3 are associated with a wide variety of human cancers. For example, rearrangements of bands 14q32.3 and 19p13.3 were found in patients with multiple myeloma and plasma cell leukemia (Taniwaki et al., *Leukemia and Lymphoma* 21:25–30, 1996; Fujino et al., *Cancer Res.* 55:3246–3249, 1995). In addition, deletion mapping analysis has strongly suggested that loss of a putative tumor suppressor gene at 14q32 may be involved in the pathogenesis of ovarian, endometrial, colorectal and bladder cancers (Bandera et al., *Cancer Res.* 57:513–515). Chromosomal abnormalities have also been reported at 14q32 in other human diseases such as desmoplastic infantile ganglioma and mantle cell lymphomas (Bergsagel, *Proc. Natl. Acad. Sci. U.S.A.* 93:13931–13936, 1996; Vaandrager et al., *Blood* 88:1177–1182, 1996). Based on the ability of G2A to suppress transformation phenotypes of oncogenes, G2A is a candidate tumor suppressor gene whose loss of expression may be at least partially involved in the progression of certain cancers.

G2A-MEDIATED CYTOSKELETAL/ACTIN REORGANIZATION STUDIES

Materials

Hoechst 33342 was from Molecular Probes, Inc., Oregon. Rhodamine conjugated Phalloidin, anti-vinculin monoclonal antibody (VIN-11-5) and Bradykinin were from Sigma (St. Louis, Mo.). PDGF-BB was from Upstate Biotechnology. Aminomethylcoumarin (AMCA) conjugated secondary anti-rabbit antibody was from Jackson Immuno Research Laboratories, Inc. All other fluorescently conjugated secondary antibodies were from Pharmingen (San Diego, Calif.). Anti-RhoA monoclonal antibody was from Santa Cruz Biotechnology.

Cell Lines and Plasmids

Swiss 3T3, NIH 3T3, 293T and Gα knockout (KO) MEFs (G·13 KO: 35, G·q/11 KO: 37, G·12 KO) were cultured in Dulbecco's modified Eagle's medium (DMEM) supplemented with 10% fetal calf serum (FCS). 293T cells were transfected Cell-cycle Analysis NIH 3T3 or Ba/F3 cells were infected with retroviruses encoding G2AiresGFP, G2A.GFP or GFP. Cells were harvested 24 hours later and incubated with 1 μg/ml Hoechst 33342 at 37° C. for 10 minutes. DNA content was measured using a Becton Dickinson FACS Vantage SE machine and GFP positive G2/M fractions were sorted and cytospun onto microscope slides. G2/M preparations were stained with Giemsa and cells with visible chromosomes scored.

Western Blotting

For western blotting with affinity purified G2A antiserum, $1 \times 10^6$ cells were lysed in RIPA buffer (50 mM Tris, pH7.2, 500 mM NaCl, 10 mM $MgCl_2$, 1% Triton X-100, 0.1% SDS, 0.5% sodium deoxycholate, in 1 mM PMSF and 10 μg/ml each of aprotinin, leupeptin and soybean trypsin inhibitor) at 4° C. (cold room) on a rotating wheel for 1 hour. Lysates were cleared by centrifugation at 10,000 rpm at 4° C. for 10 minutes and supernatants were run on 10% SDS-Polyacrylamide (SDS-PAGE) gels. SDS-PAGE gels were electroblotted onto PVDF membranes (Immobilon™ -P, Millipore) at 120 mAmps for 2 hours. PVDF membranes were incubated in blocking buffer (TBS/0.05% Tween-20, 5% non-fat dried milk) for 1 hour followed by incubation with affinity purified G2A antiserum (1:500) in blocking buffer for 1 hour. Membranes were subjected to 4×10 minute washes in blocking buffer followed by incubation with Biotechnology, Inc.) (1:5000) for 1 hour. Membranes were washed 4 times (10 minutes each) in TBS/0.05% Tween-20 and signal was detected by enhanced chemiluminescence (ECL) following the manufacturers recommended (Amersham).

Microinjection and Immunocytochemical Staining

Cells for microinjection and growth factor treatment were plated at a density of $10^4$/ml onto 13 mm acid-washed glass coverslips. Two days later, cells were serum starved for 16 hours prior to microinjection. Plasmids in 50 mM HEPES (pH 7.4), 40 mM NaCl were injected into the nuclei of cells using an Eppendorf semi-automated injector assembled on an inverted Zeiss Axiovert 10 microscope. Approximately 200–250 cells were microinjected on each coverslip and returned to the incubator for a further 4 hours or as indicated. Unless otherwise indicated, all constructs were microinjected at a cocentration of 10 ng/μl. Coverslips were subsequently rinsed once in PBS and fixed in 4% paraformaldehyde/PBS for 10 minutes at room temperature. Coverslips were washed in PBS and permeabilized by incubation with 0.2% Triton X-100/PBS for 5 minutes at room temperature prior to incubation with 1:100 Gα13 antiserum, 1:100 9E10 monoclonal antibody or 1:100 anti-vinculin monoclonal antibody in PBS/0.15% Triton X-100, 25 mg/ml BSA at room temperature for one hour in a humidified chamber. Coverslips were washed 4 times in PBS ensuring complete drainage of excess PBS after each wash. Coverslips were incubated with 1:100 dilution of Rhodamine conjugated goat anti-mouse secondary antibody (for vinculin), AMCA conjugated goat anti-mouse secondary antibody (for MYC epitope tagged Rho family GTPases), or AMCA conjugated goat anti-rabbit secondary antibody (for Gα13) for one hour at room temperature in a humidified chamber. Where appropriate, 0.2 μg/ml Rhodamine conjugated Phallaidin was included in the secondary antibody incubations. Coverslips were washed 4 times in PBS followed by one wash in $H_2O$; after each wash, excess fluid was drained from the coverslips. Coverslips were mounted by inverting them onto 5 μl moviol on a microscope slide. Coverslips were examined on a Zeiss axiophot microscope using a Zeiss 40×1.3 oil immersion objective. In all experiments, greater than 90% of injected cells exhibited the described response.

Affinity Precipitation of RhoA-GTP

Swiss 3T3 fibroblasts were infected with MSCV GFP or MSCV G2AiresGFP retroviruses and 24 hours later serum starved for 12 hours. Cells were subsequently trypsinised, washed in ice cold TBS, and lysed in RIPA buffer (50 mM Tris, pH7.2, 500 mM NaCL, 10 mM $MgCl_2$, 1% Triton X-100, 0.1% SDS, 0.5% sodium deoxycholate, 1 mM PMSF and 10 μg/ml each of aprotinin, leupeptin and soybean trypsin inhibitor). In addition, aliquots of cells were analysed by FACS for GFP expression and found to be over 90% GFP positive. Lysates normalized for protein content were incubated on ice for 1 hour with 40 μg of a GST fusion protein (prepared as described in Ren et al., *EMBO J.* 18:578–585, 1999) comprising the RhoA GTP binding domain of Rhotekin (GST-RRBD) immobilized on Glutathione-agarose beads. Beads were washed 4 times in Tris buffer containing 150 mM NaCl, 10 mM $MgCl_2$, 1% Triton X-100, 10 μg/ml each of aprotinin, leupeptin and soybean trypsin inhibitor, and 100 μm PMSF. Affinity precipitates and aliquots of total lysates were run on a 10% SDS-PAGE gel, transferred onto PVDF membrane, and western blotted with a monoclonal antibody against RhoA following the protocol described above.

SRF-Luciferase Assays

Wild-type and Gα KO Murine Embryonic Fibroblasts (MEFs) were cotransfected with 0.2 μg of the reporter plasmid pSRF-Luc (Stratagene, Inc.), 0.2 μg of pCIS-Galactosidase and 0.6 μg of pET G2A or 0.6 μg of pET GFP (totaling 1 μg DNA) by the "Superfect" system (Life Technologies, Inc.). 48 hours after transfection, cells were harvested, washed with PBS, and subsequently lysed in 400 μl Luciferase assay buffer (Promega, Madison, Wis. Lysates, normalized for β-galactosidase activity, were subjected to Luciferase assays using a Monolight 2010 luminometer (Analytical Luminescence Laboratory) according to the manufacturers protocol (Luciferase Assay System; Promega).

EXAMPLE 18

G2A Delays Cell-cycle Progression in Mitosis

To extend the initial observation of accumulation of G2A overexpressing cells in the G2/M cell-cycle compartment, the consistency of this phenotype in other fibroblastic cell lines was established by Propidium Iodine (PI) staining and Fluorescence Activated Cell Sorter (FACS) analysis. Similar increases in the G2/M fraction in NIH 3T3, RAT1, Swiss 3T3 and Murine Embryonic Fibroblasts (MEFs) were observed less than 48 hours following their infection with MSCV retroviruses encoding G2A containing a carboxy terminal Green Fluorescent Protein (GFP) tag (MSCV G2A.GFP) previously described (Weng et al., *Proc. Natl. Acad. Sci U.S.A.* 95:12334–12339, 1998). Identical results were obtained with retroviruses encoding G2A linked via an Internal Ribosome Elongation Sequence (IRES) to GFP (MSCV G2AiresGFP).

In order to establish whether G2A induces accumulation of cells within G2 or M, NIH 3T3 cells were infected with MSCV GFP or MSCV G2AiresGFP retroviruses and incubated with the viable DNA stain Hoechst 33342 24 hours later. GFP positive G2/M (4n) fractions were FACS sorted based on their DNA content, subsequently spun onto glass slides, and analyzed by light microscopy to score the number of G2 and their significantly greater frequency in G2/M preparations from G2A expressing cells, demonstrating that G2A induces a mitotic delay.

To determine whether G2A expression induces mitotic delay in a non-fibroblastic cell-type, murine Pro-B lymphoblastoid Ba/F3 cells (Palacios et al. *Cell* 41:727–734, 1985) were infected with MSCV GFP, MSCV G2AiresGFP or MSCV G2A.GFP retroviruses and subjected to identical cell-cycle analysis to that described above. Compared to control GFP expressing Ba/F3 cells, an increased fraction of mitotic cells was observed within G2/M preparations obtained from cells expressing G2A (21% vs 11%).

EXAMPLE 19

G2A Induces Morphological Alterations in Fibroblasts

Figure 16:
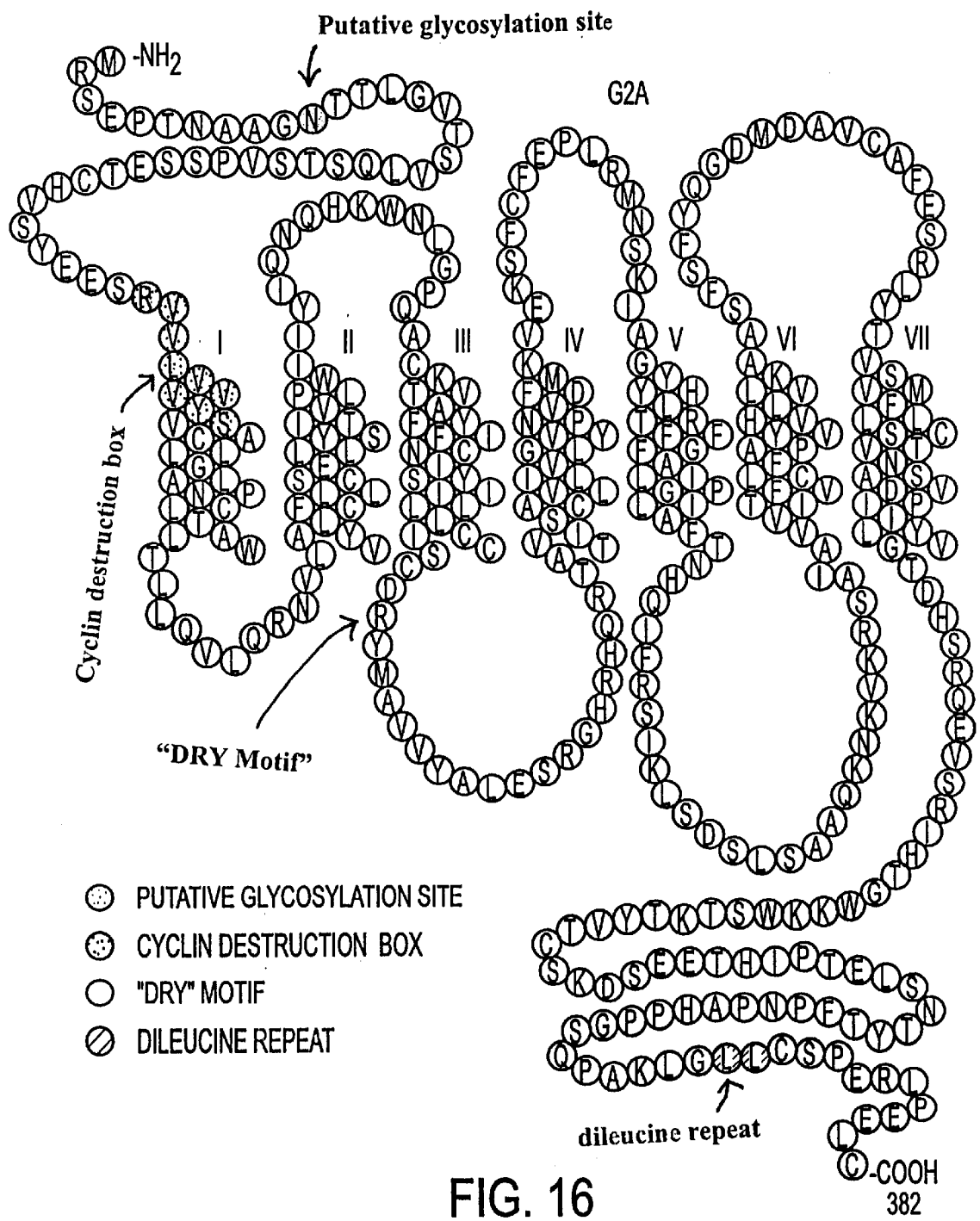
FIG. 16 is a schemtic of G2A (SEQ ID NO: 2) in the cell membrane. G2A contins a putative N-linked glycosylation site in the N-terminal extracellular domain and a putative "destruction box" (RVVLVVVYS; amino acids 39–47 of SEQ ID NO: 2) that is similar to that of human cyclin A, which serves as a recognition motif for ubiquitin conjugation.

Dramatic morphological alterations were readily apparent in fibroblasts less than 48 hours following their infection with G2A encoding retroviruses, including reduced cell spreading and suppression of contact inhibition. G2A expressing cells in sub-confluent cultures appear elongated and tightly packed, with a significantly greater proportion detached and rounded. In addition, these morphological changes were quite distinct from those induced in fibroblasts following their infection with retroviruses encoding V12 RAS. A mutant form of G2A in which an alanine residue has been substituted for the arginine residue within the highly conserved "DRY" motif present in the second intracellular loop was incapable of producing similar morphological changes, consistent with its well documented requirement for the coupling of GPCRs to their heterotrimeric G protein (Rosenthal et al., *J. Biol. Chem.* 268:13030–13033, 1993; Zhu et al., *Mol. Pharmacol.* 45:517–523, 1994). A schematic diagram of G2A structure and primary amino acid sequence showing the "DRY" motif is shown in FIG. 16.

An important consideration is that the mitotic delay induced by G2A may be a consequences of the perturbation of cell/substratum interactions associated with the morphological changes induced in adherent fibroblastic cell-types. Results obtained in Ba/F3 cells suggest that this is not the case. Ba/F3 cells are independent of adhesion for their growth and viability and ectopic expression of G2A also leads to the accumulation of mitotic cells. It was therefore speculated that the cell-cycle and morphological changes induced by G2A are causally related, and having established the point of cell-cycle delay in mitosis, the status of signal transduction molecules involved in the regulation of cytoskeletal architecture was examined. Among these, Rho family GTPases play a central role, relaying signals from cell surface receptors including GPCRs, receptor tyrosine kinases (Boguski et al., *Nature* 366:643–654, 1993) and integrins Giancotti et al., *Science* 285:1028–1032, 1999) to the actin cytoskeleton, thus establishing coordinated dynamic and spatial regulation of actin rearrangement in response to environmental cues as diverse as mitogenesis, differentiative/maturational stimuli, cell adhesion, cell/cell interaction and chemoattraction (Gutkind et al., *Oncogene* 17:1331–1342, 1998). Additionally, a role for RhoA in cytokinesis has been implicated in several studies (Kosako et al., *Oncogene* 18:2783–2788, 1999; Mabuchi et al., *Zygote* 1:325–331, 1993).

EXAMPLE 20

G2A Induces Assembly of Actin Stress Fibers

In order to avoid prolonged expression of G2A during which biological adaptation and selection may contribute to the cellular phenotype, microinjection of Swiss 3T3 cells was employed, a system in which acute regulation of expression is readily achieved in a cell line routinely utilized to study cytoskeletal regulation and actin rearrangement, and whose compliment of expressed Gα subunits is known (Gohla et al., *J. Biol. Chem.* 273:4653–4659, 1998). Initially, G2A encoding constructs (pEXV3 G2A and pEXV3 G2A.GFP) were transfected into 293T cells to ensure expression of G2A and G2A.GFP proteins. Western blotting with affinity purified rabbit antiserum raised against carboxy terminal sequences of G2A revealed proteins of expected size, with no evidence of protein instability/degradation.

Nuclear microinjection of pEXV3 G2A and pEXV3 G2A.GFP at 10 ng/μl into Swiss 3T3 fibroblasts elicited the formation of actin stress fibers and assembly of focal adhesion complexes). A construct encoding a nuclear GFP protein (pEXV3 GFP) was co-injected at 10 ng/μl in all experiments apart from those performed with G2A.GFP to identify productively injected cells. In this and all other experiments described below, approximately 200–250 cells were microinjected and all possible microscopic fields were examined. Both G2A and G2A.GFP consistently induced indistinguishable cytoskeletal rearrangements with similar kinetics (examination of cells at time-points ranging from 1 hour to 12 hours following injection) and at similar concentrations of injected plasmid (down to 0.2 ng/μl). Examination of the cytoskeletal architecture in Swiss 3T3 fibroblasts 1 hour following their microinjection with a construct encoding V12 RAS (pEXV3 V12 RAS) revealed only lamellipodial actin rearrangement consistent with the involvement of Rac as a key downstream target of RAS signaling (Scita et al., *Nature* 274:27562–27566, 1999). A correlation between morphological changes induced by G2A expression and its ability to induce actin stress fibers in fibroblasts was also established, in that the putative loss of function G2A "DRY" mutual failed yo elicit cytoskeletal reorganization into stress fibers.

EXAMPLE 21

G2A Induced Stress Fiber Assembly Requires RhoA.

Microinjection of constitutively active mutants of RhoA into Swiss 3T3 fibroblasts induces the formation of actin stress fibers and focal adhesions (Ridley et al., *Cell* 70:389–399, 1992). In addition, RhoA functions as a downstream component of signaling pathways initiated by ligand stimulation of the G protein-coupled LPA receptor leading to stress fiber assembly (Barry et al., *J. Cell Sci.* 107:2033–2045, 1994). To assess the requirement for RhoA activity in the induction of stress fibers by G2A, a construct encoding a dominant negative mutant form of RhoA (pEXV3 N 19 RhoA) was co-injected with pEXV3 G2A into Swiss 3T3 cells. Co-expression of N19 RhoA inhibited G2A mediated stress fiber induction, with injected and non-injected cells demonstrating indistinguishable cytoskeletal organization. This demonstrates that RhoA signaling is required for the induction of stress fiber assembly by G2A.

The fact that G2A induced the formation of actin stress fibers in the absence of other distinct cytoskeletal structures within an hour of microinjection suggests that this effect is unlikely to be mediated by the sequential activation of CDC42, Rac and Rho (Nobes et al., *Cell* 81:53–62, 1995). Indeed, within an hour of microinjection V12 RAS induced the formation of actin structures consistent with Rac activation only. To either directly address the requirement for CDC42 and Rac activity, a construct encoding either a dominant negative mutant of CDC42 or Rac (pEXV3 N17 CDC42 or pEXV3 N17 Rac) was coinjected with pEXV3 G2A. Expression of N17 CDC42 or N17 Rac did not inhibit the assembly of stress fibers induced by G2A. Importantly, microinjection of pEXV3 N17 CDC42 or pEXV3 N17 Rac inhibited Bradykinin induced formation of filopodia and PDGF induced membrane ruffling (Lamellipodia) respectively.

EXAMPLE 22

G2A Activates RhoA

Limitations associated with the use of N19 RhoA include its impact upon normal cytoskeletal integrity, irrespective of the presense or absense of a stimulating factor. In other words, one can establish a requirement for RhoA in the formation of cytoskeletal structures, but one cannot unequivocally ascribe it a role as a downstream effector of G2A. A direct biochemical approach was therefore employed to assay the activity of RhoA in cellular lysates obtained from Swiss 3T3 cells 36 hours following their infection with MSCV GFP or MSCV G2AiresGFP retroviruses. Additionally, this approach addresses the possibility that induction of stress fiber assembly in G2A expressing fibroblasts is an indirect secondary consequence of altered integrin dependent signaling associated with their morphological transformation (Ren et la., *EMBO J.* 18:578–585, 1999) rather than a direct consequence of RhoA activation by G2A. Briefly, lysates were incubated with a GST fusion protein containing the RhoA-GTP binding domain of the RhoA effector Rhotekin (GST-RRBD) to affinity precipitate active GTP-bound RhoA (Ren et al., supra.). Cell populations were over 90% GFP positive by FACS analysis prior to lysis. Affinity precipitates were subsequently run on 10% SDS-PAGE gels, transferred onto PVDF membranes, and western blotted with an antibody against RhoA. As a control, incubation with 1 μg/ml LPA for 5 minutes stimulated an increase in RhoA-GTP levels in both cell populations. Elevated levels of RhoA-GTP were observed in Swiss 3T3 cells infected with MSCV G2AiresGFP compared to that in cells infected with control MSCV GFP retroviruses. Although G2A may signal through several distinct effectors, RhoA activation leading to cytoskeletal rearrangement has been identified as a pathway downstream of G2A.

EXAMPLE 23

Induction of Rho-dependent Cytoskeletal Rearrangement by G2A is Mediated by Gα13

The requirement for individual G proteins in the induction of stress fiber assembly by G2A was also examined. Microinjection of pEXV3 G2A.GFP into wild-type, Gαq/11 KO MEFs elicited stress fiber assembly with identical frequency and kinetics. However, Gα13 KO and Gα12/Gα13 KO MEFs did not accumulate abundant stress fibers in response to microinjetion.

To exclude the possibility that the unresponsiveness of Gα13 KO MEFs to G2A is due to secondary mutations other than ablation of Gα13 function, Gα13 and Gα12/Gα13 deficient fibroblasts were reconstituted with functional Gα13 by coinjecting a construct encoding Gα13 (pET Gα13). While microinjection of pEXV3 GFP or pEXV3 G2A.GFP into Gα13 KO MEFs failed to elicit assembly of stress fibers above that observed in non-injected cells, coinjection of pET Gα13 with pEXV3 G2A.GFP resulted in the formation of abundant actin stress fibers. Importantly, reconstitution of Gα13 alone had no significant effect upon cytoskeletal organization in these cells, but restored their responsiveness to G2A in terms of actin stress fiber assembly. Identical results were obtained with the Gα12/Gα13 KO MEFs.

The Gα coupling profile of G2A includes Gα13, through which G2A mediates activation of RhoA leading to cytoskeletal reorganization and transcriptional activation of SRF. The involvement of Gα12 in G2A induced SRF activation suggests that G2A may also couple to this G protein.

Microinjection of plasmids encoding G2A elicits rapid induction of stress fiber assembly in Swiss 3T3 cells which is inhibited by coexpression of a dominant negative mutant of RhoA. The fact that the G2A "DRY" mutant is inactive in these assays and fails to induce morphological changes in NIH 3T3 cells suggest that indirect mechanisms such as sequestration of signaling intermediates, including other heterotrimeric G proteins, by ectopically expressed G2A or its heterodimerization with other GPCRs (Hebert et al., *Biochem. Cell Biol.* 76:1–11, 1998) are not responsible for the biological effects described in this report. Indeed, our results demonstrate a direct signaling pathway from G2A leading to RhoA via Gα13. Activation of RhoA by G2A is directly demonstrated by assay of RhoA-GTP levels in G2A expressing cells and the role of Gα13 was established indirectly by its requirement for Rho dependent cytoskeletal and transcriptional responses to G2A expression in Gα13 deficient MEFs. While the well documented morphological alterations induced in fibroblasts expressing constitutively activated mutants of RhoA or Gα13 (Khosravi-Far et al., *Mol. Cell Biol.* 15:6443–6453, 1995; Vara Prasad et al., *Oncogene* 9:2425–2429, 1994) suggests that deregulation of RhoA activity by G2A is responsible for its impact upon cellular morphology reported here, the involvement of RhoA in the mitotic delay induced by overexpression of G2A is consistent with its proposed role in the formation and function of the actin-myosin based contractile ring during cytokinesis (Kosako et al., supra.; Mabuchi et al., supra.; Madaule et al., *Nature* 394:491–494, 1998). In addition, results of targeted disruption of the Gα13 locus in mice also demonstrate a critically important role for this G protein in biological processes dependent upon dynamic and spatial reorganization of the actin cytoskeleton (Offermanns et al., *Science* 275:533–536, 1997). Ablation of Gα13 in mice results in embryonic lethality at around day 9.5 of gestation due to defective angiogenesis, and the chemokinetic response to thrombin is virtually abolished in fibroblastic cells from these embryos, supporting a role for Gα13 in cytoskeletal regulation during migratory responses.

The ability of G2A to induce stress fiber assembly in Gα13 deficient MEFs reconstituted with functional Gα13 rules out the possibility that their initial unresponsiveness to G2A expression was due to adaptive or mutational events incurred during embryonic development or immortalization in vitro. Direct analysis of Gα involvement by labeling activated G proteins with the radiolabeled GTP analogue [.-$^{32}$P] GTP azidoanilide has been used in studies of GPCRs with known ligands or agonists (Offermanns et al., *Meth. Enzymol.* 195:286–301, 1991), but is limited in its application to the study of GPCRs in the absence of a defined ligand/agonist. In addition, as Gα photolabelling is performed with membrane fractions prepared from cells engineered to overexpress the GPCR of interest, study of ligand independent constitutively active GPCRs is difficult as they are probably present at too low a number within the plasma membrane due to their ligand independent desensitization and internalization. Interestingly, a large proportion of the G2A.GFP fusion protein is localized to the cytoplasm, with a pronounced perinuclear pattern suggesting its presence in the Golgi. While this could be due to its overexpression, the same localization pattern is observed at the lowest concentrations of injected plasmid irrespective of the presence or absence of serum, conditions under which G2A.GFP consistently induced cytoskeletal reorganization into stress fibers. In addition, identical localization of the G2A.GFP protein is observed 12 hours following microinjection, suggesting that the failure to detect appreciable amounts of the protein at the plasma membrane of microinjected cells is not due to their examination at a time when newly translated G2A.GFP has not yet been processed and exported to the plasma membrane. Another possibility is that G2A may be a ligand independent receptor subject to continual downregulatory modification and internalization due to its constitutive activity. In addition, sequences homologous to the cyclin destruction box motif (King et al., *Science* 272:1652–1659, 1996) within the amino terminal tail of G2A (Weng et al., *Proc. Natl. Acad. Sci. U.S.A.* 95:12334–12339, 1998) may play a role in the ubiquitin dependent regulation of receptor stability and turnover. This would also influence the subcellular distribution of G2A. Alternatively, the presence of the GFP moiety appended to the carboxy terminal tail of G2A may influence its endocytic sorting.

In addition to their effects upon the actin cytoskeleton, Rho family GTPases also regulate transcriptional events. RhoA has been shown to activate the transcription factor SRF (serum response factor) (Hill et al., *Cell* 81:1159–1170, 1995), which cooperates with ternary complex factors (TCFs) such as Elk-1 and SAP ½ in activating transcription at serum response elements (SREs) within the promoters of growth factor regulated genes such as c-fos (Marais et al., *Cell* 73:381–393, 1993). To demonstrate that G2A mediated activation of RhoA can lead to a defined downstream signaling event other than assembly of stress fibers, transient transcriptional reporter assays were performed in the various Gα KO MEF cell lines. A G2A encoding construct was cotransfected with a reporeter construct comprising the Luciferase (Luc) gene driven by a SRE containing only the SRF responsive sequence (SRF-Luc) (Hill et al, supra.). Consequently, transcriptional activation mediated by MAP kinase phosphorylation of TCFs was eliminated. Although there is considerable variability in the growth rates and transfection efficiencies among these cell lines, preliminary results suggest that transient expression of G2A induces transcriptional activation of SRF-Luc which is inhibited by coexpression of the Rho inhibitor C3 transferase and requires both Gα13 and Gα12. This suggests that G2A may couple to both Ga13 and Gα12.

Taken together with its expression and transcriptional induction in lymphoid cells, the demonstration of Gα13 mediated RhoA activation by G2A has important implications in defining the normal physiological role of G2A. Without wishing to be bound by any particular theory, G2A may play a role in the development or function of lymphoid cells by regulating cytoskeletal architecture and the turnover of focal adhesion complexes following its transcriptional induction in response to certain stimuli. For example, G2A induction may function as a "brake" mechanism ensuring appropriate localization of developing lymphoid precursors and/or immunological activated lymphocytes within microenvironments subject to continual fluctuations in cytokine and chemokine gradients. Such mechanisms exist to ensure normal retention and localization of hematolymphoid progenitors within the bone marrow and to optimize costimulatory cell/cell interactions during immune responses which may otherwise only be transient due to the intrinsic motility of T cells and low number of antigenic complexes on the Antigen Presenting Cell (APC). Alternatively, G2A may play a role in the formation of the immunological "synapse" following antigen receptor/MHC-peptide interaction during which segregation of integrin and antigen receptors into specific areas at cell/cell contacts precedes their reorganization via cytoskeletal mechanisms into clusters mediating sustained signaling (Grakoui et al., *Science* 285:221–227, 1999).

In addition, expression of G2A in the kidney suggests that it may play a role as a regulatory component within the homestatic network governing water and electrolyte balance, plasma protein levels and blood volume. Many of the hormones and polypeptides with critical roles in renal function signal through GPCRs whose expression is restricted to particular regions of the kidney and its vasculature (Weiss, *Cellular Signaling* 10:313–320, 1998). In addition, recent studies have implicated Gα13 Gα12 and RhoA in the regulation of Prostaglandin production and transepithelial ion transport mechanisms (Dermot et al., *Oncogene* 18:7185–7189, 1999). Examination of G2A expression in various renal cell-types will provide some clue as to its possible role, if any, in kidney function.

In conclusion, evidence has been obtained for a signaling pathway from G2A leading to RhoA activation via Gα13, thus implicating a number of biological processes as targets of G2A function.

EXAMPLE 24

G2A Knockout Mice

Figure 17:
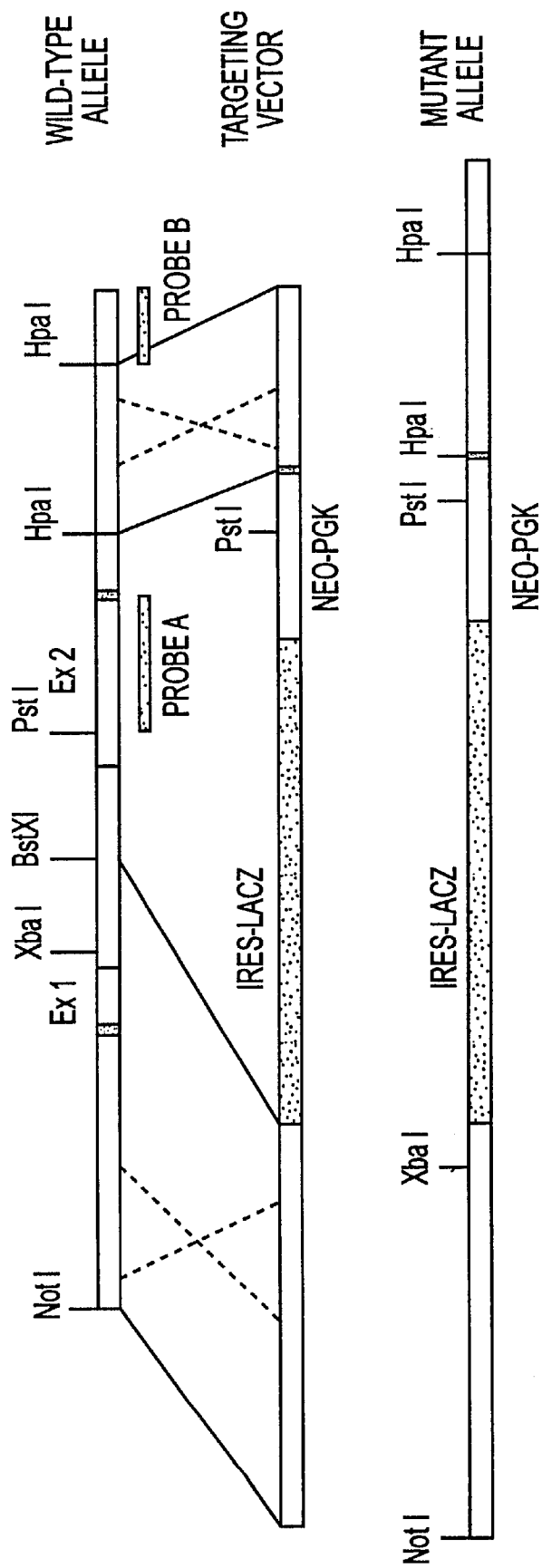
FIG. 17 shows the structure of a portion of the wild-type G2A allele, targeting vector and predicted structure of the correctly targeted mutant allele for generation of G2A knockout mice.

G2A knockout mice were made by methods well known to one of skill in the art using the targeting vector for homologous recombination shown in FIG. 17. Southern blot analysis of tail genomic DNA digested with PstI and hybridized with an external probe to determine the genotypes of mice, or hybridized with an internal probe confirmed the successful deletion of the G2A gene in the knockout mice. The β-galactosidase marker gene was used to determine the tissue specific expression pattern of G2A. Predominant expression was in lymphoid tissues such as the spleen and thymus, with some expression seen in kidney and testis.

G2A-deficient mice were viable, born at the expected Mendelian frequency, and were fertile. Analysis of mice between the ages of 6 to 10 weeks show that they generate normal numbers of hematopetic cells. Phenotypic analysis of bone marrow and thymic lymphocytes indicated a normal pattern of B and T lineage differentiation. There were no gross macroscopic differences in different organs between the G2A+/+ and G2A-/- mice. Histological analysis of brain, heart, kidney, spleen, skin, small & large intestine, thymus, Peyer's patch, lymph nodes, testis, pancreas, adrenal gland, lung, bone marrow, skeletal muscle, and liver did not reveal morphologic differences between the wild-type and mutated mice. G2A-deficient mice were capable of isotype switching and normal production of immunoglobulin isotypes. They were also able to mount comparable antibody responses to T-cell dependent and T-cell independent inert antigens and live Listeria and *Bordetella pertussis*.

EXAMPLE 25

T-cell Activation Studies

Thymic T cells were fractionated into CD4+/CD8+; CD4-/CD8-; CD4+/CD8- and CD4-/CD8+. The G2A transcript was measured by RT-PCR analysis. The transcript was present in all of these T-cell fractions. Peripheral T cells were purified from lymph nodes and spleen of G2A-/- and G2A+/+mice. They were then activated by either αCD3ε cross-linking (5μg/ml) or ConA treatment (10 μg/ml). Total RNA was isolated prior or post activation. RT-PCR was then performed using primers specific for murine G2A cDNA. Glycerol-3-phosphate dehydrogenase (G3PDH) was used as a control to ensure that equal amounts of template were used for RT-PCR. The αCD3ε-and ConA-stimulated cells from the wild-type mouse (G2A+/+) expressed G2A, while the cells from the knockout mouse (G2A-/-) did not express G2A, thus confirming that the G2A knockout was successful.

EXAMPLE 26

Rate of Leukemogensis in Mice Receiving BCR-ABL Transduced Bone Marrow Cells

Figure 18:
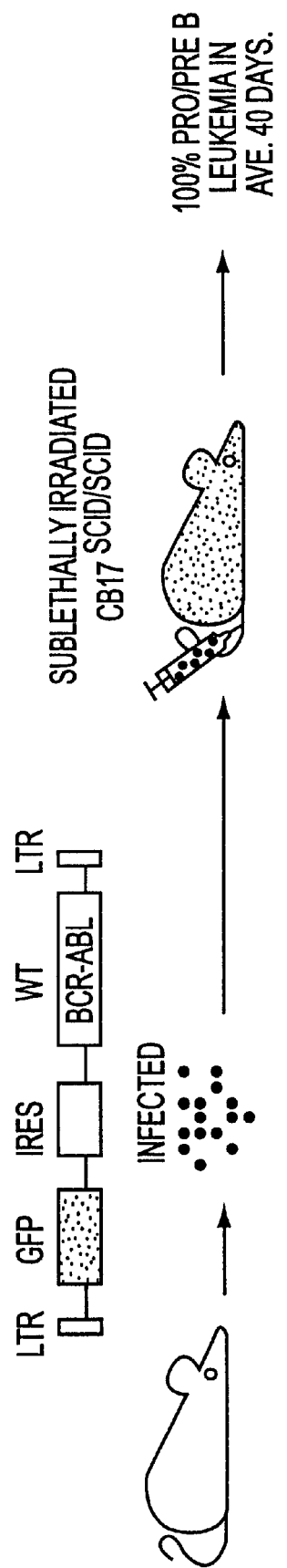
FIG. 18 is a schematic diagram showing the generation of P185 BCR-ABL-induced leukemia in severe combined immunodeficiency (SCID) mice.
Figure 19:
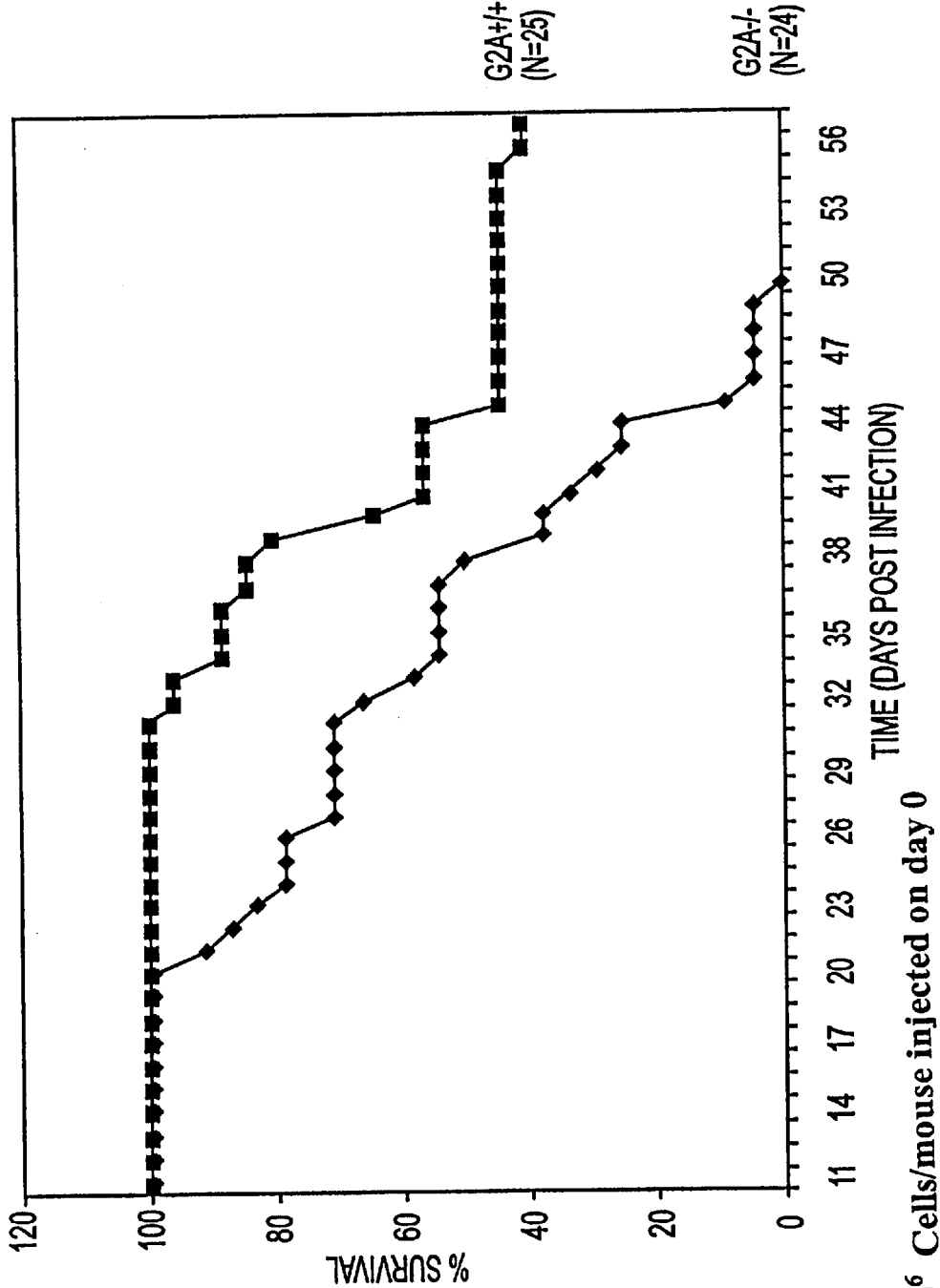
FIG. 19 is a graph showing the acceleration of P185 BCR-ABL induced leukemia in G2A−/− pre-B cells.

Bone marrow cells from G2A-/- and G2A+/+ mice were infected with retroviruses encoding BCR-ABL. 1×10$^6$ infected cells were intravenously injected into the tail vein of sublethally irradiated SCIDs (FIG. 18). Mice were then monitored for signs of illness daily. SCID mice challenged with BCR-ABL expressing G2A-/- bone marrow developed leukemia more rapidly (shorter disease latency) compared to those receiving BCR-ABL expressing G2A+/+ bone marrow (FIG. 19).

EXAMPLE 27

In Vitro T Cell Proliferation Assays

Figure 20:
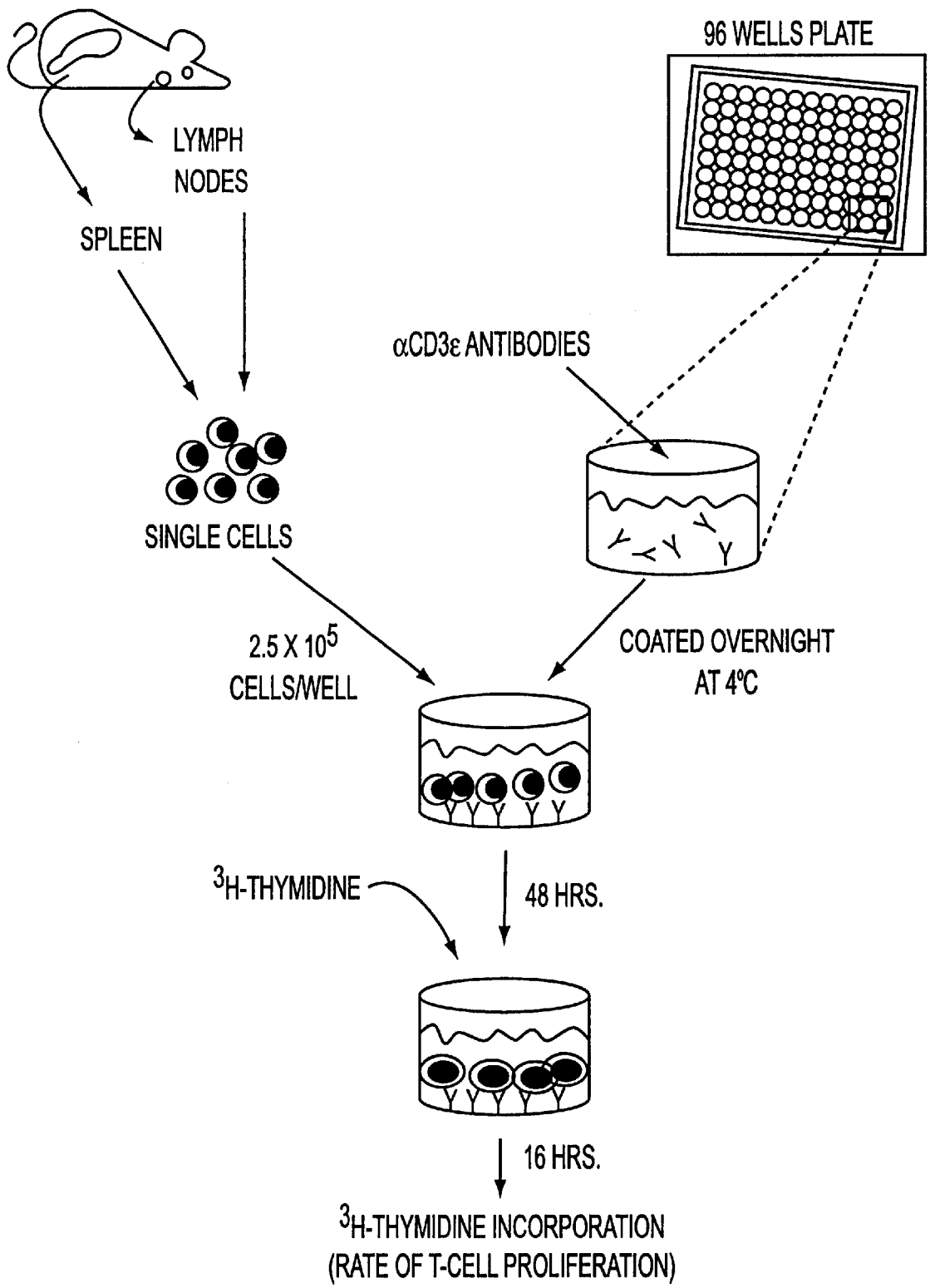
FIG. 20 is a schematic diagram showing in vitro T-cell proliferation stimulated by CD3ε cross-linking.
Figure 21:
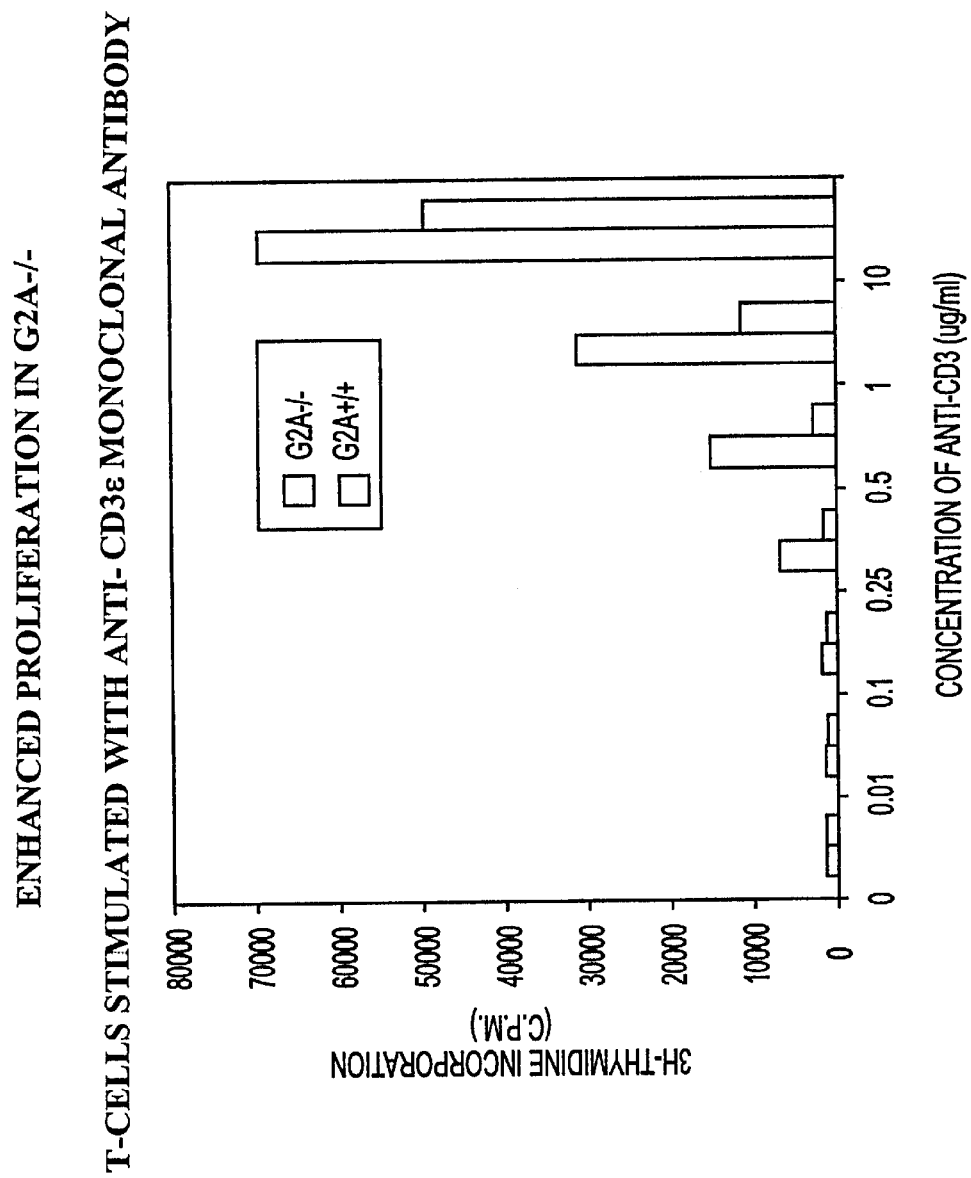
FIG. 21 is a graph showing enhanced proliferation of G2A−/− T-cells stimulated with anti-CD3ε monoclonal antibody.

T cells from G2A+/+ or G2A-/- mice were stimulated by culture with different concentrations of anti-CD3 mAb. 48 hours after stimulation, cultures were pulsed with [3H] thymidine. T cell proliferation was assessed in triplicate by [3H] thymidine incorporation (FIG. 20). G2A-/- T cells exhibited enhanced proliferative responses to various doses of anti-CD3 mAb (FIG. 21).

Figure 22:
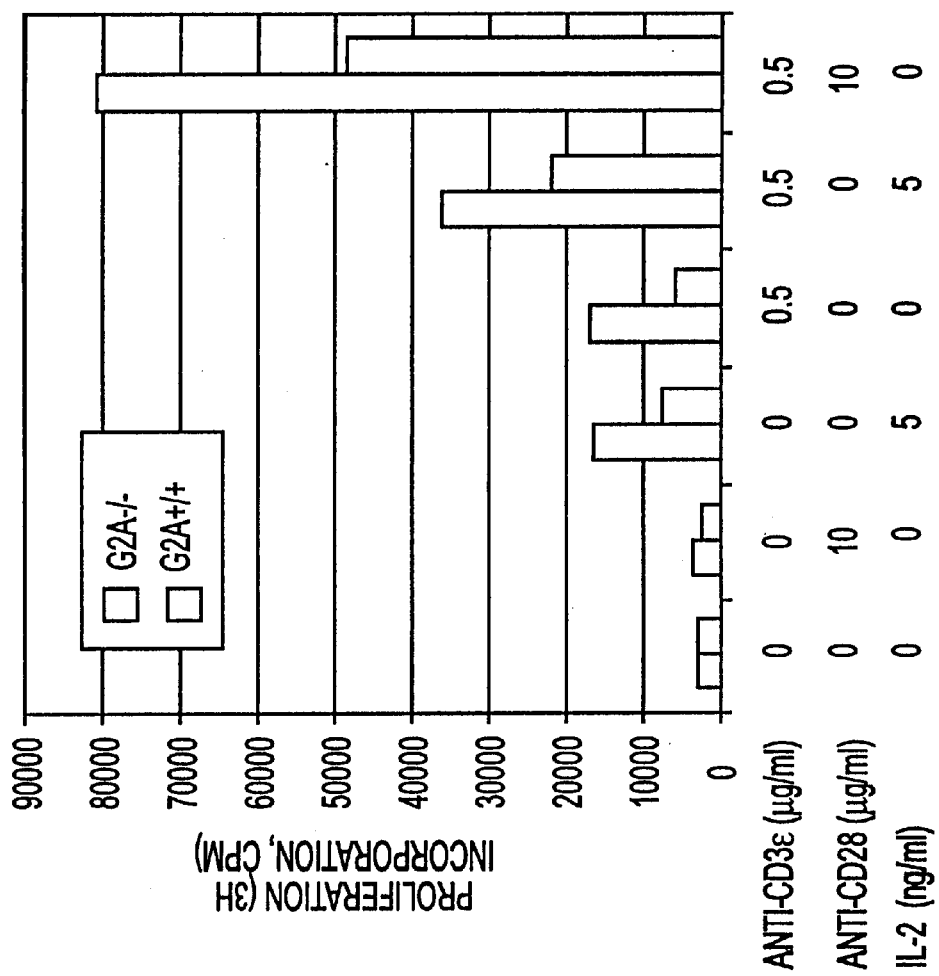
FIG. 22 is a graph showing enhanced T-cell proliferation in response to anti-CD3 and CD28/IL-2.

T cells from G2A+/+ or G2A-/- mice were stimulated by culture with anti-CD3 mAb in the presence or absence of 10 μg/ml anti-CD28 mAb or 5 ng/ml of IL-2. 48 hours after stimulation, cultures were pulsed with [3H] thymidine for 16 hours. T cell proliferation was assessed in triplicate by [3H] thymidine incorporation. Exogenous IL-2 or co-stimulation with anti-CD28 did not suppress the hyperproliferative phenotype of G2A-/- T cells (FIG. 22). When T cells were co-stimulated with anti-CD3 mAb and either IL-2 or anti-CD28 mAb, proliferative responses of both G2A+/+ and G2A-/- T cells were increased (FIG. 22). However, the proliferative response of G2A-/- T cells is still higher than that of G2A+/+ T cells.

EXAMPLE 28

Kinetics of G2A-/- and G2A+/+ T Cell Proliferation

Figure 23:
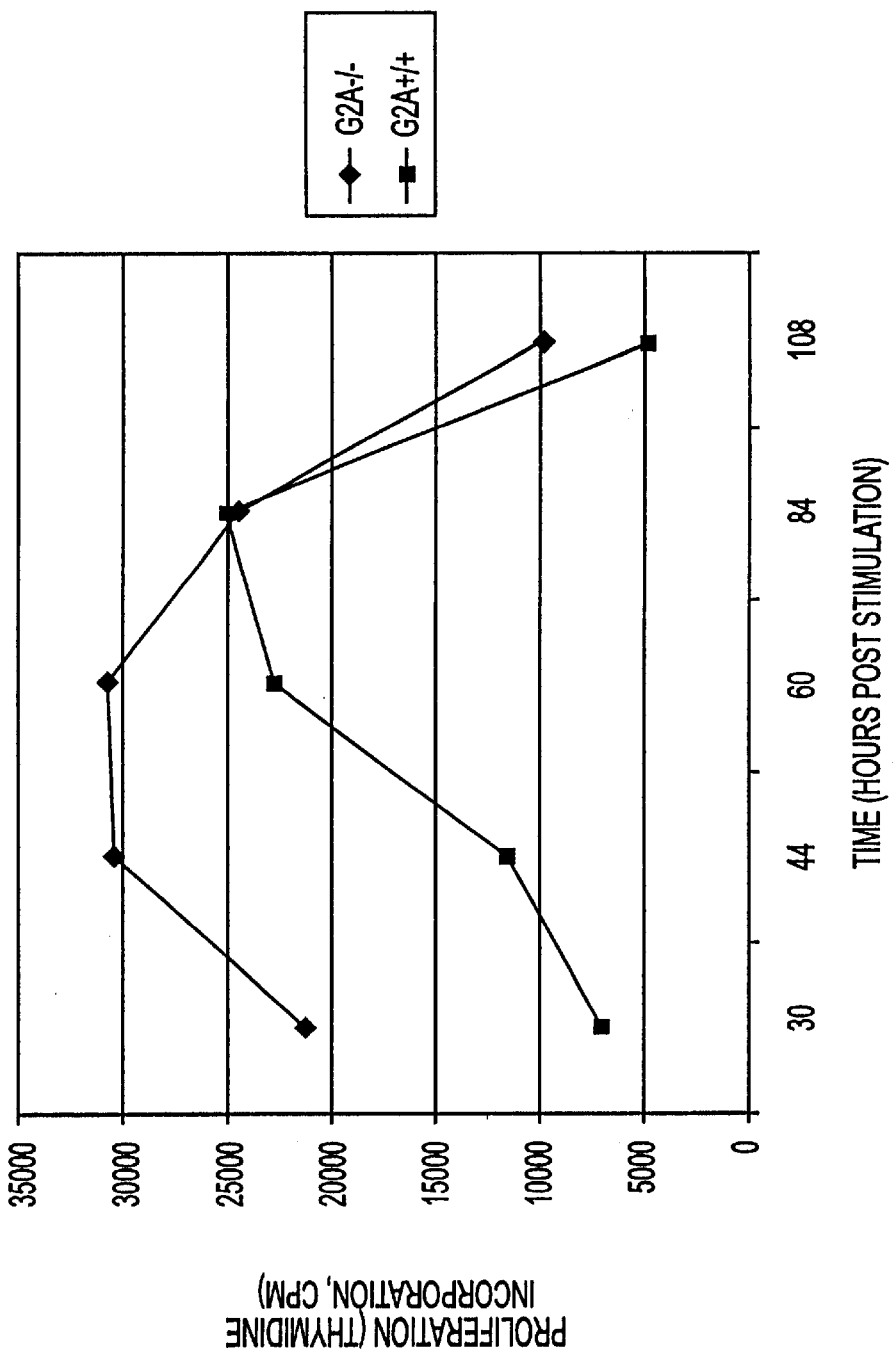
FIG. 23 is a graph showing the kinetics of G2A−/− and G2A+/+ T-cell proliferation stimulated by anti-CD3ε cross-linking (5 μg/ml).
Figure 24:
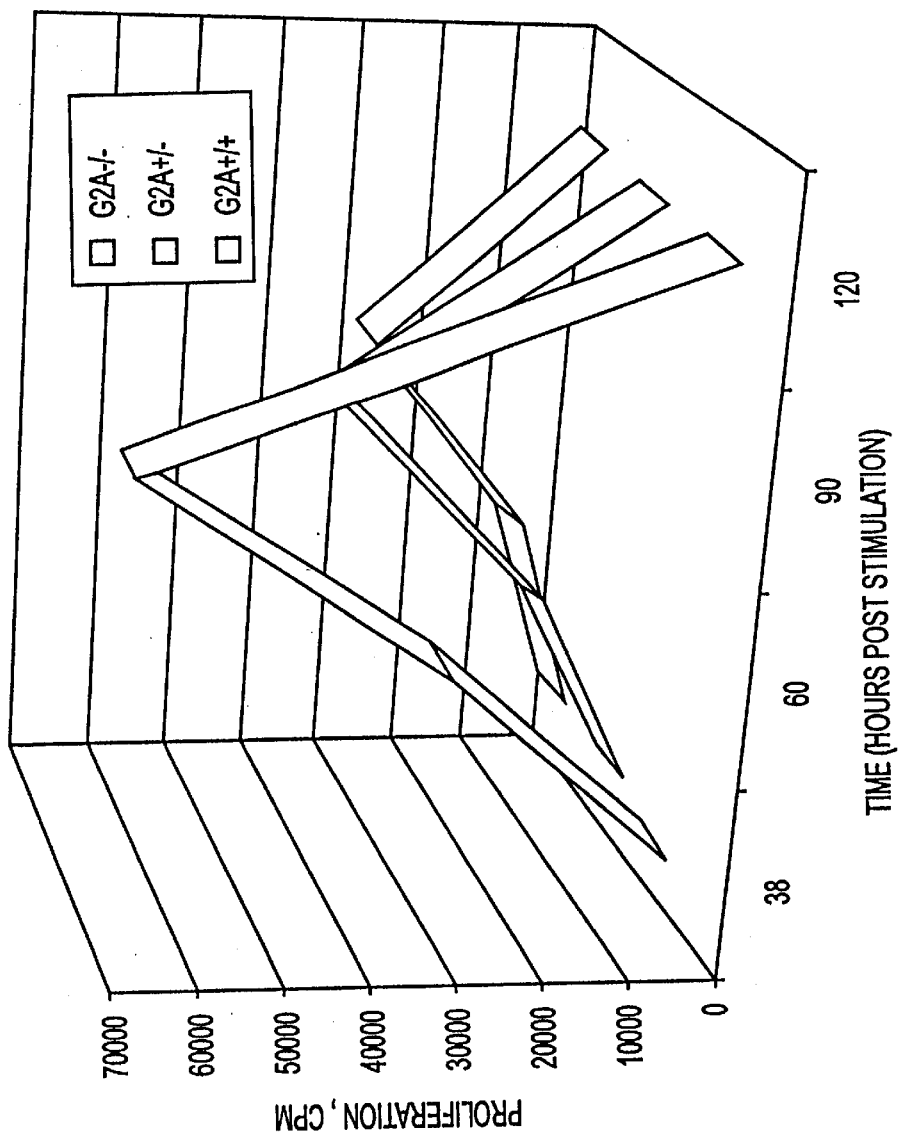
FIG. 24 is a graph showing the kinetics of T-cell proliferation stimulated by ConA (0.5 μg/ml) in G2A−/−, G2A +/− and G2A+/+ cells.

G2A-/-, G2A+/- or G2A+/+ T cells were stimulated by culture with anti-CD3 mAb (5µg/ml) or ConA (0.5 µg/ml). T cell proliferation was assessed in triplicate by labeling with [3H] thymidine for 12 hours at indicated time points post-stimulation. The results (FIGS. 23–24) show that greater proliferation occurred in T-cells from G2A-/- mice.

EXAMPLE 29

Figure 25:
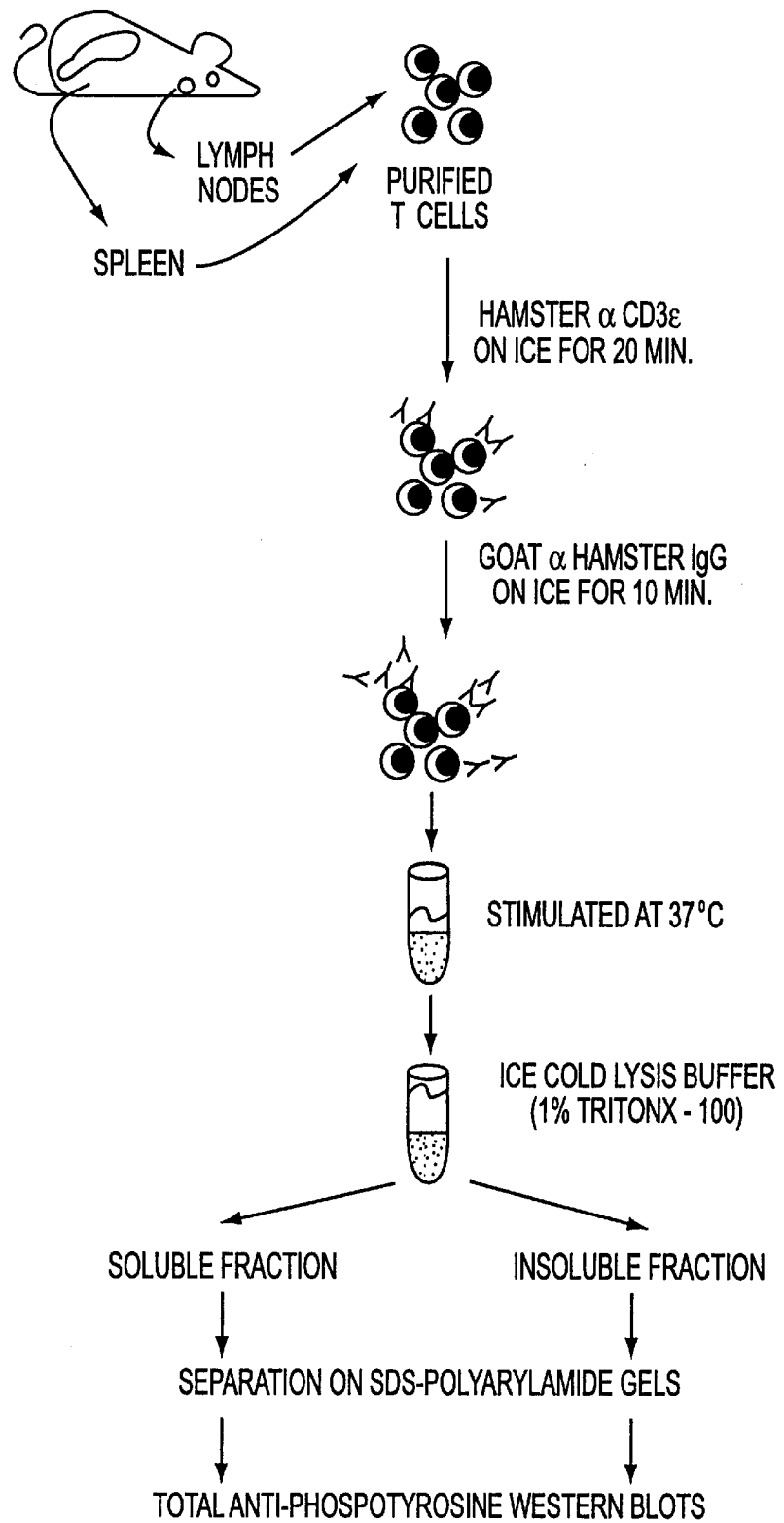
FIG. 25 is a schematic diagram showing tyrosine phosphorylation of proteins in T cells after anti-CD3ε stimulation.

Enhanced Tyrosine Phosphorylation of Proteins in G2A-/- T Cells after Anti-CD3ε Stimulation Purified peripheral T cells from G2A+/+ or G2A-/- mice were incubated with hamster anti-CD3ε on ice for 20 min, washed and subsequently incubated with goat anti-hamster IgG on ice for 10 min. Cells were stimulated via cross-linking of CD3 receptors for the indicated times by shift to 37° C. Cells were lysed in ice cold lysis buffer (50 mM Tris, pH7.4; 1% TritonX-100; 150 nM NaCl; 5 mM NaF; 1 mM NaVO$_4$; 5 mM EDTA; 1 µg/ml each of aprotinin and leupeptin). The total lysates were then seperated on SDS-polyacrylamide gels and anti-phosphotyrosine western blots were performed (FIG. 25). The results show an enhanced tyrosine phosphorylation of proteins in G2A-/--T cells after anti-CD3ε stimulation.

EXAMPLE 30

In Vitro B Cell Proliferation

Figure 26:
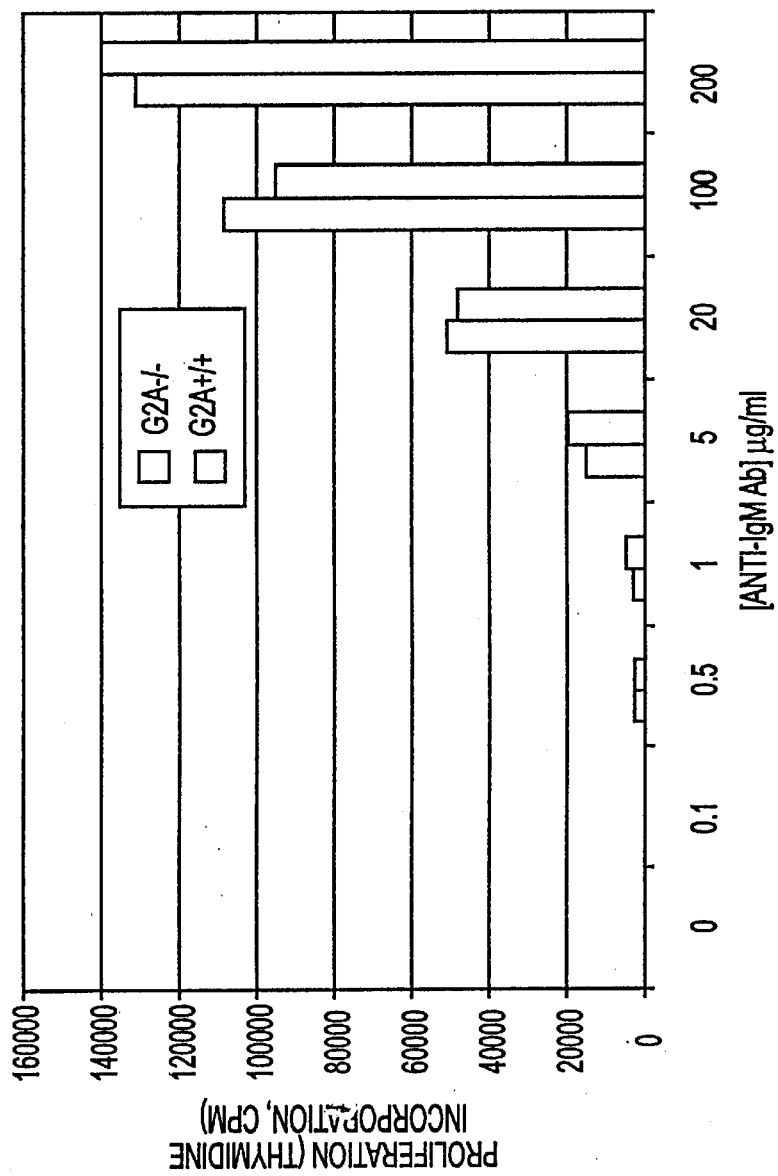
FIG. 26 is a graph showing G2A−/− and G2A+/+ B-cell proliferation stimulated by anti-IgM cross-linking.

Splenic B cells from G2A+/+ or G2A-/- mice were stimulated by anti-IgM cross-linking or incubation with LPS. 48 hours after stimulation, cultures were pulsed with [3H] thymidine for 16 hours. B cell proliferation was assessed in triplicates by [3H] thymidine incorporation. Both G2A-/- and G2A+/+B cells respond equally to stimulation by either anti-IgM cross-linking (FIG. 26) or LPS (FIG. 27).

The structural and biochemical basis of antigen recognition by the T-cell receptor (TCR)-CD3 signaling complex has been illuminated greatly over the past years. Deficiency or defective function of proteins involved in signaling thruogh these receptors are associated with immune dysfunction T cells undergo actin polymerization and cytoskeletal rearrangement upon T-cell activation. This process is regulated by Rho family GTPases. G2A may play a vital role in this process.

It should be noted that the present invention is not limited to only those embodiments described in the Detailed Description. Any embodiment which retains the spirit of the present invention should be considered to be within its scope. However, the invention is only limited by the scope of the appended claims.

What is claimed is:

1. A method for determining the presence of G2A in a biological sample comprising contacting the sample with a polynucleotide that specifically hybridizes to a G2A nucleotide sequence shown in SEQ ID NO:1 or 3 and detecting the presence of a hybridization complex formed by the hybridization of the polynucleotide with G2A nucleotide in the sample, wherein the presence of a hybridization complex indicates the presence of G2A polynucleotide within the sample.

2. The method of claim 1, wherein the presence of a hybridization complex is determined by Nothern analysis.

3. The tnethod of claim 1, wherein the presence of a hybridization complex is determined by polymerase chain reaction.

* * * * *

UNITED STATES PATENT AND TRADEMARK OFFICE
CERTIFICATE OF CORRECTION

PATENT NO. : 6,514,696 B1  Page 1 of 1
APPLICATION NO. : 09/553875
DATED : February 4, 2003
INVENTOR(S) : Weng and Witte It is certified that error appears in the above-identified patent and that said Letters Patent is hereby corrected as shown below:

Column 1

Line 3, please insert

STATEMENT OF GOVERNMENT SUPPORT

--The present invention was made with Government support by Grant CA 053867 awarded by the National Institutes of Health. The Government has certain rights in this invention.--

Signed and Sealed this

Thirtieth Day of June, 2009

JOHN DOLL
*Acting Director of the United States Patent and Trademark Office*